United States Patent
Reider Apel et al.

(10) Patent No.: US 12,195,775 B2
(45) Date of Patent: Jan. 14, 2025

(54) ENGINEERED ENZYMES AND BIOPRODUCTION OF BAKUCHIOL

(71) Applicant: Inscripta, Inc., Pleasanton, CA (US)

(72) Inventors: Amanda Reider Apel, Alameda, CA (US); Karolina Kalbarczyk, Santa Cruz, CA (US); Drew Fraser Thacker, Alameda, CA (US); Abhinav Kumar, Pleasant Hill, CA (US)

(73) Assignee: Inscripta, Inc., Pleasanton, CA (US)

( * ) Notice: Subject to any disclaimer, the term of this patent is extended or adjusted under 35 U.S.C. 154(b) by 0 days.

(21) Appl. No.: 18/117,082

(22) Filed: Mar. 3, 2023

(65) Prior Publication Data
US 2023/0340448 A1    Oct. 26, 2023

Related U.S. Application Data

(60) Provisional application No. 63/401,063, filed on Aug. 25, 2022, provisional application No. 63/316,855, filed on Mar. 4, 2022, provisional application No. 63/316,859, filed on Mar. 4, 2022.

(51) Int. Cl.
*C12N 9/90* (2006.01)
*C12N 1/18* (2006.01)
*C12N 1/20* (2006.01)
*C12P 7/22* (2006.01)
*C12R 1/19* (2006.01)
*C12R 1/865* (2006.01)

(52) U.S. Cl.
CPC ............... *C12N 9/90* (2013.01); *C12N 1/185* (2021.05); *C12N 1/205* (2021.05); *C12P 7/22* (2013.01); *C12Y 504/04* (2013.01); *C12R 2001/19* (2021.05); *C12R 2001/865* (2021.05)

(58) Field of Classification Search
CPC .......... C12N 9/90; C12N 1/205; C12N 1/185; C12P 7/22; C12Y 504/04; C12R 2001/19; C12R 2001/865
See application file for complete search history.

(56) References Cited

U.S. PATENT DOCUMENTS

| | | |
|---|---|---|
| 2011/0223267 A1 | 9/2011 | Jia et al. |
| 2024/0101614 A1 | 3/2024 | Apel et al. |

FOREIGN PATENT DOCUMENTS

| | | |
|---|---|---|
| CN | 113173835 A | 7/2021 |

OTHER PUBLICATIONS

Database UniProt, Accession No. A0A8B8LVJ5, Subname: Full= probably homogentisate phytyltransferase 1, chloroplastic isoform X2 {ECO:000313:RefSeq:XP_027360401.1, Jan. 19, 2022, 2 pages.
Database UniProt, Accession No. A0A8B8LXT1, Subname: Full= probably homogentisate phytyltransferase 1, chloroplastic-like isoform X1 {ECO:000313:RefSeq:XP_027360393.1, Jan. 19, 2022, 2 pages.
International Search Report and Written Opinion dated Jun. 19, 2023 in PCT/US2023/014450.
U.S. Appl. No. 18/455,221, filed Aug. 24, 2023, Apel et al.
Bitner et al., "Expression and Secretion Vectors for Yeast," Methods in Enzymology—Recombinant DNA, Jun. 28, 1989, 153(D):516-544.
Curran et al., "Use of High Capacity Terminators in *Saccharomyces cerevisiae* to Increase mRNA half-life and Improve Gene Expression Control for Metabolic Engineering Applications," Metab. Eng., Sep. 2013, 19:88-97.

*Primary Examiner* — Suzanne M Noakes
*Assistant Examiner* — Ciara A McKnight
(74) *Attorney, Agent, or Firm* — Foley Hoag LLP; Morgan Xu

(57) ABSTRACT

The present disclosure relates to synthetic biology and, in particular, the bioproduction of bakuchiol, and engineered enzymes for producing the same.

21 Claims, 12 Drawing Sheets
Specification includes a Sequence Listing.

FIG. 5
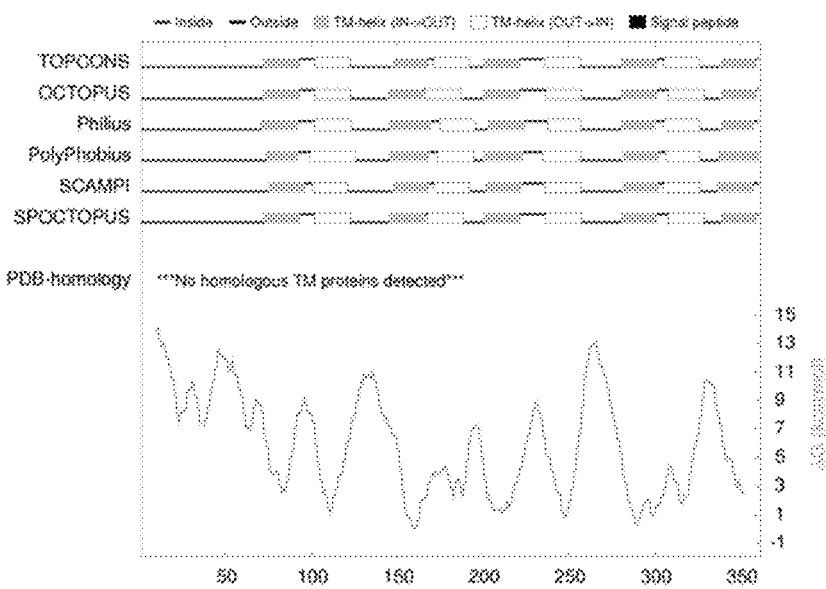
BAK28
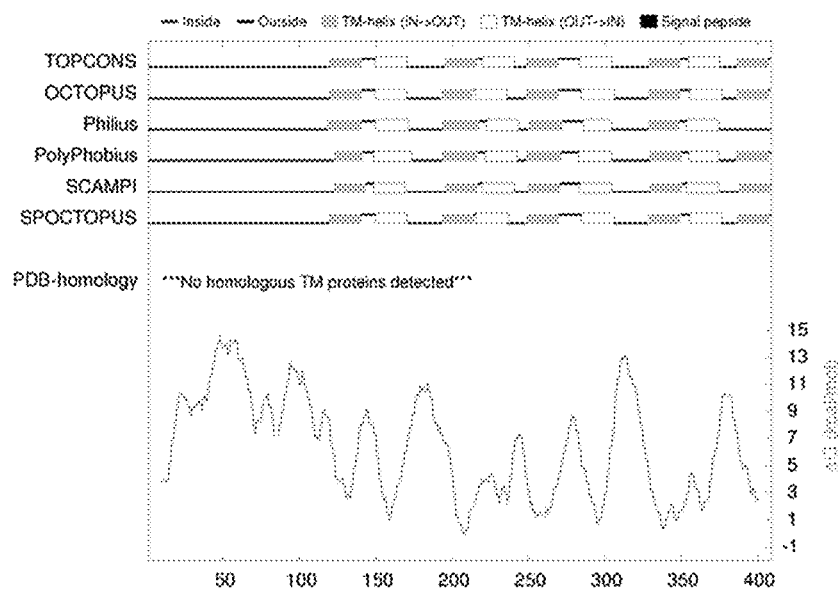
BAK36

FIG. 7

BAK36

Sequences producing significant alignments select all  100 sequences selected

| | Description | Scientific Name | Max Score | Total Score | Query Cover | E value | Per. Ident | Acc. Len | Accession |
|---|---|---|---|---|---|---|---|---|---|
| | homogentisate phytyltransferase 1, chloroplastic [Cajanus cajan] | Cajanus cajan | 494 | 494 | 100% | 8e-171 | 59.66% | 418 | XP_020225944.1 |
| | homogentisate phytyltransferase 1, chloroplastic-like isoform X1 [Abrus precatorius] | Abrus precatorius | 488 | 488 | 100% | 2e-168 | 58.66% | 404 | XP_027360393.1 |
| | probable homogentisate phytyltransferase 1, chloroplastic isoform X2 [Abrus precatorius] | Abrus precatorius | 473 | 473 | 91% | 8e-163 | 61.93% | 388 | XP_027360461.1 |
| | putative homogentisate phytyltransferase [Lupinus albus] | Lupinus albus | 464 | 464 | 100% | 3e-159 | 55.50% | 407 | KAE9801654.1 |
| | putative homogentisate phytyltransferase 1, chloroplastic [Mucuna pruriens] | Mucuna pruriens | 457 | 457 | 96% | 9e-157 | 57.68% | 379 | RDX60940.1 |
| | homogentisate phytyltransferase [Clitoria ternatea] | Clitoria ternatea | 456 | 456 | 100% | 7e-156 | 55.99% | 407 | ALR81191.1 |

BAK28

Sequences producing significant alignments select all  100 sequences selected

| | Description | Scientific Name | Max Score | Total Score | Query Cover | E value | Per. Ident | Acc. Len | Accession |
|---|---|---|---|---|---|---|---|---|---|
| | probable homogentisate phytyltransferase 1, chloroplastic isoform X2 [Abrus precatorius] | Abrus precatorius | 460 | 460 | 99% | 2e-158 | 62.50% | 388 | XP_027360461.1 |
| | homogentisate phytyltransferase 1, chloroplastic-like isoform X1 [Abrus precatorius] | Abrus precatorius | 459 | 459 | 99% | 7e-158 | 62.50% | 404 | XP_027360393.1 |
| | homogentisate phytyltransferase 1, chloroplastic [Cajanus cajan] | Cajanus cajan | 454 | 454 | 98% | 9e-156 | 62.25% | 418 | XP_020225944.1 |
| | hypothetical protein TanjilG_16434 [Lupinus angustifolius] | Lupinus angustifolius | 440 | 440 | 99% | 2e-150 | 57.78% | 402 | ONV19414.1 |
| | PREDICTED: homogentisate phytyltransferase 1, chloroplastic-like [Lupinus angustifolius] | Lupinus angustifolius | 439 | 439 | 99% | 3e-150 | 57.78% | 391 | XP_019420394.1 |
| | homogentisate phytyltransferase [Clitoria ternatea] | Clitoria ternatea | 437 | 437 | 99% | 4e-149 | 58.05% | 407 | ALR81191.1 |

BAK28- Light Grey
T1: AA29-
T2: AA57-
T3: AA73-

BAK36- Dark Grey
T1: AA38-
T2: AA88-
T3: AA105-
T4: AA120-

Predicted structures using alpha-fold

Some residues show increases with multiple substitutions ~ 48

Largest decreases seen at residues:
- D203(ACFGIMTV) 17
- L234(CDEKPQS) 13
- K269(AEMRST) 9
- G313(FHIKLPQRWY) 30

V312 had varying impacts:
- Increased activity (8): F, Y 3, C
- Decreased Activity (6): M, A 3, Q Mostly AA inward

SEQUENCE LISTING

```
Sequence total quantity: 85
SEQ ID NO: 1           moltype = AA  length = 361
FEATURE                Location/Qualifiers
```

```
source                    1..361
                          mol_type = protein
                          organism = synthetic construct
VARIANT                   1
                          note = May or may not be present
SEQUENCE: 1
MHEYANMRHR QHNLKHNYGG IEGVSTCEDW ARNFVVNAAS GESLESHEAQ HHTPETLWGS    60
IKQFCDAFYR FSRPHVIIGT AVNIIVMSSL ALEKSSDISP KFFIGLFQVI VTILSMNIYT   120
AGINQLTDIE IDKINKPYLP LASGEYSYKT GVTIITLCAI LSLGVGWIVG SPPLFWSNFA   180
YFVLGTVYSI DLPLMRWKSH PALAALFFFV IRGLTFHVGF FLHLQTHVFK RPMMIPKPVM   240
FGTAFMSFFY VIIAFFKDIP DIEGDKDHGV KSLTMRLGQK RVFWICVSLL LTGYGAAIVV   300
GATSSFLWCK LITVSGHALL ASIFWNRAKS VDLKSHQEIT SLYMFMWKLF YAEYFIIPLM   360
R                                                                  361

SEQ ID NO: 2              moltype = AA  length = 409
FEATURE                   Location/Qualifiers
source                    1..409
                          mol_type = protein
                          organism = synthetic construct
VARIANT                   1
                          note = May or may not be present
SEQUENCE: 2
MASMFLGSLP LASSVNYIGR ITRSKNCTES YHATSYITNA SSNKTEKIKH EYANMRHRQH    60
NLKHNYGGIE GVSTCEDWAR NFVVNAASGE SLESHEAQHH TPETLWGSIK QFCDAFYRFS   120
RPHVIIGTAV NIIVMSSLAL EKSSDISPKF FIGLFQVIVT ILSMNIYTAG INQLTDIEID   180
KINKPYLPLA SGEYSYKTGV TIITLCAILS LGVGWIVGSP PLFWSNFAYF VLGTVYSIDL   240
PLMRWKSHPA LAALFFFVIR GLTFHVGFFL HLQTHVFKRP MMIPKSVMFG TAFMSFFYVI   300
IAFFKDIPDI EGDKDHGVKS LTMRLGQERV FWICVSLLLT GYGAAIVVGA TSSFLWCKLI   360
TVSGHALLAS IFWNRAKSVD LKSHQEITSL YMFMWKLFYA EYFIIPLMR              409

SEQ ID NO: 3              moltype = AA  length = 373
FEATURE                   Location/Qualifiers
source                    1..373
                          mol_type = protein
                          organism = synthetic construct
VARIANT                   1
                          note = May or may not be present
SEQUENCE: 3
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 4              moltype = AA  length = 373
FEATURE                   Location/Qualifiers
source                    1..373
                          mol_type = protein
                          organism = synthetic construct
VARIANT                   1
                          note = May or may not be present
SEQUENCE: 4
MTNASSNKTE KIKHEYANMR HRQHNLKHNY GGIEGVSTCE DWARNFVVNA ASGFSLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 5              moltype = AA  length = 373
FEATURE                   Location/Qualifiers
source                    1..373
                          mol_type = protein
                          organism = synthetic construct
VARIANT                   1
                          note = May or may not be present
SEQUENCE: 5
MTNASSNKTE KIKHEYANMR HRQHNLKHNY GGIEGVSTCE DWARNFVVNA ASGESLESHE    60
AQHHTPETLW DSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 6              moltype = AA  length = 373
```

```
FEATURE                 Location/Qualifiers
source                  1..373
                        mol_type = protein
                        organism = synthetic construct
VARIANT                 1
                        note = May or may not be present
SEQUENCE: 6
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSLDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 7            moltype = AA  length = 373
FEATURE                 Location/Qualifiers
source                  1..373
                        mol_type = protein
                        organism = synthetic construct
VARIANT                 1
                        note = May or may not be present
SEQUENCE: 7
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 8            moltype = AA  length = 373
FEATURE                 Location/Qualifiers
source                  1..373
                        mol_type = protein
                        organism = synthetic construct
VARIANT                 1
                        note = May or may not be present
SEQUENCE: 8
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 9            moltype = AA  length = 373
FEATURE                 Location/Qualifiers
source                  1..373
                        mol_type = protein
                        organism = synthetic construct
VARIANT                 1
                        note = May or may not be present
SEQUENCE: 9
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTGY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 10           moltype = AA  length = 373
FEATURE                 Location/Qualifiers
source                  1..373
                        mol_type = protein
                        organism = synthetic construct
VARIANT                 1
                        note = May or may not be present
SEQUENCE: 10
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLLLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373
```

```
SEQ ID NO: 11            moltype = AA  length = 373
FEATURE                  Location/Qualifiers
source                   1..373
                         mol_type = protein
                         organism = synthetic construct
VARIANT                  1
                         note = May or may not be present
SEQUENCE: 11
MTNASSNKTE KIKHEYANMR HRQHNLKHNY GGIEGVSTCE DWARNFVVNA ASGESLESHE     60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLVLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                       373

SEQ ID NO: 12            moltype = AA  length = 373
FEATURE                  Location/Qualifiers
source                   1..373
                         mol_type = protein
                         organism = synthetic construct
VARIANT                  1
                         note = May or may not be present
SEQUENCE: 12
MTNASSNKTE KIKHEYANMR HRQHNLKHNY GGIEGVSTCE DWARNFVVNA ASGESLESHE     60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPYMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                       373

SEQ ID NO: 13            moltype = AA  length = 373
FEATURE                  Location/Qualifiers
source                   1..373
                         mol_type = protein
                         organism = synthetic construct
VARIANT                  1
                         note = May or may not be present
SEQUENCE: 13
MTNASSNKTE KIKHEYANMR HRQHNLKHNY GGIEGVSTCE DWARNFVVNA ASGESLESHE     60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRSK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                       373

SEQ ID NO: 14            moltype = AA  length = 373
FEATURE                  Location/Qualifiers
source                   1..373
                         mol_type = protein
                         organism = synthetic construct
VARIANT                  1
                         note = May or may not be present
SEQUENCE: 14
MTNASSNKTE KIKHEYANMR HRQHNLKHNY GGIEGVSTCE DWARNFVVNA ASGESLESHE     60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRCK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                       373

SEQ ID NO: 15            moltype = AA  length = 373
FEATURE                  Location/Qualifiers
source                   1..373
                         mol_type = protein
                         organism = synthetic construct
VARIANT                  1
                         note = May or may not be present
SEQUENCE: 15
MTNASSNKTE KIKHEYANMR HRQHNLKHNY GGIEGVSTCE DWARNFVVNA ASGESLESHE     60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRVK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                       373
```

```
SEQ ID NO: 16          moltype = AA  length = 373
FEATURE                Location/Qualifiers
source                 1..373
                       mol_type = protein
                       organism = synthetic construct
VARIANT                1
                       note = May or may not be present
SEQUENCE: 16
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ  120
VIVTILSMNI YTAGINQLTD IEIDKINKPY LPLASGEYSY KTGVTIITLC AILSLGVGWI  180
VGSPPLFWSN FAYFVLGTVY SIDLPLMRTK SHPALAALFF FVIRGLTFHV GFFLHLQTHV  240
FKRPMMIPKS VMFGTAFMSF FYVIIAFFKD IPDIEGDKDH GVKSLTMRLG QERVFWICVS  300
LLLTGYGAAI VVGATSSFLW CKLITVSGHA LLASIFWNRA KSVDLKSHQE ITSLYMFMWK  360
LFYAEYFIIP LMR                                                    373

SEQ ID NO: 17          moltype = AA  length = 373
FEATURE                Location/Qualifiers
source                 1..373
                       mol_type = protein
                       organism = synthetic construct
VARIANT                1
                       note = May or may not be present
SEQUENCE: 17
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ  120
VIVTILSMNI YTAGINQLTD IEIDKINKPY LPLASGEYSY KTGVTIITLC AILSLGVGWI  180
VGSPPLFWSN FAYFVLGTVY SIDLPLMRYK SHPALAALFF FVIRGLTFHV GFFLHLQTHV  240
FKRPMMIPKS VMFGTAFMSF FYVIIAFFKD IPDIEGDKDH GVKSLTMRLG QERVFWICVS  300
LLLTGYGAAI VVGATSSFLW CKLITVSGHA LLASIFWNRA KSVDLKSHQE ITSLYMFMWK  360
LFYAEYFIIP LMR                                                    373

SEQ ID NO: 18          moltype = AA  length = 373
FEATURE                Location/Qualifiers
source                 1..373
                       mol_type = protein
                       organism = synthetic construct
VARIANT                1
                       note = May or may not be present
SEQUENCE: 18
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ  120
VIVTILSMNI YTAGINQLTD IEIDKINKPY LPLASGEYSY KTGVTIITLC AILSLGVGWI  180
VGSPPLFWSN FAYFVLGTVY SIDLPLMRRK SHPALAALFF FVIRGLTFHV GFFLHLQTHV  240
FKRPMMIPKS VMFGTAFMSF FYVIIAFFKD IPDIEGDKDH GVKSLTMRLG QERVFWICVS  300
LLLTGYGAAI VVGATSSFLW CKLITVSGHA LLASIFWNRA KSVDLKSHQE ITSLYMFMWK  360
LFYAEYFIIP LMR                                                    373

SEQ ID NO: 19          moltype = AA  length = 373
FEATURE                Location/Qualifiers
source                 1..373
                       mol_type = protein
                       organism = synthetic construct
VARIANT                1
                       note = May or may not be present
SEQUENCE: 19
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ  120
VIVTILSMNI YTAGINQLTD IEIDKINKPY LPLASGEYSY KTGVTIITLC AILSLGVGWI  180
VGSPPLFWSN FAYFVLGTVY SIDLPLMRMK SHPALAALFF FVIRGLTFHV GFFLHLQTHV  240
FKRPMMIPKS VMFGTAFMSF FYVIIAFFKD IPDIEGDKDH GVKSLTMRLG QERVFWICVS  300
LLLTGYGAAI VVGATSSFLW CKLITVSGHA LLASIFWNRA KSVDLKSHQE ITSLYMFMWK  360
LFYAEYFIIP LMR                                                    373

SEQ ID NO: 20          moltype = AA  length = 373
FEATURE                Location/Qualifiers
source                 1..373
                       mol_type = protein
                       organism = synthetic construct
VARIANT                1
                       note = May or may not be present
SEQUENCE: 20
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ  120
VIVTILSMNI YTAGINQLTD IEIDKINKPY LPLASGEYSY KTGVTIITLC AILSLGVGWI  180
VGSPPLFWSN FAYFVLGTVY SIDLPLMRQK SHPALAALFF FVIRGLTFHV GFFLHLQTHV  240
FKRPMMIPKS VMFGTAFMSF FYVIIAFFKD IPDIEGDKDH GVKSLTMRLG QERVFWICVS  300
LLLTGYGAAI VVGATSSFLW CKLITVSGHA LLASIFWNRA KSVDLKSHQE ITSLYMFMWK  360
```

```
LFYAEYFIIP LMR                                                                373

SEQ ID NO: 21            moltype = AA   length = 373
FEATURE                  Location/Qualifiers
source                   1..373
                         mol_type = protein
                         organism = synthetic construct
VARIANT                  1
                         note = May or may not be present
SEQUENCE: 21
MTNASSNKTE KIKHEYANMR HRQHNLKHNY GGIEGVSTCE DWARNFVVNA ASGESLESHE  60
AQHHTPETLW GSIKQFCDAF YRFSRPHVII GTAVNIIVMS SLALEKSSDI SPKFFIGLFQ 120
VIVTILSMNI YTAGINQLTD IEIDKINKPY LPLASGEYSY KTGVTIITLC AILSLGVGWI 180
VGSPPLFWSN FAYFVLGTVY SIDLPLMRWK SHPALAALFF FVIRGMTFHV GFFLHLQTHV 240
FKRPMMIPKS VMFGTAFMSF FYVIIAFFKD IPDIEGDKDH GVKRGSLTMRLG QERVFWICVS 300
LLLTGYGAAI VVGATSSFLW CKLITVSGHA LLASIFWNRA KSVDLKSHQE ITSLYMFMWK 360
LFYAEYFIIP LMR                                                    373

SEQ ID NO: 22            moltype = AA   length = 373
FEATURE                  Location/Qualifiers
source                   1..373
                         mol_type = protein
                         organism = synthetic construct
VARIANT                  1
                         note = May or may not be present
SEQUENCE: 22
MTNASSNKTE KIKHEYANMR HRQHNLKHNY GGIEGVSTCE DWARNFVVNA ASGESLESHE  60
AQHHTPETLW GSIKQFCDAF YRFSRPHVII GTAVNIIVMS SLALEKSSDI SPKFFIGLFQ 120
VIVTILSMNI YTAGINQLTD IEIDKINKPY LPLASGEYSY KTGVTIITLC AILSLGVGWI 180
VGSPPLFWSN FAYFVLGTVY SIDLPLMRWK SHPALAALFF FVIRGLTFHV GFFQHLQTHV 240
FKRPMMIPKS VMFGTAFMSF FYVIIAFFKD IPDIEGDKDH GVKSLTMRLG QERVFWICVS 300
LLLTGYGAAI VVGATSSFLW CKLITVSGHA LLASIFWNRA KSVDLKSHQE ITSLYMFMWK 360
LFYAEYFIIP LMR                                                    373

SEQ ID NO: 23            moltype = AA   length = 373
FEATURE                  Location/Qualifiers
source                   1..373
                         mol_type = protein
                         organism = synthetic construct
VARIANT                  1
                         note = May or may not be present
SEQUENCE: 23
MTNASSNKTE KIKHEYANMR HRQHNLKHNY GGIEGVSTCE DWARNFVVNA ASGESLESHE  60
AQHHTPETLW GSIKQFCDAF YRFSRPHVII GTAVNIIVMS SLALEKSSDI SPKFFIGLFQ 120
VIVTILSMNI YTAGINQLTD IEIDKINKPY LPLASGEYSY KTGVTIITLC AILSLGVGWI 180
VGSPPLFWSN FAYFVLGTVY SIDLPLMRWK SHPALAALFF FVIRGLTFHV GFFLHLQTHV 240
FKRPMMIPKS VMFGTAEMSF FYVIIAFFKD IPDIEGDKDH GVKSLTMRLG QERVFWICVS 300
LLLTGYGAAI VVGATSSFLW CKLITVSGHA LLASIFWNRA KSVDLKSHQE ITSLYMFMWK 360
LFYAEYFIIP LMR                                                    373

SEQ ID NO: 24            moltype = AA   length = 373
FEATURE                  Location/Qualifiers
source                   1..373
                         mol_type = protein
                         organism = synthetic construct
VARIANT                  1
                         note = May or may not be present
SEQUENCE: 24
MTNASSNKTE KIKHEYANMR HRQHNLKHNY GGIEGVSTCE DWARNFVVNA ASGESLESHE  60
AQHHTPETLW GSIKQFCDAF YRFSRPHVII GTAVNIIVMS SLALEKSSDI SPKFFIGLFQ 120
VIVTILSMNI YTAGINQLTD IEIDKINKPY LPLASGEYSY KTGVTIITLC AILSLGVGWI 180
VGSPPLFWSN FAYFVLGTVY SIDLPLMRWK SHPALAALFF FVIRGLTFHV GFFLHLQTHV 240
FKRPMMIPKS VMFGTAFMSF FYVIIAFFRD IPDIEGDKDH GVKSLTMRLG QERVFWICVS 300
LLLTGYGAAI VVGATSSFLW CKLITVSGHA LLASIFWNRA KSVDLKSHQE ITSLYMFMWK 360
LFYAEYFIIP LMR                                                    373

SEQ ID NO: 25            moltype = AA   length = 373
FEATURE                  Location/Qualifiers
source                   1..373
                         mol_type = protein
                         organism = synthetic construct
VARIANT                  1
                         note = May or may not be present
SEQUENCE: 25
MTNASSNKTE KIKHEYANMR HRQHNLKHNY GGIEGVSTCE DWARNFVVNA ASGESLESHE  60
AQHHTPETLW GSIKQFCDAF YRFSRPHVII GTAVNIIVMS SLALEKSSDI SPKFFIGLFQ 120
VIVTILSMNI YTAGINQLTD IEIDKINKPY LPLASGEYSY KTGVTIITLC AILSLGVGWI 180
VGSPPLFWSN FAYFVLGTVY SIDLPLMRWK SHPALAALFF FVIRGLTFHV GFFLHLQTHV 240
FKRPMMIPKS VMFGTAFMSF FYVIIAFFKD IPDLEGDKDH GVKSLTMRLG QERVFWICVS 300
```

```
LLLTGYGAAI VVGATSSFLW CKLITVSGHA LLASIFWNRA KSVDLKSHQE ITSLYMFMWK    360
LFYAEYFIIP LMR                                                      373

SEQ ID NO: 26           moltype = AA  length = 373
FEATURE                 Location/Qualifiers
source                  1..373
                        mol_type = protein
                        organism = synthetic construct
VARIANT                 1
                        note = May or may not be present
SEQUENCE: 26
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKCH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                      373

SEQ ID NO: 27           moltype = AA  length = 373
FEATURE                 Location/Qualifiers
source                  1..373
                        mol_type = protein
                        organism = synthetic construct
VARIANT                 1
                        note = May or may not be present
SEQUENCE: 27
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKKH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                      373

SEQ ID NO: 28           moltype = AA  length = 373
FEATURE                 Location/Qualifiers
source                  1..373
                        mol_type = protein
                        organism = synthetic construct
VARIANT                 1
                        note = May or may not be present
SEQUENCE: 28
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKRH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                      373

SEQ ID NO: 29           moltype = AA  length = 373
FEATURE                 Location/Qualifiers
source                  1..373
                        mol_type = protein
                        organism = synthetic construct
VARIANT                 1
                        note = May or may not be present
SEQUENCE: 29
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKMH GVKSLTMRLG QERVFWICVS    300
LLLTGYGAAI VVGATSSFLW CKLITVSGHA LLASIFWNRA KSVDLKSHQE ITSLYMFMWK    360
LFYAEYFIIP LMR                                                      373

SEQ ID NO: 30           moltype = AA  length = 373
FEATURE                 Location/Qualifiers
source                  1..373
                        mol_type = protein
                        organism = synthetic construct
VARIANT                 1
                        note = May or may not be present
SEQUENCE: 30
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
```

```
FKRPMMIPKS VMFGTAFMSF FYVIIAFFKD IPDIEGDKLH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 31           moltype = AA  length = 373
FEATURE                 Location/Qualifiers
source                  1..373
                        mol_type = protein
                        organism = synthetic construct
VARIANT                 1
                        note = May or may not be present
SEQUENCE: 31
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTVRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 32           moltype = AA  length = 373
FEATURE                 Location/Qualifiers
source                  1..373
                        mol_type = protein
                        organism = synthetic construct
VARIANT                 1
                        note = May or may not be present
SEQUENCE: 32
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTFRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 33           moltype = AA  length = 373
FEATURE                 Location/Qualifiers
source                  1..373
                        mol_type = protein
                        organism = synthetic construct
VARIANT                 1
                        note = May or may not be present
SEQUENCE: 33
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTYRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 34           moltype = AA  length = 373
FEATURE                 Location/Qualifiers
source                  1..373
                        mol_type = protein
                        organism = synthetic construct
VARIANT                 1
                        note = May or may not be present
SEQUENCE: 34
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAV VVGATSSFLW CKLITVSGHA LLASIFWNRA KSVDLKSHQE ITSLYMFMWK   360
LFYAEYFIIP LMR                                                     373

SEQ ID NO: 35           moltype = AA  length = 373
FEATURE                 Location/Qualifiers
source                  1..373
                        mol_type = protein
                        organism = synthetic construct
VARIANT                 1
                        note = May or may not be present
SEQUENCE: 35
MTNASSNKTE KIKHEYANMR HRQHNLKHNY GGIEGVSTCE DWARNFVVNA ASGESLESHE   60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
```

```
                                                         -continued

VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VWGATSSFLW CKLITVSGHA LLASIFWNRA KSVDLKSHQE ITSLYMFMWK    360
LFYAEYFIIP LMR                                                      373

SEQ ID NO: 36          moltype = AA  length = 373
FEATURE                Location/Qualifiers
source                 1..373
                       mol_type = protein
                       organism = synthetic construct
VARIANT                1
                       note = May or may not be present
SEQUENCE: 36
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VAGATSSFLW CKLITVSGHA LLASIFWNRA KSVDLKSHQE ITSLYMFMWK    360
LFYAEYFIIP LMR                                                      373

SEQ ID NO: 37          moltype = AA  length = 373
FEATURE                Location/Qualifiers
source                 1..373
                       mol_type = protein
                       organism = synthetic construct
VARIANT                1
                       note = May or may not be present
SEQUENCE: 37
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VFGATSSFLW CKLITVSGHA LLASIFWNRA KSVDLKSHQE ITSLYMFMWK    360
LFYAEYFIIP LMR                                                      373

SEQ ID NO: 38          moltype = AA  length = 373
FEATURE                Location/Qualifiers
source                 1..373
                       mol_type = protein
                       organism = synthetic construct
VARIANT                1
                       note = May or may not be present
SEQUENCE: 38
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VGGATSSFLW CKLITVSGHA LLASIFWNRA KSVDLKSHQE ITSLYMFMWK    360
LFYAEYFIIP LMR                                                      373

SEQ ID NO: 39          moltype = AA  length = 373
FEATURE                Location/Qualifiers
source                 1..373
                       mol_type = protein
                       organism = synthetic construct
VARIANT                1
                       note = May or may not be present
SEQUENCE: 39
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VYGATSSFLW CKLITVSGHA LLASIFWNRA KSVDLKSHQE ITSLYMFMWK    360
LFYAEYFIIP LMR                                                      373

SEQ ID NO: 40          moltype = AA  length = 373
FEATURE                Location/Qualifiers
source                 1..373
                       mol_type = protein
                       organism = synthetic construct
VARIANT                1
                       note = May or may not be present
SEQUENCE: 40
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
```

```
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VCGATSSFLW CKLITVSGHA LLASIFWNRA KSVDLKSHQE ITSLYMFMWK    360
LFYAEYFIIP LMR                                                      373

SEQ ID NO: 41             moltype = AA  length = 373
FEATURE                   Location/Qualifiers
source                    1..373
                          mol_type = protein
                          organism = synthetic construct
VARIANT                   1
                          note = May or may not be present
SEQUENCE: 41
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VLGATSSFLW CKLITVSGHA LLASIFWNRA KSVDLKSHQE ITSLYMFMWK    360
LFYAEYFIIP LMR                                                      373

SEQ ID NO: 42             moltype = AA  length = 373
FEATURE                   Location/Qualifiers
source                    1..373
                          mol_type = protein
                          organism = synthetic construct
VARIANT                   1
                          note = May or may not be present
SEQUENCE: 42
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVIATSSFLW CKLITVSGHA LLASIFWNRA KSVDLKSHQE ITSLYMFMWK    360
LFYAEYFIIP LMR                                                      373

SEQ ID NO: 43             moltype = AA  length = 373
FEATURE                   Location/Qualifiers
source                    1..373
                          mol_type = protein
                          organism = synthetic construct
VARIANT                   1
                          note = May or may not be present
SEQUENCE: 43
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSPFLW CKLITVSGHA LLASIFWNRA KSVDLKSHQE ITSLYMFMWK    360
LFYAEYFIIP LMR                                                      373

SEQ ID NO: 44             moltype = AA  length = 373
FEATURE                   Location/Qualifiers
source                    1..373
                          mol_type = protein
                          organism = synthetic construct
VARIANT                   1
                          note = May or may not be present
SEQUENCE: 44
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSIFLW CKLITVSGHA LLASIFWNRA KSVDLKSHQE ITSLYMFMWK    360
LFYAEYFIIP LMR                                                      373

SEQ ID NO: 45             moltype = AA  length = 373
FEATURE                   Location/Qualifiers
source                    1..373
                          mol_type = protein
                          organism = synthetic construct
VARIANT                   1
                          note = May or may not be present
SEQUENCE: 45
MTNASSNKTE KIKHEYANMR HRQHNLKHNY GGIEGVSTCE DWARNFVVNA ASGESLESHE    60
```

```
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSRLW CKLITVSGHA LLASIFWNRA KSVDLKSHQE ITSLYMFMWK    360
LFYAEYFIIP LMR                                                      373

SEQ ID NO: 46          moltype = AA  length = 373
FEATURE                Location/Qualifiers
source                 1..373
                       mol_type = protein
                       organism = synthetic construct
VARIANT                1
                       note = May or may not be present
SEQUENCE: 46
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSGLW CKLITVSGHA LLASIFWNRA KSVDLKSHQE ITSLYMFMWK    360
LFYAEYFIIP LMR                                                      373

SEQ ID NO: 47          moltype = AA  length = 373
FEATURE                Location/Qualifiers
source                 1..373
                       mol_type = protein
                       organism = synthetic construct
VARIANT                1
                       note = May or may not be present
SEQUENCE: 47
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFPW CKLITVSGHA LLASIFWNRA KSVDLKSHQE ITSLYMFMWK    360
LFYAEYFIIP LMR                                                      373

SEQ ID NO: 48          moltype = AA  length = 373
FEATURE                Location/Qualifiers
source                 1..373
                       mol_type = protein
                       organism = synthetic construct
VARIANT                1
                       note = May or may not be present
SEQUENCE: 48
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLD CKLITVSGHA LLASIFWNRA KSVDLKSHQE ITSLYMFMWK    360
LFYAEYFIIP LMR                                                      373

SEQ ID NO: 49          moltype = AA  length = 373
FEATURE                Location/Qualifiers
source                 1..373
                       mol_type = protein
                       organism = synthetic construct
VARIANT                1
                       note = May or may not be present
SEQUENCE: 49
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ    120
VIVTILSMNI YTAGINQLTD IEIDKINKPY LPLASGEYSY KTGVTIITLC AILSLGVGWI    180
VGSPPLFWSN FAYFVLGTVY SIDLPLMRWK SHPALAALFF FVIRGLTFHV GFFLHLQTHV    240
FKRPMMIPKS VMFGTAFMSF FYVIIAFFKD IPDIEGDKDH GVKSLTMRLG QERVFWICVS    300
LLLTGYGAAI VVGATSSFLW CKLIGVSGHA LLASIFWNRA KSVDLKSHQE ITSLYMFMWK    360
LFYAEYFIIP LMR                                                      373

SEQ ID NO: 50          moltype = AA  length = 373
FEATURE                Location/Qualifiers
source                 1..373
                       mol_type = protein
                       organism = synthetic construct
VARIANT                1
                       note = May or may not be present
SEQUENCE: 50
```

```
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KGVDLKSHQE ITSLYMFMWK   360
LFYAEYFIIP LMR                                                     373

SEQ ID NO: 51           moltype = AA  length = 373
FEATURE                 Location/Qualifiers
source                  1..373
                        mol_type = protein
                        organism = synthetic construct
VARIANT                 1
                        note = May or may not be present
SEQUENCE: 51
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSFYMFMWK   360
LFYAEYFIIP LMR                                                     373

SEQ ID NO: 52           moltype = AA  length = 8
FEATURE                 Location/Qualifiers
source                  1..8
                        mol_type = protein
                        organism = synthetic construct
SEQUENCE: 52
ACFGIMTV                                                             8

SEQ ID NO: 53           moltype = AA  length = 7
FEATURE                 Location/Qualifiers
source                  1..7
                        mol_type = protein
                        organism = synthetic construct
SEQUENCE: 53
CDEKPQS                                                              7

SEQ ID NO: 54           moltype = AA  length = 6
FEATURE                 Location/Qualifiers
source                  1..6
                        mol_type = protein
                        organism = synthetic construct
SEQUENCE: 54
AEMRST                                                               6

SEQ ID NO: 55           moltype = AA  length = 10
FEATURE                 Location/Qualifiers
source                  1..10
                        mol_type = protein
                        organism = synthetic construct
SEQUENCE: 55
FHIKLPQRWY                                                          10

SEQ ID NO: 56           moltype = AA  length = 373
FEATURE                 Location/Qualifiers
source                  1..373
                        mol_type = protein
                        organism = synthetic construct
VARIANT                 1
                        note = May or may not be present
SEQUENCE: 56
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRAK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 57           moltype = AA  length = 373
FEATURE                 Location/Qualifiers
source                  1..373
                        mol_type = protein
                        organism = synthetic construct
VARIANT                 1
                        note = May or may not be present
```

```
SEQUENCE: 57
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRNK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 58          moltype = AA   length = 373
FEATURE                Location/Qualifiers
source                 1..373
                       mol_type = protein
                       organism = synthetic construct
VARIANT                1
                       note = May or may not be present
SEQUENCE: 58
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRDK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 59          moltype = AA   length = 373
FEATURE                Location/Qualifiers
source                 1..373
                       mol_type = protein
                       organism = synthetic construct
VARIANT                1
                       note = May or may not be present
SEQUENCE: 59
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMREK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 60          moltype = AA   length = 373
FEATURE                Location/Qualifiers
source                 1..373
                       mol_type = protein
                       organism = synthetic construct
VARIANT                1
                       note = May or may not be present
SEQUENCE: 60
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRGK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 61          moltype = AA   length = 373
FEATURE                Location/Qualifiers
source                 1..373
                       mol_type = protein
                       organism = synthetic construct
VARIANT                1
                       note = May or may not be present
SEQUENCE: 61
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRHK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 62          moltype = AA   length = 373
FEATURE                Location/Qualifiers
source                 1..373
                       mol_type = protein
                       organism = synthetic construct
VARIANT                1
```

```
                              note = May or may not be present
SEQUENCE: 62
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRIK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 63              moltype = AA  length = 373
FEATURE                    Location/Qualifiers
source                     1..373
                           mol_type = protein
                           organism = synthetic construct
VARIANT                    1
                           note = May or may not be present
SEQUENCE: 63
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRLK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 64              moltype = AA  length = 373
FEATURE                    Location/Qualifiers
source                     1..373
                           mol_type = protein
                           organism = synthetic construct
VARIANT                    1
                           note = May or may not be present
SEQUENCE: 64
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRKK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 65              moltype = AA  length = 373
FEATURE                    Location/Qualifiers
source                     1..373
                           mol_type = protein
                           organism = synthetic construct
VARIANT                    1
                           note = May or may not be present
SEQUENCE: 65
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRFK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 66              moltype = AA  length = 373
FEATURE                    Location/Qualifiers
source                     1..373
                           mol_type = protein
                           organism = synthetic construct
VARIANT                    1
                           note = May or may not be present
SEQUENCE: 66
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRPK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 67              moltype = AA  length = 373
FEATURE                    Location/Qualifiers
source                     1..373
                           mol_type = protein
                           organism = synthetic construct
```

```
VARIANT                   1
                          note = May or may not be present
SEQUENCE: 67
MTNASSNKTE KIKHEYANMR HRQHNLKHNY GGIEGVSTCE DWARNFVVNA ASGFSLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRCK SHPALAALFF FVIRGLTFHV GFFLHLQTHV   240
FKRPMMIPKS VMFGTAFMSF FYVIIAFFKD IPDIEGDKKH GVKSLTVRLG QERVFWICVS   300
LLLTGYGAAI VLGATSSRLW CKLITVSGHA LLASIFWNRA KGVDLKSHQE ITSLYMFMWK   360
LFYAEYFIIP LMR                                                      373

SEQ ID NO: 68             moltype = AA  length = 373
FEATURE                   Location/Qualifiers
source                    1..373
                          mol_type = protein
                          organism = synthetic construct
VARIANT                   1
                          note = May or may not be present
SEQUENCE: 68
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLLYMRYK SHPALAALFF FVIRGLTFHV GFFLHLQTHV   240
FKRPMMIPKS VMFGTAFMSF FYVIIAFFKD IPDIEGDKDH GVKSLTVRLG QERVFWICVS   300
LLLTGYGAAI VLGATSSFLW CKLITVSGHA LLASIFWNRA KGVDLKSHQE ITSLYMFMWK   360
LFYAEYFIIP LMR                                                      373

SEQ ID NO: 69             moltype = AA  length = 373
FEATURE                   Location/Qualifiers
source                    1..373
                          mol_type = protein
                          organism = synthetic construct
VARIANT                   1
                          note = May or may not be present
SEQUENCE: 69
MTNASSNKTE KIKHEYANMR HRQHNLKHNY GGIEGVSTCE DWARNFVVNA ASGESLESHE    60
AQHHCPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPYMRIK SHPALAALFF FVIRGLTFHV GFFLHLQTHV   240
FKRPMMIPKS VMFGTAFMSF FYVIIAFFKD IPDIEGDKLH GVKSLTFRLG QERVFWICVS   300
LLLTGYGAAI VYGATSSFLW CKLITVSGHA LLASIFWNRA KSVDLKSHQG ITSFYMFMWK   360
LFYAEYFIIP LMR                                                      373

SEQ ID NO: 70             moltype = AA  length = 373
FEATURE                   Location/Qualifiers
source                    1..373
                          mol_type = protein
                          organism = synthetic construct
VARIANT                   1
                          note = May or may not be present
SEQUENCE: 70
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRVK SHPALAALFF FVIRGMTFHV GFFLHLQTHV   240
FKRPMMIPKS VMFGTAFMSF FYVIIAFFKD IPDIEGDKKH GVKSLTMRLG QERVFWICVS   300
LLLTGYGAAI VLGATSSFLW CKLITVSGHA LLASIFWNRA KGVDLKSHQE ITSFYMFMWK   360
LFYAEYFIIP LMR                                                      373

SEQ ID NO: 71             moltype = AA  length = 373
FEATURE                   Location/Qualifiers
source                    1..373
                          mol_type = protein
                          organism = synthetic construct
VARIANT                   1
                          note = May or may not be present
SEQUENCE: 71
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRWK SHPALAALFF FVIRGLTFHV GFFLHLQTHV   240
FKRPMMIPKS VMFGTAFMSF FYVIIAFFKD IPDIEGDKRH GVKSLTMRLG QERVFWICVS   300
LLLTGYGAAI VWGATSSFLW CKLITVSGHA LLASIFWNRA KSVDLKSHQE ITSFYMFMWK   360
LFYAEYFIIP LMR                                                      373

SEQ ID NO: 72             moltype = AA  length = 373
FEATURE                   Location/Qualifiers
source                    1..373
                          mol_type = protein
```

```
                              organism = synthetic construct
VARIANT                       1
                              note = May or may not be present
SEQUENCE: 72
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTGY SIDLLYMRVK SHPALAALFF FVIRGMTFHV GFFLHLQTHV   240
FKRPMMIPKS VMFGTAFMSF FYVIIAFFKD IPDLEGDKDH GVKSLTFRLG QERVFWICVS   300
LLLTGYGAAI VVIATSSRLW CKLIGVSGHA LLASIFWNRA KSVDLKSHQE ITSFYMFMWK   360
LFYAEYFIIP LMR                                                     373

SEQ ID NO: 73                 moltype = AA  length = 373
FEATURE                       Location/Qualifiers
source                        1..373
                              mol_type = protein
                              organism = synthetic construct
VARIANT                       1
                              note = May or may not be present
SEQUENCE: 73
MTNASSNKTE KIKHEYANMR HRQHNLKHNY GGIEGVSTCE DWARNFVVNA ASGFSLESHE    60
AQHHTPETLW GSIKQFCDAF YRFSRPHVII GTAVNIIVMS SLALEKSLDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTGY SIDLPYMRSK SHPALAALFF FVIRGLTFHV GFFLHLQTHV   240
FKRPMMIPKS VMFGTAFMSF FYVIIAFFRD IPDLEGDKMH GVKSLTVRLG QERVFWICVS   300
LLLTGYGAAI VFGATSIFLW CKLITVSGHA LLASIFWNRA KGVDLKSHQE ITSLYMFMWK   360
LFYAEYFIIP LMR                                                     373

SEQ ID NO: 74                 moltype = AA  length = 373
FEATURE                       Location/Qualifiers
source                        1..373
                              mol_type = protein
                              organism = synthetic construct
VARIANT                       1
                              note = May or may not be present
SEQUENCE: 74
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTGY SIDLLLMRWK SHPALAALFF FVIRGMTFHV GFFLHLQTHV   240
FKRPMMIPKS VMFGTAFMSF FYVIIAFFKD IPDIEGDKDH GVKSLTVRLG QERVFWICVS   300
LLLTGYGAAI VVGATSIRLW CKLITVSGHA LLASIFWNRA KGVDLKSHQE ITSLYMFMWK   360
LFYAEYFIIP LMR                                                     373

SEQ ID NO: 75                 moltype = AA  length = 373
FEATURE                       Location/Qualifiers
source                        1..373
                              mol_type = protein
                              organism = synthetic construct
VARIANT                       1
                              note = May or may not be present
SEQUENCE: 75
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSLDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTGY SIDLLYMRSK SHPALAALFF FVIRGLTFHV GFFQHLQTHV   240
FKRPMMIPKS VMFGTAFMSF FYVIIAFFKD IPDIEGDKRH GVKSLTMRLG QERVFWICVS   300
LLLTGYGAAI VFGATSSFLW CKLITVSGHA LLASIFWNRA KSVDLKSHQE ITSLYMFMWK   360
LFYAEYFIIP LMR                                                     373

SEQ ID NO: 76                 moltype = AA  length = 373
FEATURE                       Location/Qualifiers
source                        1..373
                              mol_type = protein
                              organism = synthetic construct
VARIANT                       1
                              note = May or may not be present
SEQUENCE: 76
MTNASSNKTE KIKHEYANMR HRQHNLKHNY GGIEGVSTCE DWARNFVVNA ASGESLESHE    60
AQHHTPETLW GSIKQFCDAF YRFSRPHVII GTAVNIIVMS SLALEKSLDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTGY SIDLLYMRSK SHPALAALFF FVIRGLTFHV GFFQHLQTHV   240
FKRPMMIPKS VMFGTAFMSF FYVIIAFFKD IPDIEGDKRH GVKSLTMRLG QERVFWICVS   300
LLLTGYGAAI VFGATSSFLW CKLITVSGHA LLASIFWNRA KSVDLKSHQE ITSLYMFMWK   360
LFYAEYFIIP LMR                                                     373

SEQ ID NO: 77                 moltype = AA  length = 373
FEATURE                       Location/Qualifiers
source                        1..373
```

```
                        mol_type = protein
                        organism = synthetic construct
VARIANT                 1
                        note = May or may not be present
SEQUENCE: 77
MTNASSNKTE KIKHEYANMR HRQHNLKHNY GGIEGVSTCE DWARNFVSNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPVLFWSN FAYFVLGTVY SIDLLLMRTK SHPALAALFF FVIRGLTFHV GFFLHLQTHV   240
FKRPMMIPKS VMFGTAFMSF FYVIIAFFKD IPDLEGDKMH GVKSLTFRLG QERVFWICVS   300
LLLTGYGAAI VCIATSSRLW CKLITVSGHA LLASIFWNRA KSVDLKSHQE ITSLYMFMWK   360
LFYAEYFIIP LMR                                                     373

SEQ ID NO: 78           moltype = AA   length = 373
FEATURE                 Location/Qualifiers
source                  1..373
                        mol_type = protein
                        organism = synthetic construct
VARIANT                 1
                        note = May or may not be present
SEQUENCE: 78
MTNASSNKTE KIKHEYANMR HRQHNLKHNY GGIEGVSTCE DWARNFVVNA ASGFSLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTVY SIDLPYMRWK SHPALAALFF FVIRGLTFHV GFFQHLQTHV   240
FKRPMMIPKS VMFGTAFMSF FYVIIAFFRD IPDLEGDKMH GVKSLTVRLG QERVFWICVS   300
LLLTGYGAAI VYGATSSFLW CKLITVSGHA LLASIFWNRA KGVDLKSHQE ITSFYMFMWK   360
LFYAEYFIIP LMR                                                     373

SEQ ID NO: 79           moltype = AA   length = 373
FEATURE                 Location/Qualifiers
source                  1..373
                        mol_type = protein
                        organism = synthetic construct
VARIANT                 1
                        note = May or may not be present
SEQUENCE: 79
MTNASSNKTE KIKHEYANMR HRQHNLKHNY GGIEGVSTCE DWARNFVVNA ASGESLESHE    60
AQHHTPETLW DSIKQFCDAF YRFSRPHVII GTAVNIIVMS SLALEKSLDI SPKFFIGLFQ   120
VIVTILSMNI YTAGINQLTD IEIDKINKPY LPLASGEYSY KHGVTIITLC AILSLGVGWI   180
VGSPVLFWSN FAYFVLGTGY SIDLLYMRSK SHPALAALFF FVIRGMTFHV GFFQHLQTHV   240
FKRPMMIPKS VMFGTAFMSF FYVIIAFFKD IPDLEGDKDH GVKSLTVRLG QERVFWICVS   300
LLLTGYGAAI VWGATSSRLW CKLITVSGHA LLASIFWNRA KSVDLKSHQE ITSLYMFMWK   360
LFYAEYFIIP LMR                                                     373

SEQ ID NO: 80           moltype = AA   length = 373
FEATURE                 Location/Qualifiers
source                  1..373
                        mol_type = protein
                        organism = synthetic construct
VARIANT                 1
                        note = May or may not be present
SEQUENCE: 80
MTNASSNKTE KIKHEYANMR HRQHNLKHNY GGIEGVSTCE DWARNFVSNA ASGESLESHE    60
AQHHTPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRCK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 81           moltype = AA   length = 373
FEATURE                 Location/Qualifiers
source                  1..373
                        mol_type = protein
                        organism = synthetic construct
VARIANT                 1
                        note = May or may not be present
SEQUENCE: 81
MTNASSNKTE KIKHEYANMR HRQHNLKHNY GGIEGVSTCE DWARNFVVNA ASGESLESHE    60
AQHHCPETLW GSIKQFCDAF YRFSRPHVII GTAVNIIVMS SLALEKSSDI SPKFFIGLFQ   120
VIVTILSMNI YTAGINQLTD IEIDKINKPY LPLASGEYSY KTGVTIITLC AILSLGVGWI   180
VGSPPLFWSN FAYFVLGTVY SIDLPLMRCK SHPALAALFF FVIRGLTFHV GFFLHLQTHV   240
FKRPMMIPKS VMFGTAFMSF FYVIIAFFKD IPDIEGDKDH GVKSLTMRLG QERVFWICVS   300
LLLTGYGAAI VVGATSSFLW CKLITVSGHA LLASIFWNRA KSVDLKSHQE ITSLYMFMWK   360
LFYAEYFIIP LMR                                                     373

SEQ ID NO: 82           moltype = AA   length = 90
FEATURE                 Location/Qualifiers
```

```
source                  1..90
                        mol_type = protein
                        organism = synthetic construct
VARIANT                 1
                        note = May or may not be present
SEQUENCE: 82
MASMFLGSLP LASSVNYIGR ITRSKNCTES YHATSYITNA SSNKTEKIKH EYANMRHRQH    60
NLKHNYGGIE GVSTCEDWAR NFVVNAASGE                                    90

SEQ ID NO: 83           moltype = AA  length = 42
FEATURE                 Location/Qualifiers
source                  1..42
                        mol_type = protein
                        organism = synthetic construct
VARIANT                 1
                        note = May or may not be present
SEQUENCE: 83
MHEYANMRHR QHNLKHNYGG IEGVSTCEDW ARNFVVNAAS GE                      42

SEQ ID NO: 84           moltype = AA  length = 132
FEATURE                 Location/Qualifiers
source                  1..132
                        mol_type = protein
                        organism = synthetic construct
VARIANT                 1
                        note = May or may not be present
SEQUENCE: 84
KRPMMIPKSV MFGTAFMSFF YVIIAFFKDI PDIEGDKDHG VKSLTMRLGQ ERVFWICVSL    60
LLTGYGAAIV VGATSSFLWC KLITVSGHAL LASIFWNRAK SVDLKSHQEI TSLYMFMWKL   120
FYAEYFIIPL MR                                                      132

SEQ ID NO: 85           moltype = AA  length = 132
FEATURE                 Location/Qualifiers
source                  1..132
                        mol_type = protein
                        organism = synthetic construct
VARIANT                 1
                        note = May or may not be present
SEQUENCE: 85
KRPMMIPKPV MFGTAFMSFF YVIIAFFKDI PDIEGDKDHG VKSLTMRLGQ KRVFWICVSL    60
LLTGYGAAIV VGATSSFLWC KLITVSGHAL LASIFWNRAK SVDLKSHQEI TSLYMFMWKL   120
FYAEYFIIPL MR                                                      132
```

ENGINEERED ENZYMES AND BIOPRODUCTION OF BAKUCHIOL

CROSS REFERENCE TO RELATED APPLICATIONS

This application claims priority under 35 U.S.C. § 119 to Provisional Application Ser. No. 63/316,855 filed Mar. 4, 2022, Provisional Application Ser. No. 63/316,859 filed Mar. 4, 2022, and Provisional Application Ser. No. 63/401,063 filed Aug. 25, 2022, the disclosures of which are incorporated herein by reference.

SEQUENCE LISTING

The instant application contains a Sequence Listing which has been submitted electronically in XML format and is hereby incorporated by reference in its entirety. Said XML copy, created on Jun. 7, 2024, is named 131881-0117_SL.xml and is 134,031 bytes in size.

BACKGROUND

The following discussion is merely provided to aid the reader in understanding the disclosure and is not admitted to describe or constitute prior art thereto.

Bakuchiol is terpenoid produced by a number of plants, including *Psoralea corylifolia, P. grandulosa, P. drupaceae, Ulmus davidiana, Otholobium pubescens, Piper longum,* and *Aerva sangulnolenta* Blum. However, the enzyme(s) and thus the exact synthesis process responsible for producing bakuchiol are unknown.

Bakuchiol is utilized for a variety of commercial, pharmaceutical, and cosmetic purposes due to its reported activities, such as anti-wrinkle, anti-acne, anti-inflammatory, anti-osteoporosis, ant-oxidant, anti-biofilm, and anti-cancer effects. Bakuchiol is also used in traditional Chinese medicine.

Though there have been previous attempts to chemically synthesize bakuchiol, the resulting synthesis schemes were difficult and inefficient. Instead, most bakuchiol used today is extracted from plants via laborious and expensive extraction procedures. To date, the lack of identification of enzymes capable of producing bakuchiol in large quantities has hindered bioproduction of bakuchiol in, for example, a transgenic host or bioreactor.

SUMMARY

The present disclosure provides examples generally related to synthetic biology and, in particular, engineered enzymes and bioproduction of bakuchiol. Some examples provided herein may be employed to overcome the pre-existing challenges and may have the benefit of identifying enzyme(s) capable of producing bakuchiol in larger quantities than previously possible, for the development of efficient bioproduction of bakuchiol.

The present disclosure provides examples of the proteins that produce bakuchiol through a mechanism involving GPP/DMAPP/IPP and p-coumaric acid. Based on the identification of these proteins, the present disclosure provides examples of nucleic acids encoding the disclosed proteins, transgenic cells that produce bakuchiol, methods of producing bakuchiol, bioproduction batches of bakuchiol, and methods of detecting bakuchiol.

In one aspect, the present disclosure provides an isolated protein comprising an amino acid sequence with at least about 65% identity to:

(SEQ ID NO: 1; BAK28)
MHEYANMRHRQHNLKHNYGGIEGVSTCEDWARNFVVNAASGESLESHEA
QHHTPETLWGSIKQFCDAFYRFSRPHVIIGTAVNIIVMSSLALEKSSDI
SPKFFIGLFQVIVTILSMNIYTAGINQLTDIEIDKINKPYLPLASGEYS
YKTGVTIITLCAILSLGVGWIVGSPPLFWSNFAYFVLGTVYSIDLPLMR
WKSHPALAALFFFVIRGLTFHVGFFLHLQTHVFKRPMMIPKPVMFGTAF
MSFFYVIIAFFKDIPDIEGDKDHGVKSLTMRLGQKRVFWICVSLLLTGY
GAAIVVGATSSFLWCKLITVSGHALLASIFWNRAKSVDLKSHQEITSLY
MFMWKLFYAEYFIIPLMR, or (SEQ ID NO: 2; BAK36)
MASMFLGSLPLASSVNYIGRITRSKNCTESYHATSYITNASSNKTEKIK
HEYANMRHRQHNLKHNYGGIEGVSTCEDWARNFVVNAASGESLESHEAQ
HHTPETLWGSIKQFCDAFYRFSRPHVIIGTAVNIIVMSSLALEKSSDIS
PKFFIGLFQVIVTILSMNIYTAGINQLTDIEIDKINKPYLPLASGEYSY
KTGVTIITLCAILSLGVGWIVGSPPLFWSNFAYFVLGTVYSIDLPLMRW
KSHPALAALFFFVIRGLTFHVGFFLHLQTHVFKRPMMIPKSVMFGTAFM
SFFYVIIAFFKDIPDIEGDKDHGVKSLTMRLGQERVFWICVSLLLTGYG
AAIVVGATSSFLWCKLITVSGHALLASIFWNRAKSVDLKSHQEITSLYM
FMWKLFYAEYFIIPLMR.

The isolated protein can comprise an amino acid sequence comprising at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity with SEQ ID NO: 1 or SEQ ID NO: 2.

The isolated protein may additionally comprise an N-terminal deletion of 1 to about 73 amino acids or 1 to about 120 amino acids. The isolated protein generally catalyzes the production of bakuchiol, exhibits prenyltransferase activity, or both.

In another aspect, the present disclosure provides a transgenic cell, comprising a transgene encoding the protein of the foregoing aspect. The transgenic cell may be prokaryotic, such as *Escherichia coli* (*E. coli*), an *Acinetobacter* species, a *Pseudomonas* species, a *Streptomyces* species, or a *Mycobacterium* species. Alternatively, the transgenic cell may be eukaryotic, such as *Saccharomyces cerevisiae* (*S. cerevisiae*) or other yeast species, a filamentous fungi, an algae, or an amoeba.

In another aspect, the present disclosure provides a method of producing bakuchiol, comprising culturing the transgenic cell according to the foregoing aspect in a culture medium comprising p-coumaric acid and (i) geranyl pyrophosphate (GPP), (ii) dimethylallyl pyrophosphate (DMAPP), (iii) isopentenyl pyrophosphate (IPP), or any combination of (i)-(iii).

In another aspect, the disclosure provides a transgenic cell, comprising a transgene encoding a transgenic protein comprising an amino acid sequence with at least about 65% identity to SEQ ID NO: 1 (BAK28), or SEQ ID NO: 2 (BAK36). In general, the transgenic protein is capable of catalyzing the production of bakuchiol, exhibits prenyltransferase activity, or both.

The transgenic protein can comprise an amino acid sequence with at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1 or SEQ ID NO: 2.

The transgenic cell can be prokaryotic. For example, the transgenic cell can be selected from *Escherichia coli* (*E.* coli), an *Acinetobacter* species, a *Pseudomonas* species, a *Streptomyces* species, and a *Mycobacterium* species.

The transgenic cell can be eukaryotic. For example, the transgenic cell can be selected from *Saccharomyces cerevisiae* (*S. cerevisiae*) or other yeast species, a filamentous fungi, an algae, and an amoeba. In some implementations, the filamentous fungi can be selected from an *Aspergillus* species and a *Trichoderma* species. In some implementations, the amoeba can be *Dictyostelium discoideum*. In some implementations, the algae can be selected from *Botryococcus braunii, Chlorella* sp., *Crypthecodinium cohnii, Cylindrotheca* sp., *Nitzschia* sp., *Phaeodactylum tricornutum, Schizochytrium* sp., and *Tetraselmis suecia*.

Bakuchiol can be produced when the transgenic cell is cultured in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

The transgenic cell may produce at least about 0.1 μg/L, at least about 0.2 μg/L, at least about 0.3 μg/L, at least about 0.4 μg/L, at least about 0.5 μg/L, at least about 0.6 μg/L, at least about 0.7 μg/L, at least about 0.8 μg/L, at least about 0.9 μg/L, at least about 1.0 μg/L, at least about 1.1 μg/L, at least about 1.2 μg/L, at least about 1.3 μg/L, at least about 1.4 μg/L, at least about 1.5 μg/L, at least about 1.6 μg/L, at least about 1.7 μg/L, at least about 1.8 μg/L, at least about 1.9 μg/L, at least about 2.0 μg/L, at least about 2.1 μg/L, at least about 2.2 μg/L, at least about 2.3 μg/L, at least about 2.4 μg/L, at least about 2.5 μg/L, at least about 3.0 μg/L, at least about 4.0 μg/L, at least about 5.0 μg/L, at least about 10.0 μg/L, at least about 15.0 μg/L, at least about 20.0 μg/L, at least about 25.0 μg/L, at least about 30.0 μg/L, at least about 35.0 μg/L, at least about 40.0 μg/L, at least about 45.0 μg/L, at least about 50.0 μg/L, at least about 100.0 μg/L, at least about 150.0 μg/L, at least about 200.0 μg/L, at least about 250.0 μg/L, at least about 300.0 μg/L, at least about 350.0 μg/L, at least about 400.0 μg/L, at least about 450.0 μg/L, at least about 500.0 μg/L, at least about 600.0 μg/L, at least about 700.0 μg/L, at least about 800.0 μg/L, at least about 900.0 μg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours when cultured in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

In some implementations, the transgene is integrated into the transgenic cell's genome. In some implementations, the transgene is not integrated into the transgenic cell's genome.

In some implementations, expression of the transgene can be driven by a GAL 1 promoter. In some implementations, expression of the transgene is driven by an inducible promoter.

The transgenic protein can have at least about 90% identity to SEQ ID NO: 1 or SEQ ID NO: 2. The transgenic protein can comprise SEQ ID NO: 1 or SEQ ID NO: 2. The transgenic protein can consists of SEQ ID NO: 1 or SEQ ID NO: 2.

In another aspect, the present disclosure provides methods of producing bakuchiol, comprising culturing a transgenic cell disclosed here (e.g., described in the foregoing aspect) in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

The culture medium can further comprise about 3% w/v maltodextrin, about 0.2% w/v glucose, alpha-amylase, or any combination thereof.

In some implementations, the culture medium can comprises at least about 1.50 mM p-coumaric acid, at least about 1.75 mM p-coumaric acid, at least about 2.00 p-coumaric acid, at least about 2.25 mM p-coumaric acid, at least about 2.50 mM p-coumaric acid, at least about 2.75 mM p-coumaric acid, at least about 3.00 p-coumaric acid, at least about 3.25 mM p-coumaric acid, at least about 3.50 mM p-coumaric acid, at least about 3.75 mM p-coumaric acid, at least about 4.00 p-coumaric acid or more. In some implementations, the culture medium does not comprise exogenous p-coumaric acid, GPP, DMAPP, IPP, or a combination thereof.

In some implementations, at least about 0.1 μg/L, at least about 0.2 μg/L, at least about 0.3 μg/L, at least about 0.4 μg/L, at least about 0.5 μg/L, at least about 0.6 μg/L, at least about 0.7 μg/L, at least about 0.8 μg/L, at least about 0.9 μg/L, at least about 1.0 μg/L, at least about 1.1 μg/L, at least about 1.2 μg/L, at least about 1.3 μg/L, at least about 1.4 μg/L, at least about 1.5 μg/L, at least about 1.6 μg/L, at least about 1.7 μg/L, at least about 1.8 μg/L, at least about 1.9 μg/L, at least about 2.0 μg/L, at least about 2.1 μg/L, at least about 2.2 μg/L, at least about 2.3 μg/L, at least about 2.4 μg/L, at least about 2.5 μg/L, at least about 3.0 μg/L, at least about 4.0 μg/L, at least about 5.0 μg/L, at least about 10.0 μg/L, at least about 15.0 μg/L, at least about 20.0 μg/L, at least about 25.0 μg/L, at least about 30.0 μg/L, at least about 35.0 μg/L, at least about 40.0 μg/L, at least about 45.0 μg/L, at least about 50.0 μg/L, at least about 100.0 μg/L, at least about 150.0 μg/L, at least about 200.0 μg/L, at least about 250.0 μg/L, at least about 300.0 μg/L, at least about 350.0 μg/L, at least about 400.0 μg/L, at least about 450.0 μg/L, at least about 500.0 μg/L, at least about 600.0 μg/L, at least about 700.0 μg/L, at least about 800.0 μg/L, at least about 900.0 μg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours of culture.

In another aspect, the present disclosure provides bioproduction batches of bakuchiol, wherein the bakuchiol has a chemical purity of at least about 90%, at least about 91%, at least about 92%, at least about 93%, at least about 94%, at least about 95%, at least about 96%, at least about 97%, at least about 98%, at least about 99%, or 100%, and no single impurity of greater than about 1%.

A bioproduction batch of bakuchiol of the present disclosure can be produced by the disclosed bioproduction methods (e.g., the methods of the forgoing aspect).

In another aspect, the present disclosure provides isolated proteins comprising an amino acid sequence with at least about 65% identity to SEQ ID NO: 1 (BAK28), or SEQ ID NO: 2 (BAK36). In general, the isolated protein is capable of catalyzing the production of bakuchiol, exhibits prenyltransferase activity, or both.

The amino acid sequence of the isolated protein can comprise at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity with SEQ ID NO: 1 or SEQ ID NO: 2. The amino acid sequence can have at least 90% identity to SEQ ID NO: 1 or SEQ ID NO: 2. The amino acid sequence can comprise SEQ ID NO: 1 or SEQ ID NO: 2. The amino acid sequence can consists of SEQ ID NO: 1 or SEQ ID NO: 2.

The isolated protein can exhibit prenyltransferase activity, the isolated protein can catalyze the production of bakuchiol, or both.

In another aspect, the present disclosure provides nucleic acids comprising a nucleic acid sequence encoding any isolated protein disclosed herein (e.g., the isolated proteins of the foregoing aspect).

In another aspect, the present disclosure provides isolated host cells that produces an isolated protein disclosed herein or that comprises a nucleic acid disclosed herein (e.g., the isolated proteins or nucleic acids of the foregoing aspects).

In another aspect, the disclosure provides methods for determining an amount of bakuchiol in a sample, the method comprising: (i) ionizing bakuchiol from the sample to generate one or more ions detectable by mass spectrometry; (ii) determining an amount of bakuchiol ions by multiple reaction or high resolution accurate mass spectrometry; and (iii) relating the amount of bakuchiol ions to the amount of bakuchiol in the sample, wherein a limit of detection of the method for bakuchiol is between about 0.001 µg/L and 0.0001 µg/L.

In another aspect, the present disclosure provides methods of producing bakuchiol, comprising: (a) culturing a transgenic cell comprising a transgene encoding a transgenic bakuchiol-producing enzyme in a culture medium comprising p-coumaric acid and (i) geranyl pyrophosphate (GPP), (ii) dimethylallyl pyrophosphate (DMAPP), (iii) isopentenyl pyrophosphate (IPP), or any combination of (i)-(iii); (b) isolating bakuchiol from the culture medium; and (c) determining an amount of bakuchiol isolated from the culture medium by mass spectrometry, wherein determining comprises: (i) ionizing bakuchiol from the sample to generate one or more ions detectable by mass spectrometry; (ii) determining an amount of bakuchiol ions by multiple reaction or high resolution accurate mass spectrometry; and (iii) relating the amount of bakuchiol ions to the amount of bakuchiol in the sample, wherein a limit of detection of the method for bakuchiol is between about 0.001 µg/L and 0.0001 µg/L. The transgenic cell can be prokaryotic, and the prokaryotic cell can be selected from *Escherichia coli* (*E. coli*), an *Acinetobacter* species, a *Pseudomonas* species, a *Streptomyces* species, and a *Mycobacterium* species. The transgenic cell can be eukaryotic, and the eukaryotic cell can be selected from *Saccharomyces cerevisiae* (*S. cerevisiae*) or other yeast species, a filamentous fungi, an algae, and an amoeba. In some implementations, the filamentous fungi is selected from an *Aspergillus* species and a *Trichoderma* species. In some implementations, the amoeba is *Dictyostelium discoideum*. In some implementations, the algae is selected from *Botryococcus braunii*, *Chlorella* sp., *Crypthecodinium cohnii*, *Cylindrotheca* sp., *Nitzschia* sp., *Phaeodactylum tricornutum*, *Schizochytrium* sp., and *Tetraselmis suecia*. The transgene can integrated into the transgenic cell's genome, or the transgene may not integrated into the transgenic cell's genome.

Ionizing can comprise atmospheric pressure chemical ionization (APCI), which may be performed in negative ionization mode or positive ionization mode.

Ionizing can also comprise electrospray ionization (ESI), which may be performed in negative ionization mode or positive ionization mode. In some implementations, the one or more ions comprise an ion with a mass to charge ratio (m/z) of 172.1±0.5 or a parent ion with a mass to charge ratio (m/z) of about 255 in negative mode or about 257 in positive mode.

For the purposes of the disclosed methods prior to ionizing via APCI or ESI, the sample can be subjected to liquid chromatography, such as high performance liquid chromatography (HPLC), ultra performance liquid chromatography (UPLC), ultra high performance liquid chromatography (UHPLC), and supercritical fluid chromatography (SFC).

Ionizing can also comprise electron impact (EI) ionization.

For the purposes of the disclosed methods prior to ionizing via APCI or EI, the sample can be subjected to gas chromatography (GC).

For the purposes of the disclosed methods prior to ionizing, the sample can be diluted with an alcohol, extracted, centrifuged, or any combination thereof.

For the purposes of the disclosed, the sample can be obtained from a bioproduction batch of bakuchiol. The bakuchiol in the batch can have a chemical purity of at least about 90%, at least about 91%, at least about 92%, at least about 93%, at least about 94%, at least about 95%, at least about 96%, at least about 97%, at least about 98%, at least about 99%, or 100%, and no single impurity of greater than about 1%. The bakuchiol batch can be in the form of an oil or an aqueous solution. The concentration of bakuchiol in the bakuchiol batch can be at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more.

For the purposes of the disclosed methods, the bakuchiol can be produced by culturing a transgenic cell expressing a bakuchiol-producing enzyme in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii). The culture medium can further comprise about 3% w/v maltodextrin, about 0.2% w/v glucose, alpha-amylase, or any combination thereof. In some implementations, the culture medium can comprise at least about 1.50 mM p-coumaric acid, at least about 1.75 mM p-coumaric acid, at least about 2.00 p-coumaric acid, at least about 2.25 mM p-coumaric acid, at least about 2.50 mM p-coumaric acid, at least about 2.75 mM p-coumaric acid, at least about 3.00 p-coumaric acid, at least about 3.25 mM p-coumaric acid, at least about 3.50 mM p-coumaric acid, at least about 3.75 mM p-coumaric acid, at least about 4.00 p-coumaric acid or more. In some implementations, the culture medium is not supplemented with p-coumaric acid, GPP, DMAPP, IPP, or a combination thereof. In some implementations, at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours of culture.

In another aspect, the present disclosure provides engineered enzymes comprising an N-terminal deletion of: 1 to about 73 amino acids from the N-terminus of SEQ ID NO: 1; BAK28), or 1 to about 120 amino acids from the N-terminus of SEQ ID NO: 2 (BAK36).

In some implementations, the enzyme comprises an N-terminal deletion of 29, 57, or 73 amino acids from the N-terminus of SEQ ID NO: 1.

In some implementations, the enzyme comprises an N-terminal deletion of 38, 88, 105, or 120 amino acids from the N-terminus of SEQ ID NO: 2.

In some implementations, the enzyme comprises an amino acid sequence having at least about 80%, at least about 85%, at least about 90%, at least about 95%, or 100% identity to the amino acid sequence set forth in SEQ ID NO: 3. In some implementations, the engineered enzyme comprises at least one amino acid substitution at position 54, 71, 108, 162, 185, 199, 205, 206, 209, 226, 234, 257, 269, 274, 279, 287, 310, 312, 313, 317, 318, 319, 320, 325, 342, and 354 of SEQ ID NO: 3. In some implementations, the enzyme comprises at least one amino acid substitution, relative to SEQ ID NO: 3, selected from the group consisting of E54F, G71D, S108L, T162H, P185V, V199G, P205L, P205V, L206Y, W209S, W209C, W209V, W209T, W209Y, W209R, W209M, W209Q, W209A, W209N, W209D, W209E, W209G, W209H, W209I, W209L, W209K, W209F, W209P, L226M, L234Q, F257E, K269R, I274L, D279C, D279K, D279R, D279M, D279L, M287V, M287F, M287Y, I310V, V312W, V312A, V312F, V312G, V312Y, V312C, V312L, G313I, S317P, S317I, F318R, F318G, L319P, W320D, T325G, S342G, and L354F.

In some implementations, the enzyme comprises an amino acid sequence having at least 80%, at least 85%, at least 95%, or 100% identity to an amino acid sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 78, SEQ ID NO: 79, SEQ ID NO: 80, and SEQ ID NO: 81.

In another aspect, the present disclosure provides engineered bakuchiol-producing enzymes, comprising an N-terminal deletion of 1 to about 120 amino acids from the N-terminus of the enzyme, wherein the enzyme catalyzes production of bakuchiol, exhibits prenyltransferase activity, or both.

In some implementations, the enzyme comprises an amino acid sequence with at least about 65% identity to SEQ ID NO: 1 or SEQ ID NO: 2.

In some implementations, the N-terminal deletion increases catalyzation of production of bakuchiol, prenyltransferase activity, or both, relative to a non-engineered enzyme comprising a same amino acid sequence but without the N-terminal deletion.

In some implementations, the enzyme comprises an N-terminal deletion of 29, 57, or 73 amino acids from the N-terminus of SEQ ID NO: 1. In some implementations, the enzyme comprises an N-terminal deletion of 39, 88, 105, or 120 amino acids from the N-terminus of SEQ ID NO: 2.

In some implementations, the enzyme comprises an amino acid sequence with at least about 65% identity to SEQ ID NO: 3. In some implementations, the engineered enzyme comprises at least one amino acid substitution, relative to SEQ ID NO: 3, at position 54, 71, 108, 162, 185, 199, 205, 206, 209, 226, 234, 257, 269, 274, 279, 287, 310, 312, 313, 317, 318, 319, 320, 325, 342, or 354. In some implementations, the enzyme comprises at least one amino acid substitution, relative to SEQ ID NO: 3, selected from the group consisting of E54F, G71D, S108L, T162H, P185V, V199G, P205L, P205V, L206Y, W209S, W209C, W209V, W209T, W209Y, W209R, W209M, W209Q, W209A, W209N, W209D, W209E, W209G, W209H, W209I, W209L, W209K, W209F, W209P, L226M, L234Q, F257E, K269R, I274L, D279C, D279K, D279R, D279M, D279L, M287V, M287F, M287Y, I310V, V312W, V312A, V312F, V312G, V312Y, V312C, V312L, G313I, S317P, S317I, F318R, F318G, L319P, W320D, T325G, S342G, and L354F.

In some implementations, the enzyme comprises an amino acid sequence having at least 80%, at least 85%, at least 95%, or 100% identity to an amino acid sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 78, SEQ ID NO: 79, SEQ ID NO: 80, and SEQ ID NO: 81.

In another aspect, the present disclosure provides engineered enzymes comprising an amino acid sequence that is a variant of SEQ ID NO: 1, wherein the amino acid sequence comprises at least one substitution mutation relative to SEQ ID NO: 1 at one or more amino acid positions selected from 42, 59, 96, 150, 173, 187, 193, 194 197, 214, 222, 245, 257, 262, 267, 275, 298, 300, 301, 305, 306, 307, 308, 313, 330, and 342.

In another aspect, the present disclosure provides engineered enzymes comprising an amino acid sequence that is a variant of SEQ ID NO: 2, wherein the amino acid sequence comprises at least one substitution mutation relative to SEQ ID NO: 2 at one or more amino acid positions selected from 90, 107, 144, 198, 221, 235, 241, 242, 245, 262, 270, 293, 305, 310, 315, 323, 346, 348, 349, 353, 354, 355, 356, 361, 378, and 390.

In another aspect, the present disclosure provides engineered enzymes that catalyze production of bakuchiol, exhibits prenyltransferase activity, or both, wherein the engineered enzyme comprises at least one substitution mutation selected from:
  (a) substitution of a glutamate (E) corresponding to the E at position 42 of SEQ ID NO: 1 or position 90 of SEQ ID NO: 2;
  (b) substitution of a glycine (G) corresponding to the G at position 59 of SEQ ID NO: 1 or position 107 of SEQ ID NO: 2;
  (c) substitution of a serine (S) corresponding to the S at position 96 of SEQ ID NO: 1 or position 144 of SEQ ID NO: 2;
  (d) substitution of threonine (T) corresponding to the T at position 150 of SEQ ID NO: 1 or position 198 of SEQ ID NO: 2;
  (e) substitution of proline (P) corresponding to the P at position 173 of SEQ ID NO: 1 or position 221 of SEQ ID NO: 2;
  (f) substitution of valine (V) corresponding to the V at position 187 of SEQ ID NO: 1 or position 235 of SEQ ID NO: 2;
  (g) substitution of proline (P) corresponding to the P at position 193 of SEQ ID NO: 1 or position 241 of SEQ ID NO: 2;
  (h) substitution of leucine (L) corresponding to the L at position 194 of SEQ ID NO: 1 or position 242 of SEQ ID NO: 2;
  (i) substitution of tryptophan (W) corresponding to the W at position 197 of SEQ ID NO: 1 or position 245 of SEQ ID NO: 2;
  (j) substitution of leucine (L) corresponding to the L at position 214 of SEQ ID NO: 1 or position 262 of SEQ ID NO: 2;
  (k) substitution of leucine (L) corresponding to the L at position 222 of SEQ ID NO: 1 or position 270 of SEQ ID NO: 2;
  (l) substitution of phenylalanine (F) corresponding to the F at position 245 of SEQ ID NO: 1 or position 293 of SEQ ID NO: 2;
  (m) substitution of lysine (K) corresponding to the K at position 257 of SEQ ID NO: 1 or position 305 of SEQ ID NO: 2;
  (n) substitution of isoleucine (I) corresponding to the I at position 262 of SEQ ID NO: 1 or position 310 of SEQ ID NO: 2;
  (o) substitution of aspartic acid (D) corresponding to the D at position 267 of SEQ ID NO: 1 or position 315 of SEQ ID NO: 2;
  (p) substitution of methionine (M) corresponding to the M at position 275 of SEQ ID NO: 1 or position 323 of SEQ ID NO: 2;
  (q) substitution of isoleucine (I) corresponding to the I at position 298 of SEQ ID NO: 1 or position 346 of SEQ ID NO: 2;
  (r) substitution of valine (V) corresponding to the V at position 300 of SEQ ID NO: 1 or position 348 of SEQ ID NO: 2;
  (s) substitution of glycine (G) corresponding to the G at position 301 of SEQ ID NO: 1 or position 349 of SEQ ID NO: 2;
  (t) substitution of serine (S) corresponding to the S at position 305 of SEQ ID NO: 1 or position 353 of SEQ ID NO: 2;
  (u) substitution of phenylalanine (F) corresponding to the F at position 306 of SEQ ID NO: 1 or position 354 of SEQ ID NO: 2;
  (v) substitution of leucine (L) corresponding to the L at position 307 of SEQ ID NO: 1 or position 355 of SEQ ID NO: 2;
  (w) substitution of tryptophan (W) corresponding to the W at position 308 of SEQ ID NO: 1 or position 356 of SEQ ID NO: 2;
  (x) substitution of threonine (T) corresponding to the T at position 313 of SEQ ID NO: 1 or position 361 of SEQ ID NO: 2;
  (y) substitution of serine (S) corresponding to the S at position 330 of SEQ ID NO: 1 or position 378 of SEQ ID NO: 2; and
  (z) substitution of leucine (L) corresponding to the L at position 342 of SEQ ID NO: 1 or position 390 of SEQ ID NO: 2.

In another aspect, the present disclosure provides engineered enzymes that catalyze production of bakuchiol, exhibits prenyltransferase activity, or both, wherein the engineered enzyme comprises at least one substitution mutation selected from:

(a) substitution of phenylalanine (F) at position 42 of SEQ ID NO: 1 or position 90 of SEQ ID NO: 2;
(b) substitution of aspartate (D) at position 59 of SEQ ID NO: 1 or position 107 of SEQ ID NO: 2;
(c) substitution of leucine (L) at position 96 of SEQ ID NO: 1 or position 144 of SEQ ID NO: 2;
(d) substitution of histidine (H) at position 150 of SEQ ID NO: 1 or position 198 of SEQ ID NO: 2;
(e) substitution of valine (V) at position 173 of SEQ ID NO: 1 or position 221 of SEQ ID NO: 2;
(f) substitution of glycine (G) at position 187 of SEQ ID NO: 1 or position 235 of SEQ ID NO: 2;
(g) substitution of leucine (L) or valine (V) at position 193 of SEQ ID NO: 1 or position 241 of SEQ ID NO: 2;
(h) substitution of tyrosine (Y) at position 194 of SEQ ID NO: 1 or position 242 of SEQ ID NO: 2;
(i) substitution of serine (S), cysteine (C), valine (V), threonine (T), tyrosine (Y), arginine (R), methionine (M), or glutamine (Q) at position 197 of SEQ ID NO: 1 or position 245 of SEQ ID NO: 2;
(j) substitution of methionine (M) at position 214 of SEQ ID NO: 1 or position 262 of SEQ ID NO: 2;
(k) substitution of glutamine (Q) at position 222 of SEQ ID NO: 1 or position 270 of SEQ ID NO: 2;
(l) substitution of glutamate (E) at position 245 of SEQ ID NO: 1 or position 293 of SEQ ID NO: 2;
(m) substitution of arginine (R) at position 257 of SEQ ID NO: 1 or position 305 of SEQ ID NO: 2;
(n) substitution of leucine (L) at position 262 of SEQ ID NO: 1 or position 310 of SEQ ID NO: 2;
(o) substitution of cysteine (C), lysine (K), arginine (R), methionine (M), or leucine (L) at position 267 of SEQ ID NO: 1 or position 315 of SEQ ID NO: 2;
(p) substitution of valine (V), phenylalanine (F), or tyrosine (Y) at position 275 of SEQ ID NO: 1 or position 323 of SEQ ID NO: 2;
(q) substitution of valine (V) at position 298 of SEQ ID NO: 1 or position 346 of SEQ ID NO: 2;
(r) substitution of tryptophan (W), alanine (A), phenylalanine (F), glycine (G), tyrosine (Y), cysteine (C), or leucine (L) at position 300 of SEQ ID NO: 1 or position 348 of SEQ ID NO: 2;
(s) substitution of isoleucine (I) at position 301 of SEQ ID NO: 1 or position 349 of SEQ ID NO: 2;
(t) substitution of proline (P) or isoleucine (I) at position 305 of SEQ ID NO: 1 or position 353 of SEQ ID NO: 2;
(u) substitution of arginine (R) or glycine (G) at position 306 of SEQ ID NO: 1 or position 354 of SEQ ID NO: 2;
(v) substitution of proline (P) at position 307 of SEQ ID NO: 1 or position 355 of SEQ ID NO: 2;
(w) substitution of aspartate (D) at position 308 of SEQ ID NO: 1 or position 356 of SEQ ID NO: 2;
(x) substitution of glycine (G) at position 313 of SEQ ID NO: 1 or position 361 of SEQ ID NO: 2;
(y) substitution of glycine (G) at position 330 of SEQ ID NO: 1 or position 378 of SEQ ID NO: 2; and
(z) substitution of phenylalanine (F) at position 342 of SEQ ID NO: 1 or position 390 of SEQ ID NO: 2.

In some implementations, a substitution mutation in the disclosed engineered enzymes increases catalyzation of production of bakuchiol, prenyltransferase activity, or both, relative to a non-engineered enzyme comprising the same amino acid sequence but without the substitution mutation.

In some implementations, the disclosed engineered enzymes may further comprise an N-terminal deletion of 1-120 amino acids.

In another aspect, the present disclosure provides engineered enzymes, comprising an amino acid sequence that is a variant of

```
                                              (SEQ ID NO: 3)
MTNASSNKTEKIKHEYANMRHRQHNLKHNYGGIEGVSTCEDWARNFVVN

AASGESLESHEAQHHTPETLWGSIKQFCDAFYRFSRPHVIIGTAVNIIV

MSSLALEKSSDISPKFFIGLFQVIVTILSMNIYTAGINQLTDIEIDKIN

KPYLPLASGEYSYKTGVTIITLCAILSLGVGWIVGSPPLFWSNFAYFVL

GTVYSIDLPLMRWKSHPALAALFFFVIRGLTFHVGFFLHLQTHVFKRPM

MIPKSVMFGTAFMSFFYVIIAFFKDIPDIEGDKDHGVKSLTMRLGQERV

FWICVSLLLTGYGAAIVVGATSSFLWCKLITVSGHALLASIFWNRAKSV

DLKSHQEITSLYMFMWKLFYAEYFIIPLMR,
``` wherein the amino acid sequence comprises at least one substitution mutation relative to SEQ ID NO: 3 at one or more amino acid positions selected from 54, 71, 108, 162, 185, 199, 205, 206, 209, 226, 234, 257, 269, 274, 279, 287, 310, 312, 313, 317, 318, 319, 320, 325, 342, and 354.

In another aspect, the present disclosure provides engineered enzymes that catalyze production of bakuchiol, exhibits prenyltransferase activity, or both, the enzyme comprising nine transmembrane domains and loops connecting the transmembrane domains, wherein the enzyme comprises at least one substitution mutation on an internal loop or an external loop of the enzyme.

In some implementations, the enzyme comprises an N-terminus and a C-terminus, and no amino acids are substituted in the first 50 amino acids of the N-terminus or the terminal 50 amino acids of the C-terminus.

In some implementations, the substitution mutation increases catalyzation of production of bakuchiol, prenyltransferase activity, or both, relative to a non-engineered enzyme comprising the same amino acid sequence but without the substitution mutation.

In another aspect, the present disclosure provides transgenic cells, comprising a transgene encoding an engineered enzyme disclosed herein.

In some implementations, the transgenic cell is prokaryotic. In some implementations, the transgenic cell is selected from *Escherichia coli* (*E. coli*), an *Acinetobacter* species, a *Pseudomonas* species, a *Streptomyces* species, a *Bacillus* species, and a *Mycobacterium* species.

In some implementations, the transgenic cell is eukaryotic. In some implementations, the transgenic cell is selected from a yeast species, a filamentous fungus, an algae, and an amoeba. In some implementations, the filamentous fungus is selected from an *Aspergillus* species and a *Trichoderma* species. In some implementations, the amoeba is *Dictyostelium discoideum*. In some implementations, the algae is selected from *Botryococcus braunii, Chlorella* sp., *Crypthecodinium cohnii, Cylindrotheca* sp., *Nitzschia* sp., *Phaeodactylum tricornutum, Schizochytrium* sp., and *Tetraselmis suecia*. In some implementations, the yeast species is *Saccharomyces cerevisiae* (*S. cerevisiae*), *Pichia pastoris*, or *Kluyveromyces marxianus*. In some implementations, the yeast species is an oleaginous yeast.

In some implementations, the transgene is integrated into the transgenic cell's genome. In some implementations, the transgene is not integrated into the transgenic cell's genome.

In some implementations, the engineered enzyme comprises an amino acid sequence selected from any one of SEQ ID NOs: 1-51 and 56-81. In some implementations, the engineered enzyme has an amino acid sequence consisting of any one of SEQ ID NOs: 1-51 and 56-81.

In another aspect, the present disclosure provides methods of producing bakuchiol, comprising culturing the transgenic cell disclosed herein in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

In another aspect, the present disclosure provides a bioproduction batch of bakuchiol produced by the methods disclosed herein.

In another aspect, the present disclosure provides a nucleic acid comprising a nucleic acid sequence encoding an engineered enzyme disclosed herein.

In another aspect, the present disclosure provides an engineered host cell that produces an engineered enzyme disclosed herein or that comprises a nucleic acid disclosed herein.

In another aspect, the present disclosure provides a bakuchiol-producing enzyme as disclosed herein. In another aspect, the present disclosure provides a transgenic cell capable of producing bakuchiol as disclosed herein. In another aspect, the present disclosure provides a method of producing bakuchiol as disclosed herein.

The foregoing general description and following detailed description are examples and are intended to provide further explanation of the disclosure as claimed. Other objects, advantages, and novel features will be readily apparent to those skilled in the art from the following brief description of the drawings and detailed description of the disclosure.

It should be appreciated that all combinations of the foregoing concepts and additional concepts discussed in greater detail below are provided as being part of the inventive subject matter disclosed herein and may be employed in any combination to achieve the benefits described herein.

BRIEF DESCRIPTION OF DRAWINGS

FIG. 5 (FIG. 5) shows, in one implementation, the predicted transmembrane regions of BAK28 and BAK36.

FIG. 7 (FIG. 7) shows, in one implementation, the results of a Blast search for homologs of BAK28 and BAK36 in the NCBI database.

DETAILED DESCRIPTION

Figure 1:
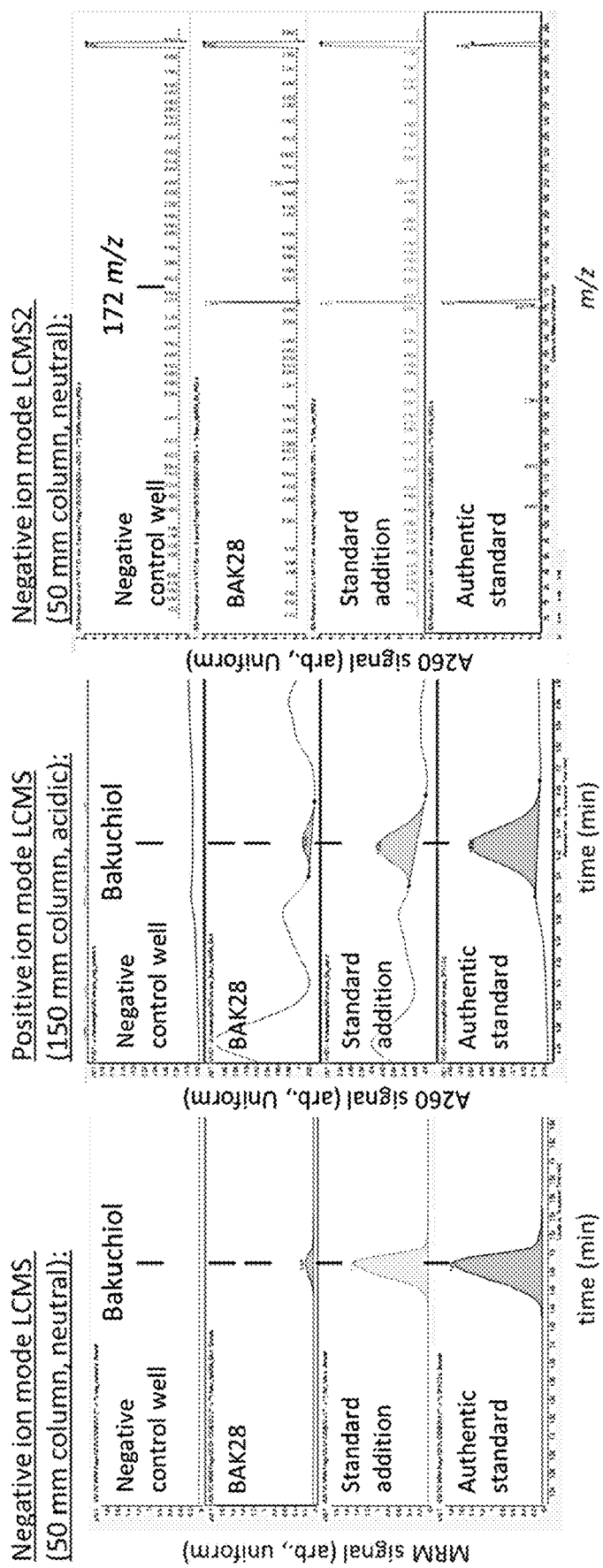
FIG. 1 (FIG. 1) shows, in one implementation, that enzymes BAK28 (SEQ ID NO: 1) and BAK36 (SEQ ID NO: 2) specifically produce bakuchiol.

Bakuchiol is known to be produced by several plant species, including *Psoralea corylifolia, Piper Longum* and *Ulmus davidiana*. However, the complete biosynthetic pathway to produce the compound is previously unknown prior to this application. The present disclosure provides examples that identify prenyltransferase enzymes that may be used to produce bakuchiol through a mechanism involving p-coumaric acid and at least one of geranyl pyrophosphate (GPP), dimethylallyl pyrophosphate (DMAPP), isopentenyl pyrophosphate (IPP), or a combination thereof. This discovery may enable bioproduction of bakuchiol. Thus, the present disclosure provides example methods of producing bakuchiol in a bioreactor or fermenter, which may displace the need for difficult, inefficient synthesis or costly cultivation and extraction of bakuchiol-producing plants. Further, the present disclosure provides example methods of detecting and quantifying bakuchiol via mass spectrometry, which can be useful for quality control of bakuchiol batches produced not only by the disclosed bioproduction methods, but by pre-existing methods as well.

Additionally, the present disclosure provides several examples of prenyltransferase enzymes that are variants of the initially identified enzymes (i.e., SEQ ID NOs: 1 and 2), which may also be used to produce bakuchiol through a mechanism involving p-coumaric acid and at least one of geranyl pyrophosphate (GPP), dimethylallyl pyrophosphate (DMAPP), isopentenyl pyrophosphate (IPP), or a combination thereof. Bioproduction of a target biomolecule, such as bakuchioal, can be enhanced through numerous mechanism, including the identification of enzymes that are capable of producing the target biomolecule in larger quantities, at higher rates, or both. The present disclosure provides examples of prenyltransferase enzymes that are capable of producing bakuchiol in larger quantities and/or at higher rates than previously achieved.

I. Definitions

It is to be understood that the disclosed compositions and methods are not limited to the particular implementations described, and as such may vary. It is also to be understood that the terminology used herein is for the purpose of describing particular implementations only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, "about" means the recited quantity exactly and small variations within a limited range encompassing plus or minus 10% of the recited quantity. In other words, the limited range encompassed can include ±10%, ±9%, ±8%, ±7%, ±6%, ±5%, ±4%, ±3%, ±2%, ±1%, ±0.5%, ±0.2%, ±0.1%, ±0.05%, or smaller, as well as the recited value itself. Thus, by way of example, "about 10" should be understood to mean "10" and a range no larger than "9-11".

As used herein, the term "bioproduction" is intended to mean production of a compound (e.g., bakuchiol, farnesene, farnesol, geosmin, geraniol, terpineol, limonene, myrcene, linalool, hinokitiol, pinene, cafestol, kahweol, cembrene, taxadiene, α-bisabolol, α-guaiene, bergamontene, and valencene) by way of biological or enzymatic synthesis (as opposed to chemical synthesis). In some implementations, bioproduction may be performed by a transgenic organism or microbe that has been engineered to express enzymes involved in the biological synthesis of a compound of interest (e.g., bakuchiol, farnesene, farnesol, geosmin, geraniol, terpineol, limonene, myrcene, linalool, hinokitiol, pinene, cafestol, kahweol, cembrene, taxadiene, α-bisabolol, α-guaiene, bergamontene, and valencene).

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Examples and implementations defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, the term "protein" is a biological macromolecule comprised of one or more chain(s) of amino acids. An "enzyme" is a type of protein that possesses a biological catalytic activity that accelerates chemical reaction. Thus, for the purposes of this disclosure, enzymes are an example of a protein that can catalyze a reaction, such as the production of bakuchiol from GPP/DMAPP/IPP and p-coumaric acid.

The terms "engineered cell" or "engineered host cell" refer to a modified cell wherein the modification can be selected from e.g., increased expression of a gene, inhibited expression of a gene, knockout of a gene, introduction of new gene(s), introduction of mutant gene(s), or mutation/genetic alteration of gene(s), wherein the increased expression or inhibited expression of a gene can be achieved by using common techniques in the art, such as gene deletion, changed gene copy number, changed gene promoter (e.g. by using a strong or weak promoter), etc. An engineered cell or engineered host cell may also include a cell that has been isolated. In some implementations, an engineered cell or engineered host cell is a transgenic cell. In some implementations, an engineered cell or engineered host cell is a transgenic cell capable of producing high levels of a compound or biomolecule of interest. An example of a host cell herein may be a microbial cell (e.g., bacteria, yeast, fungi, etc.).

The term "engineered microbial cell" refers to microbial cells that have been modified by the methods of the present disclosure. Thus, the terms include a microbial cell that has been genetically altered, modified, or engineered, such that it exhibits an altered, modified, or different genotype and/or phenotype (e.g., when the genetic modification affects coding nucleic acid sequences of the host cell), relative to a naturally-occurring organism from which it is derived. It is understood that in some implementations, the terms refer not only to the particular recombinant cell in question, but also to the progeny or potential progeny of such a cell.

For the purposes of this disclosure, all of the proteins, enzymes, and cells disclosed herein can be isolated in a form in which the protein is substantially free of other proteins, contaminants, or macromolecules (e.g., nucleic acids, lipids, etc.). However, it should be understood that an "isolated" protein or enzyme may not be 100% free of other proteins, contaminants, or macromolecules, and absolute purity is not required in order for a protein or enzyme to be considered "isolated." It should also be understood that an "isolated" protein, enzyme, or cell can also be "engineered," "non-engineered," or "wild-type." For the purposes of the present disclosure, an "engineered" protein, enzyme, or cell has been modified in some way (e.g., a substitution, addition, or deletion to an amino acid sequence in the case of a protein or enzyme; or heterologous expression of a non-native protein in the case of a cell) by the hand of man. A "non-engineered" protein, enzyme, or cell may refer to wild-types and naturally occurring irregularities, and a "wild type" is the phenotype or sequence of the typical form of a cell, protein, or enzyme as it occurs in nature (i.e., the "normal" or "standard" cell or protein sequence, as opposed to an engineered variant or a naturally occurring mutant).

As used herein, a "variant" when used in the context of referring to a protein means a protein sequence that is derived from a "parent" or reference sequence by incorporating one or more amino acid changes, which can include substitutions, deletions, or insertions. For the purposes of this disclosure, a variant may comprise an amino acid sequence that shares about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or up to about 100% sequence identity or homology with a reference or "parent" sequence. For purposes of this disclosure, the terms "variant" and "derivative" when used in the context of referring to a protein are used interchangeably.

As used herein, the term "misfolding" or "misfolded" when used in reference to a protein or enzyme means a protein conformational error has occurred. When a protein or enzyme misfolds, it may be non-functional, subject to aggregation, or both.

As used herein, "optional" or "optionally" means that the subsequently described event or circumstance may or may not occur, and that the description includes instances where said event or circumstance occurs and instances where it does not.

For the purpose of the description, a phrase in the form "A/B" or in the form "A and/or B" means (A), (B), or (A and B).

II. Bakuchiol

Bakuchiol is a phenolic compound having a single hydroxyl group on the aromatic ring and an unsaturated hydrocarbon chain. It has been engineered from the seeds of *Psoralea. corylifolia*. The chemical structure of bakuchiol is provided below

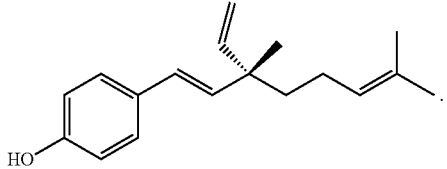 [SMILES: C=C[C@@](C)(/C=C/c1ccc(O)cc1)CCC=C(C)C]

Bakuchiol has been reported as possessing antibacterial activity, anti-inflammatory activity, anti-cancer activity, anti-oxidant activity, and other beneficial properties. As a result, it may be used in supplements, cosmetics, and other consumer products, and it may be employed for pharmaceutical use. However, there are currently a number of limitations associated with the use of this compound due primarily to its low concentration in natural sources, as well as the presence of co-existing toxic components. One of the main problems related to the use of bakuchiol compositions engineered from plants in the *Psoralea* genus is the presence of psoralens, such as psoralen and isopsoralen, which are associated with a number of health risks. Additionally, pre-existing methods of chemically synthesizing bakuchiol or extracting it from plants are generally inefficient and resource intensive.

The presently disclosed proteins and methods make it possible to bioproduce bakuchiol, thus addressing the limitations of pre-existing chemical and extraction-based methodologies.

III. Bakuchiol-Producing Proteins and Nucleic Acids

Not to be bound by particular theory, but one implementation of the methods described herein is based on bakuchiol being produced by a previously unknown prenyltransferase enzyme through a mechanism involving geranyl pyrophosphate (GPP), dimethylallyl pyrophosphate (DMAPP), isopentenyl pyrophosphate (IPP), or a combination thereof, and p-coumaric acid. As explained in further detail in the Non-limiting Working Examples section herein, transcriptome analysis was performed on three known bakuchiol producers (*Psoralea corylifolia, Piper longum* and *Ulmus davidiana*), genes encoding putative prenyltranferase enzymes (i.e., "BAK genes") were identified, and all putative prenyltranferase enzymes (BAK genes) were integrated into *S. cerevisiae* so that the resulting strains could be screened. Of the 196 putative enzymes analyzed, only two proteins were identified that produced bakuchiol when expressed in *S. cerevisiae*:

(SEQ ID NO: 1; referred to herein as "BAK28")
MHEYANMRHRQHNLKHNYGGIEGVSTCEDWARNFVVNAASGESLESHEA
QHHTPETLWGSIKQFCDAFYRFSRPHVIIGTAVNIIVMSSLALEKSSDI
SPKFFIGLFQVIVTILSMNIYTAGINQLTDIEIDKINKPYLPLASGEYS
YKTGVTIITLCAILSLGVGWIVGSPPLFWSNFAYFVLGTVYSIDLPLMR
WKSHPALAALFFFVIRGLTFHVGFFLHLQTHVFKRPMMIPKPVMFGTAF
MSFFYVIIAFFKDIPDIEGDKDHGVKSLTMRLGQKRVFWICVSLLLTGY
GAAIVVGATSSFLWCKLITVSGHALLASIFWNRAKSVDLKSHQEITSLY
MFMWKLFYAEYFIIPLMR, and (SEQ ID NO: 2
MASMFLGSLPLASSVNYIGRITRSKNCTESYHATSYITNASSNKTEKIK
HEYANMRHRQHNLKHNYGGIEGVSTCEDWARNFVVNAASGESLESHEAQ
HHTPETLWGSIKQFCDAFYRFSRPHVIIGTAVNIIVMSSLALEKSSDIS
PKFFIGLFQVIVTILSMNIYTAGINQLTDIEIDKINKPYLPLASGEYSY
KTGVTIITLCAILSLGVGWIVGSPPLFWSNFAYFVLGTVYSIDLPLMRW
KSHPALAALFFFVIRGLTFHVGFFLHLQTHVFKRPMMIPKSVMFGTAFM
SFFYVIIAFFKDIPDIEGDKDHGVKSLTMRLGQERVFWICVSLLLTGYG
AAIVVGATSSFLWCKLITVSGHALLASIFWNRAKSVDLKSHQEITSLYM
FMWKLFYAEYFIIPLMR;

referred to herein as "BAK36"). When these enzymes are expressed in vivo, the N-terminal methionine residue may be cleaved to form a mature enzyme.

The present disclosure further provides additional example putative prenyltranferase enzymes capable of converting p-coumaric acid and GPP/DMAPP/IPP into bakuchiol. Thus, the present disclosure provides bakuchiol-producing enzymes that have at least about 65%—e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. Similarly, the present disclosure provides bakuchiol-producing enzymes that have at least about 65%—e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, the bakuchiol-producing enzyme may share at least about 90% identity with SEQ ID NO: 1 or SEQ ID NO: 2. In some implementations, the bakuchiol-producing enzyme may share at least about 95% identity with SEQ ID NO: 1 or SEQ ID NO: 2. In some implementations, the bakuchiol-producing enzyme may share at least about 99% identity with SEQ ID NO: 1 or SEQ ID NO: 2. Thus, this disclosure encompasses enzymes with varying degrees of sequence identity compared to SEQ ID NOs: 1 and 2, so long as the protein exhibits prenyltranferase activity, is able to produce bakuchiol, or both.

SEQ ID NO: 1 and SEQ ID NO: 2 are structurally similar and share similar amino acid sequences. SEQ ID NO: 1 is missing 49 amino acid residues at its N terminus that are present in SEQ ID NO: 2. Aside from this truncation, there are only two other amino acid substitutions across the length of the protein sequences. This indicates that SEQ ID NOs: 1 and 2 may represent splice variants of the same gene, and further shows in one implementation that the minimum domain involved for activity may be less than the entire 409 amino acid sequence of SEQ ID NO: 2, and a protein that is longer than the 361 amino acid sequence of SEQ ID NO: 1 may be active as well. Accordingly, the present disclosure encompasses protein sequences that are the same length, longer, or shorter than SEQ ID NO: 1 or SEQ ID NO: 2.

For example, a bakuchiol-producing enzyme of the present disclosure may comprise SEQ ID NO: 1 (i.e., it is 361 amino acids or longer). In some implementations, a bakuchiol-producing enzyme of the present disclosure may comprise 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, a bakuchiol-producing enzyme of the present disclosure may consist of SEQ ID NO: 1. In some implementations, a bakuchiol-producing enzyme of the present disclosure may consist of 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, a bakuchiol-producing enzyme of the present disclosure may comprise about 365, about 370, about 375, about 380, about 385, about 390, about 395, about 400, about 405, about 410, about 415, about 420, about 425, about 430, about 435, about 440, or about 450 amino acids, wherein at least about 361 amino acids of the enzyme have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, a bakuchiol-producing enzyme of the present disclosure may comprise about 365 to about 700 amino acids—e.g., about 365 to about 650 amino acids, about 365 to about 600 amino acids, about 365 to about 550 amino acids, about 365 to about 500 amino acids, about 365 to about 450 amino acids, about 365 to about 400 amino acids, about 375 to about 700 amino acids, about 375 to about 650 amino acids, about 375 to about 600 amino acids, about 375 to about 550 amino acids, about 375 to about 500 amino acids, about 375 to about 450 amino acids, about 375 to about 400 amino acids, about 385 to about 700 amino acids, about 385 to about 650 amino acids, about 385 to about 600 amino acids, about 385 to about 550 amino acids, about 385 to about 500 amino acids, about 385 to about 450 amino acids, about 385 to about 400 amino acids, about 395 to about 700 amino acids, about 395 to about 650 amino acids, about 395 to about 600 amino acids, about 395 to about 550 amino acids, about 395 to about 500 amino acids, about 395 to about 450 amino acids, or about 395 to about 400 amino acids, or any values in between; wherein at least about 361 amino acids of the enzyme have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1.

Similarly, a bakuchiol-producing enzyme of the present disclosure may comprise SEQ ID NO: 2 (i.e., it is 409 amino acids or longer). In some implementations, a bakuchiol-producing enzyme of the present disclosure may comprise 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, a bakuchiol-producing enzyme of the present disclosure may consist of SEQ ID NO: 2. In some implementations, a bakuchiol-producing enzyme of the present disclosure may consist of 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, a bakuchiol-producing enzyme of the present disclosure may comprise about 410, about 415, about 420, about 425, about 430, about 435, about 440, or about 450 amino acids, wherein at least about 409 amino acids of the enzyme have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, a bakuchiol-producing enzyme of the present disclosure may comprise about 410 to about 700 amino acids—e.g., about 410 to about 650 amino acids, about 410 to about 600 amino acids, about 410 to about 550 amino acids, about 410 to about 500 amino acids, about 410 to about 450 amino acids, about 420 to about 700 amino acids, about 420 to about 650 amino acids, about 420 to about 600 amino acids, about 420 to about 550 amino acids, about 420 to about 500 amino acids, about 420 to about 450 amino acids, about 430 to about 700 amino acids, about 430 to about 650 amino acids, about 430 to about 600 amino acids, about 430 to about 550 amino acids, about 430 to about 500 amino acids, about 430 to about 450 amino acids, about 440 to about 700 amino acids, about 440 to about 650 amino acids, about 440 to about 600 amino acids, about 440 to about 550 amino acids, about 440 to about 500 amino acids, or about 440 to about 450 amino acids, or any values in between, wherein at least about 409 amino acids of the enzyme have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2.

Bakuchiol-producing enzymes described herein include also those that are shorter than SEQ ID NO: 1 or SEQ ID NO: 2. A bakuchiol-producing enzyme may be less than 409 or less than 361 amino acids in length, so long as the enzyme has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the enzyme can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2, so long as the enzyme exhibits prenyltransferase activity, is able to catalyze bakuchiol production, or both.

Indeed, for the purposes of this disclosure, any of the disclosed proteins is considered a "bakuchiol-producing protein" or a "bakuchiol-producing enzyme" if the protein exhibits prenyltransferase activity, catalyzes the production of bakuchiol, or both. Further, it should be understood for the purposes of this disclosure that a protein "exhibits" prenyltransferase activity or "catalyzes" the production of bakuchiol if the foregoing functions are significant enough to be measured, observed, or detected using conventional methods in the art (e.g., mass spectrometry).

The present disclosure also provides nucleic acids comprising a nucleic acid sequence encoding any one of the proteins disclosed herein. A nucleic acid sequence can be designed/determined based on a known amino acid sequence as a result of known codon specificity. Thus, in some implementations, the nucleic acid may comprise a nucleic acid sequence encoding SEQ ID NO: 1, SEQ ID NO: 2, or a protein that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2, so long as the protein exhibits prenyltransferase activity, is able to catalyze bakuchiol production, or both.

Because the disclosed proteins may be of particular value when used in the context of transgenic expression in a microbial chassis, the nucleic acid sequence encoding any one of the disclosed proteins may be codon-optimized for a given expression system. For example, the nucleic acid sequence may be codon-optimized for expression is a yeast system, such as *S. cerevisiae*. Alternatively, the nucleic acid sequence may be codon-optimized for expression is a prokaryotic system, such as *E. coli*.

Nucleic acids that encode a bakuchiol-producing protein can be incorporated into an expression vector or expression cassette. The nucleic acid can be transduced or transformed into a transgenic cell such that the nucleic acid sequence encoding the bakuchiol-producing protein is integrated into the genome of the host cell or transgenic cell. Alternatively, the nucleic acid sequence encoding the bakuchiol-producing protein may be expressed without integration into the host genome (e.g., in the form of a plasmid). For those implementations in which genome integration is desired, any suitable methods of integration can be used, including but not limited to Cas-based systems (e.g., Cas9, Cas12, etc.), homologous recombination, gene gun, conjugation protocols, lambda red, etc.

An expression cassette or vector for expressing the nucleic acid sequence encoding the bakuchiol-producing protein may comprise a promoter and a terminator. Any suitable promoters may be used, including but not limited to GAL1, TEF2, TEF1, TDH3, ENO2, CCW12, EF-1a promoter, CMV immediate early, HSV thymidine kinase, early and late SV40, LTRs from retrovirus, and mouse metallothionein-I. In some implementations, an inducible or repressible promoter, such as GAL1, GAL2, GAL7, GAL10, CUP1, MET3, MET17, or MET25, may be used. Inducible promoters operably link the expression of a target gene (e.g., the nucleic acid sequence encoding a bakuchiol-producing protein) to a specific signal or a particular biotic or abiotic factor. Types of inducible promoters that may be utilized in the disclosed may include, but are not limited to, chemically-inducible promoters (i.e., antibiotics, steroids, metals, etc.), light-inducible promoters, heat-inducible promoters, and hypoxia-inducible promoters. Transcription terminators that may be used are also known in the art (see Bittner et al., Methods in Enzymol. 153: 516-544 (1987)), and include but are not limited to GAT2, Rho-dependent terminators, Rho-independent terminators, poly-A sequences, and the like (see Curran et al., Metab. Eng., 19: 88-97 (2013)).

For the purposes of the present disclosure, any of the foregoing proteins or enzymes can be expressed in a host cell or transgenic cell and any of the foregoing nucleic acids may incorporated into a host cell or transgenic cell in order to produce bakuchiol according to the disclosed methods. Additionally, for the purposes of this disclosure, all of the foregoing proteins or enzymes can be isolated, in a form in which the protein or enzyme is essentially free of other proteins, contaminants, or macromolecules (e.g., nucleic acids, lipids, etc.).

IV. Bakuchiol-Producing Enzyme Variants

Described herein are bakuchiol-producing enzyme variants comprising an amino acid sequence that is a variant of the amino acid sequence of the bakuchiol-producing enzymes set forth in SEQ ID NO: 1 or SEQ ID NO: 2. These enzyme variants may also be referred to an "engineered bakuchiol-producing enzymes," as the variants comprise at least one change relative to a naturally occurring sequence. Thus, for the purposes of the present disclosure, a variant sequence has at least one substitution, addition, or deletion, relative to SEQ ID NO: 1 or SEQ ID NO: 2. In some implementations, the at least one substitution, addition, or deletion increases the production of bakuchiol by the variant relative to the wild-type bakuchiol-producing enzyme. The disclosed substitutions and deletions may be combined to produce synergistic effects on bakuchiol production.

The present disclosure provides variants of BAK28 and BAK36 with improved bakuchiol-producing activity. In some implementations, a variant may have an amino acid has about 80%, about 85%, about 90%, about 91%, about 92%, about 93%, about 94%, about 95%, about 96%, about 97%, about 98%, or about 99% identity to wild-type BAK28 (SEQ ID NO: 1) or BAK36 (SEQ ID NO: 2). In some implementations, a variant may share about 80%, about 85%, about 90%, about 91%, about 92%, about 93%, about 94%, about 95%, about 96%, about 97%, about 98%, or about 99% homology to wild-type BAK28 (SEQ ID NO: 1) or BAK36 (SEQ ID NO: 2). For instance, in some implementations, a variant may comprise the amino acids residues conserved between BAK28 and BAK36.

It is observed that, in many instances, an N-terminal deletion, surprisingly, improves bakuchiol-producing activity of both BAK28 and BAK36. This observation suggests that the C-terminus of BAK28 and BAK36 may be involved in catalyzing the production of bakuchiol, while the N-terminus may play a lesser or no role in the production of bakuchiol. For example, the bakuchiol-producing enzyme variant may comprise an N-terminal deletion of from 1 to 100 amino acid residues of SEQ ID NO: 1, or an N-terminal deletion of from 1 to 150 amino acid residues of SEQ ID NO: 2. In some implementations, a variant may comprise an N-terminal deletion of amino acid residues 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, or 1-72, of SEQ ID NO: 1. In some implementations, a variant may comprise an N-terminal deletion of amino acid residues 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, or 2-72, of SEQ ID NO: 1. In some implementations, a variant comprises an N-terminal deletion of amino acid residues 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, -172, 1-73, 1-74, 1-75, 1-76, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, or 1-120 of SEQ ID NO: 2.

Thus, a bakuchiol-producing enzyme variant may comprise an N-terminal deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51,52. 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 consecutive amino acids from SEQ ID NO: 1 or SEQ ID NO: 2. In other words, the present disclosure provides, an engineered bakuchiol-producing enzyme comprising an N-terminal deletion of 1 to about 120 amino acids (e.g., 2 to about 120 amino acids) from the N-terminus of the enzyme, wherein the enzyme catalyzes production of bakuchiol, exhibits prenyltransferase activity, or both. The N-terminal deletion, in several instances, surprisingly is found to increase catalyzation of production of bakuchiol, prenyltransferase activity, or both, relative to a non-engineered enzyme comprising the same amino acid sequence but without the N-terminal deletion.

In some implementations, a variant may additionally or alternatively comprise a deletion at the C-terminus of the protein. Such a C-terminal deletion may encompass 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more consecutive amino acids. However, in some implementations, a variant does not comprise any deletions to its C-terminal domain. Indeed, in some implementations, deletions from the C-terminus or modifications to the amino acid sequence of the C-terminus may be detrimental to bakuchiol-producing activity.

The amino acid sequence of BAK36(T1), a variant comprising an N-terminal deletion of the T1 region of BAK36, and further example variants thereof are set forth in Table 1 below.

TABLE 1

Amino Acid Sequences of N-terminally truncated BAK36 and Exemplary Variants

| Enzyme | SEQ ID NO. | Sequence |
| --- | --- | --- |
| BAK36(T1) | 3 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAIVVGATSSFLWCKLITVSGHALLASIFWNRA<br>KSVDLKSHQEITSLYMFMWKLFYAEYFIIPLMR |
| BAK36(T1)<br>E54F | 4 | MTNASSNKTEKIKHEYANMRHRQHNLKHNYGGIEGVSTCE<br>DWARNFVVNAASGFSLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAIVVGATSSFLWCKLITVSGHALLASIFWNRA<br>KSVDLKSHQEITSLYMFMWKLFYAEYFIIPLMR |
| BAK36(T1)<br>G71D | 5 | MTNASSNKTEKIKHEYANMRHRQHNLKHNYGGIEGVSTCE<br>DWARNFVVNAASGESLESHEAQHHTPETLWDSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP |

TABLE 1-continued

Amino Acid Sequences of N-terminally truncated BAK36 and Exemplary Variants

| Enzyme | SEQ ID NO. | Sequence |
|---|---|---|
| | | ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) S108L | 6 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSLDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) T162H | 7 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKHGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) P185V | 8 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPVLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) V199G | 9 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTGYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) P205L | 10 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLLLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) P205V | 11 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLVLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) L206Y | 12 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPYMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |

TABLE 1-continued

Amino Acid Sequences of N-terminally truncated BAK36 and Exemplary Variants

| Enzyme | SEQ ID NO. | Sequence |
|---|---|---|
| BAK36(T1) W209S | 13 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRSKSHPA LAALFFFVIRGLTFHVGFFLHLQTHVFKRPMMIPKSVMFGTA FMSFFYVIIAFFKDIPDIEGDKDHGVKSLTMRLGQERVFWICV SLLLTGYGAAIVVGATSSFLWCKLITVSGHALLASIFWNRAK SVDLKSHQEITSLYMFMWKLFYAEYFIIPLMR |
| BAK36(T1) W209C | 14 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRCKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209V | 15 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRVKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209T | 16 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRTKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209Y | 17 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRYKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209R | 18 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRRKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209M | 19 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRMKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209Q | 20 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS |

TABLE 1-continued

Amino Acid Sequences of N-terminally truncated BAK36 and Exemplary Variants

| Enzyme | SEQ ID NO. | Sequence |
|---|---|---|
| | | MNIYTAGINQLTDIEIDKINKPYLPLASGEYSYKTGVTIITLCA ILSLGVGWIVGSPPLFWSNFAYFVLGTVYSIDLPLMRQKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209A | 56 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRAKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209N | 57 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRNKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209D | 58 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRDKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209E | 59 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMREKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209G | 60 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRGKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209H | 61 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRHKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209I | 62 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRIKSHPA LAALFFFVIRGLTFHVGFFLHLQTHVFKRPMMIPKSVMFGTA FMSFFYVIIAFFKDIPDIEGDKDHGVKSLTMRLGQERVFWICV |

TABLE 1-continued

Amino Acid Sequences of N-terminally truncated BAK36 and Exemplary Variants

| Enzyme | SEQ ID NO. | Sequence |
|---|---|---|
| | | SLLLTGYGAAIVVGATSSFLWCKLITVSGHALLASIFWNRAK SVDLKSHQEITSLYMFMWKLFYAEYFIIPLMR |
| BAK36(T1) W209L | 63 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRLKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209K | 64 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRKKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209F | 65 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRFKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) W209P | 66 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRPKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) L226M | 21 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGMTFHVGFFLHLQTHVFKRPMMIPKSVMFG TAFMSFFYVIIAFFKDIPDIEGDKDHGVKSLTMRLGQERVFWI CVSLLLTGYGAAIVVGATSSFLWCKLITVSGHALLASIFWNR AKSVDLKSHQEITSLYMFMWKLFYAEYFIIPLMR |
| BAK36(T1) L234Q | 22 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFQHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) F257E | 23 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AEMSFFYVIIAFFKDIPDIEGDKDHGVKSLTMRLGQERVFWI CVSLLLTGYGAAIVVGATSSFLWCKLITVSGHALLASIFWNR AKSVDLKSHQEITSLYMFMWKLFYAEYFIIPLMR |

TABLE 1-continued

Amino Acid Sequences of N-terminally truncated BAK36 and Exemplary Variants

| Enzyme | SEQ ID NO. | Sequence |
|---|---|---|
| BAK36(T1) K269R | 24 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFRDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) I274L | 25 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDLEGDKDHGVKSLTMRLGQERVFWI CVSLLLTGYGAAIVVGATSSFLWCKLITVSGHALLASIFWNR AKSVDLKSHQEITSLYMFMWKLFYAEYFIIPLMR |
| BAK36(T1) D279C | 26 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKCHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) D279K | 27 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKKHGVKSLTMRLGQERVFWIC VSLLLTGYGAAIVVGATSSFLWCKLITVSGHALLASIFWNR AKSVDLKSHQEITSLYMFMWKLFYAEYFIIPLMR |
| BAK36(T1) D279R | 28 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKRHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) D279M | 29 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKMHGVKSLTMRLGQERVFWI CVSLLLTGYGAAIVVGATSSFLWCKLITVSGHALLASIFWNR AKSVDLKSHQEITSLYMFMWKLFYAEYFIIPLMR |
| BAK36(T1) D279L | 30 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKLHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) M287V | 31 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA |

TABLE 1-continued

Amino Acid Sequences of N-terminally truncated BAK36 and Exemplary Variants

| Enzyme | SEQ ID NO. | Sequence |
|---|---|---|
| | | ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTVRLGQERVFWIC<br>VSLLLTGYGAAIVVGATSSFLWCKLITVSGHALLASIFWNRA<br>KSVDLKSHQEITSLYMFMWKLFYAEYFIIPLMR |
| BAK36(T1)<br>M287F | 32 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTFRLGQERVFWIC<br>VSLLLTGYGAAIVVGATSSFLWCKLITVSGHALLASIFWNRA<br>KSVDLKSHQEITSLYMFMWKLFYAEYFIIPLMR |
| BAK36(T1)<br>M287Y | 33 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTYRLGQERVFWIC<br>VSLLLTGYGAAIVVGATSSFLWCKLITVSGHALLASIFWNRA<br>KSVDLKSHQEITSLYMFMWKLFYAEYFIIPLMR |
| BAK36(T1)<br>I310V | 34 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAVVVGATSSFLWCKLITVSGHALLASIFWNR<br>AKSVDLKSHQEITSLYMFMWKLFYAEYFIIPLMR |
| BAK36(T1)<br>V312W | 35 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAIVWGATSSFLWCKLITVSGHALLASIFWNRA<br>KSVDLKSHQEITSLYMFMWKLFYAEYFIIPLMR |
| BAK36(T1)<br>V312A | 36 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAIVAGATSSFLWCKLITVSGHALLASIFWNRA<br>KSVDLKSHQEITSLYMFMWKLFYAEYFIIPLMR |
| BAK36(T1)<br>V312F | 37 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC<br>VSLLLTGYGAAIVFGATSSFLWCKLITVSGHALLASIFWNRA<br>KSVDLKSHQEITSLYMFMWKLFYAEYFIIPLMR |
| BAK36(T1)<br>V312G | 38 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDIEGDKDHGVKSLTMRLGQERVFWIC |

TABLE 1-continued

Amino Acid Sequences of N-terminally truncated BAK36 and Exemplary Variants

| Enzyme | SEQ ID NO. | Sequence |
|---|---|---|
| | | VSLLLTGYGAAIVGGATSSFLWCKLITVSGHALLASIFWNRA KSVDLKSHQEITSLYMFMWKLFYAEYFIIPLMR |
| BAK36(T1) V312Y | 39 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVYGATSSFLWCKLITVSGHALLASIFWNRA KSVDLKSHQEITSLYMFMWKLFYAEYFIIPLMR |
| BAK36(T1) V312C | 40 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVCGATSSFLWCKLITVSGHALLASIFWNRA KSVDLKSHQEITSLYMFMWKLFYAEYFIIPLMR |
| BAK36(T1) V312L | 41 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVLGATSSFLWCKLITVSGHALLASIFWNRA KSVDLKSHQEITSLYMFMWKLFYAEYFIIPLMR |
| BAK36(T1) G313I | 42 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVIATSSFLWCKLITVSGHALLASIFWNRA KSVDLKSHQEITSLYMFMWKLFYAEYFIIPLMR |
| BAK36(T1) S317P | 43 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSPFLWCKLITVSGHALLASIFWNRA KSVDLKSHQEITSLYMFMWKLFYAEYFIIPLMR |
| BAK36(T1) S317I | 44 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSIFLWCKLITVSGHALLASIFWNRA KSVDLKSHQEITSLYMFMWKLFYAEYFIIPLMR |
| BAK36(T1) F318R | 45 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSRLWCKLITVSGHALLASIFWNRA KSVDLKSHQEITSLYMFMWKLFYAEYFIIPLMR |

TABLE 1-continued

Amino Acid Sequences of N-terminally truncated BAK36 and Exemplary Variants

| Enzyme | SEQ ID NO. | Sequence |
|---|---|---|
| BAK36(T1) F318G | 46 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSGLWCKLITVSGHALLASIFWNRA KSVDLKSHQEITSLYMFMWKLFYAEYFIIPLMR |
| BAK36(T1) L319P | 47 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFPWCKLITVSGHALLASIFWNRA KSVDLKSHQEITSLYMFMWKLFYAEYFIIPLMR |
| BAK36(T1) W320D | 48 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLDCKLITVSGHALLASIFWNRA KSVDLKSHQEITSLYMFMWKLFYAEYFIIPLMR |
| BAK36(T1) T325G | 49 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLIGVSGHALLASIFWNRA KSVDLKSHQEITSLYMFMWKLFYAEYFIIPLMR |
| BAK36(T1) S342G | 50 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KGVDLKSHQEITSLYMFMWKLFYAEYFIIPLMR |
| BAK36(T1) L354F | 51 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRWKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSFYMFMWKLFYAEYFIIPLMR |
| BAK36(T1) E54F; W209C; D279K; M287V; V312L; F318R; S342G | 67 | MTNASSNKTEKIKHEYANMRHRQHNLKHNYGGIEGVSTCE DWARNFVVNAASGFSLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRCKSHP ALAALFFFVIRGLTFHVGFFLHLQTHVFKRPMMIPKSVMFGT AFMSFFYVIIAFFKDIPDIEGDKKHGVKSLTVRLGQERVFWIC VSLLLTGYGAAIVLGATSSRLWCKLITVSGHALLASIFWNRA KGVDLKSHQEITSLYMFMWKLFYAEYFIIPLMR |
| BAK36(T1) P205L; L206Y; W209Y; | 68 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA |

TABLE 1-continued

Amino Acid Sequences of N-terminally truncated BAK36 and Exemplary Variants

| Enzyme | SEQ ID NO. | Sequence |
|---|---|---|
| M287V;<br>V312L;<br>S342G | | ILSLGVGWIVGSPPLFWSNFAYFVLGTVYSIDLLYMRYKSHP<br>ALAALFFFVIRGLTFHVGFFLHLQTHVFKRPMMIPKSVMFGT<br>AFMSFFYVIIAFFKDIPDIEGDKDHGVKSLTVRLGQERVFWIC<br>VSLLLTGYGAAIVLGATSSFLWCKLITVSGHALLASIFWNRA<br>KGVDLKSHQEITSLYMFMWKLFYAEYFIIPLMR |
| BAK36(T1)<br>T65C;<br>L206Y;<br>W209I;<br>I274L;<br>D279L;<br>M287F;<br>V312Y;<br>E350G;<br>L354F | 69 | MTNASSNKTEKIKHEYANMRHRQHNLKHNYGGIEGVSTCE<br>DWARNFVVNAASGESLESHEAQHHCPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPYMRIKSHPA<br>LAALFFFVIRGLTFHVGFFLHLQTHVFKRPMMIPKSVMFGTA<br>FMSFFYVIIAFFKDIPDLEGDKLHGVKSLTFRLGQERVFWICV<br>SLLLTGYGAAIVYGATSSFLWCKLITVSGHALLASIFWNRAK<br>SVDLKSHQGITSFYMFMWKLFYAEYFIIPLMR |
| BAK36(T1)<br>P185V;<br>W209V;<br>L226M;<br>D279K;<br>V312L;<br>S342G;<br>L354F | 70 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPVLFWSNFAYFVLGTVYSIDLPLMRVKSHP<br>ALAALFFFVIRGMTFHVGFFLHLQTHVFKRPMMIPKSVMFGT<br>AFMSFFYVIIAFFKDIPDIEGDKKHGVKSLTMRLGQERVFWIC<br>VSLLLTGYGAAIVLGATSSFLWCKLITVSGHALLASIFWNRA<br>KGVDLKSHQEITSFYMFMWKLFYAEYFIIPLMR |
| BAK36(T1)<br>I274L;<br>D279R;<br>V312W;<br>L354F | 71 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTVYSIDLPLMRWKSHP<br>ALAALFFFVIRGLTFHVGFFLHLQTHVFKRPMMIPKSVMFGT<br>AFMSFFYVIIAFFKDIPDLEGDKRHGVKSLTMRLGQERVFWI<br>CVSLLLTGYGAAIVWGATSSFLWCKLITVSGHALLASIFWNR<br>AKSVDLKSHQEITSFYMFMWKLFYAEYFIIPLMR |
| BAK36(T1)<br>T162H;<br>P185V;<br>V199G;<br>P205L;<br>L206Y;<br>W209V;<br>L226M;<br>I274L;<br>M287F;<br>G313I;<br>F318R;<br>T325G;<br>L354F | 72 | MTNASSNKTEKIKHEYANMRHRQHNLKHNYGGIEGVSTCE<br>DWARNFVVNAASGESLESHEAQHHTPETLWGSIKQFCDAFY<br>RFSRPHVIIGTAVNIIVMSSLALEKSSDISPKFFIGLFQVIVTILS<br>MNIYTAGINQLTDIEIDKINKPYLPLASGEYSYKHGVTIITLCA<br>ILSLGVGWIVGSPVLFWSNFAYFVLGTGYSIDLLYMRVKSHP<br>ALAALFFFVIRGMTFHVGFFLHLQTHVFKRPMMIPKSVMFGT<br>AFMSFFYVIIAFFKDIPDLEGDKDHGVKSLTFRLGQERVFWIC<br>VSLLLTGYGAAIVVIATSSRLWCKLIGVSGHALLASIFWNRA<br>KSVDLKSHQEITSFYMFMWKLFYAEYFIIPLMR |
| BAK36(T1)<br>E54F;<br>S108L;<br>V199G;<br>L206Y;<br>W209S;<br>K269R;<br>I274L;<br>D279M;<br>M287V;<br>V312F;<br>S317I;<br>S342G | 73 | MTNASSNKTEKIKHEYANMRHRQHNLKHNYGGIEGVSTCE<br>DWARNFVVNAASGFSLESHEAQHHTPETLWGSIKQFCDAFY<br>RFSRPHVIIGTAVNIIVMSSLALEKSLDISPKFFIGLFQVIVTILS<br>MNIYTAGINQLTDIEIDKINKPYLPLASGEYSYKTGVTIITLCA<br>ILSLGVGWIVGSPPLFWSNFAYFVLGTGYSIDLPYMRSKSHP<br>ALAALFFFVIRGLTFHVGFFLHLQTHVFKRPMMIPKSVMFGT<br>AFMSFFYVIIAFFRDIPDLEGDKMHGVKSLTVRLGQERVFWI<br>CVSLLLTGYGAAIVFGATSIFLWCKLITVSGHALLASIFWNRA<br>KGVDLKSHQEITSLYMFMWKLFYAEYFIIPLMR |

TABLE 1-continued

Amino Acid Sequences of N-terminally truncated BAK36 and Exemplary Variants

| Enzyme | SEQ ID NO. | Sequence |
|---|---|---|
| BAK36(T1) V199G; P205L; L226M; M287V; S317I; F318R; S342G | 74 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTGYSIDLLLMRWKSHP ALAALFFFVIRGMTFHVGFFLHLQTHVFKRPMMIPKSVMFGT AFMSFFYVIIAFFKDIPDIEGDKDHGVKSLTVRLGQERVFWIC VSLLLTGYGAAIVVGATSIRLWCKLITVSGHALLASIFWNRA KGVDLKSHQEITSLYMFMWKLFYAEYFIIPLMR |
| BAK36(T1) S108L; T162H; P185V; V199G; P205L; L206Y; W209S; L234Q; D279R; V312F | 75 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSLDISPKFFIGLFQVIVTILS MNIYTAGINQLTDIEIDKINKPYLPLASGEYSYKHGVTIITLCA ILSLGVGWIVGSPVLFWSNFAYFVLGTGYSIDLLYMRSKSHP ALAALFFFVIRGLTFHVGFFQHLQTHVFKRPMMIPKSVMFGT AFMSFFYVIIAFFKDIPDIEGDKRHGVKSLTMRLGQERVFWIC VSLLLTGYGAAIVFGATSSFLWCKLITVSGHALLASIFWNRA KSVDLKSHQEITSLYMFMWKLFYAEYFIIPLMR |
| BAK36(T1) S108L; T162H; P185V; V199G; P205L; L206Y; W209S; L234Q; D279R; V312F | 76 | MTNASSNKTEKIKHEYANMRHRQHNLKHNYGGIEGVSTCE DWARNFVVNAASGESLESHEAQHHTPETLWGSIKQFCDAFY RFSRPHVIIGTAVNIIVMSSLALEKSLDISPKFFIGLFQVIVTILS MNIYTAGINQLTDIEIDKINKPYLPLASGEYSYKHGVTIITLCA ILSLGVGWIVGSPVLFWSNFAYFVLGTGYSIDLLYMRSKSHP ALAALFFFVIRGLTFHVGFFQHLQTHVFKRPMMIPKSVMFGT AFMSFFYVIIAFFKDIPDIEGDKRHGVKSLTMRLGQERVFWIC VSLLLTGYGAAIVFGATSSFLWCKLITVSGHALLASIFWNRA KSVDLKSHQEITSLYMFMWKLFYAEYFIIPLMR |
| BAK36(T1) V48S; P185V; P205L; W209T; I274L; D279M; M287F; V312C; G313I; F318R | 77 | MTNASSNKTEKIKHEYANMRHRQHNLKHNYGGIEGVSTCE DWARNFVSNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPVLFWSNFAYFVLGTVYSIDLLLMRTKSHP ALAALFFFVIRGLTFHVGFFLHLQTHVFKRPMMIPKSVMFGT AFMSFFYVIIAFFKDIPDLEGDKMHGVKSLTFRLGQERVFWI CVSLLLTGYGAAIVCIATSSRLWCKLITVSGHALLASIFWNR AKSVDLKSHQEITSLYMFMWKLFYAEYFIIPLMR |
| BAK36(T1) E54F; T162H; P185V; L206Y; L234Q; K269R; I274L; D279M; M287V; V312Y; S342G; L354F | 78 | MTNASSNKTEKIKHEYANMRHRQHNLKHNYGGIEGVSTCE DWARNFVVNAASGFSLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKHGVTIITLCA ILSLGVGWIVGSPVLFWSNFAYFVLGTVYSIDLPYMRWKSHP ALAALFFFVIRGLTFHVGFFQHLQTHVFKRPMMIPKSVMFGT AFMSFFYVIIAFFRDIPDLEGDKMHGVKSLTVRLGQERVFWI CVSLLLTGYGAAIVYGATSSFLWCKLITVSGHALLASIFWNR AKGVDLKSHQEITSFYMFMWKLFYAEYFIIPLMR |

TABLE 1-continued

Amino Acid Sequences of N-terminally truncated BAK36 and Exemplary Variants

| Enzyme | SEQ ID NO. | Sequence |
|---|---|---|
| BAK36(T1) G71D; S108L; T162H; P185V; V199G; P205L; L206Y; W209S; L226M; L234Q; I274L; M287V; V312W; F318R | 79 | MTNASSNKTEKIKHEYANMRHRQHNLKHNYGGIEGVSTCE DWARNFVVNAASGESLESHEAQHHTPETLWDSIKQFCDAFY RFSRPHVIIGTAVNIIVMSSLALEKSLDISPKFFIGLFQVIVTILS MNIYTAGINQLTDIEIDKINKPYLPLASGEYSYKHGVTIITLCA ILSLGVGWIVGSPVLFWSNFAYFVLGTGYSIDLLYMRSKSHP ALAALFFFVIRGMTFHVGFFQHLQTHVFKRPMMIPKSVMFG TAFMSFFYVIIAFFKDIPDLEGDKDHGVKSLTVRLGQERVFWI CVSLLLTGYGAAIVWGATSSRLWCKLITVSGHALLASIFWNR AKSVDLKSHQEITSLYMFMWKLFYAEYFIIPLMR |
| BAK36(T1) V48S, W209C | 80 | MTNASSNKTEKIKHEYANMRHRQHNLKHNYGGIEGVSTCE DWARNFVSNAASGESLESHEAQHHTPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRCKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |
| BAK36(T1) T65C, W209C | 81 | MTNASSNKTEKIKHEYANMRHRQHNLKHNYGGIEGVSTCE DWARNFVVNAASGESLESHEAQHHCPETLWGSIKQFCDAFY RFSRPHVIIGTAVNIIVMSSLALEKSSDISPKFFIGLFQVIVTILS MNIYTAGINQLTDIEIDKINKPYLPLASGEYSYKTGVTIITLCA ILSLGVGWIVGSPPLFWSNFAYFVLGTVYSIDLPLMRCKSHP ALAALFFFVIRGLTFHVGFFLHLQTHVFKRPMMIPKSVMFGT AFMSFFYVIIAFFKDIPDIEGDKDHGVKSLTMRLGQERVFWIC VSLLLTGYGAAIVVGATSSFLWCKLITVSGHALLASIFWNRA KSVDLKSHQEITSLYMFMWKLFYAEYFIIPLMR |

Additionally, the N-terminal methionine of any of the forgoing variants (i.e., SEQ ID NOs: 3-51 and 56-81) may also be cleaved off in a purified product or after expression in vivo. However, all amino acid position designations disclosed in this table take the methionine residue into account for the purpose of maintaining amino acid numbering conventions.

In some implementations, a bakuchiol-producing enzyme variant as described herein may have at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the wild-type BAK28 enzyme (SEQ ID NO: 1), or to an N-terminal deletion variant thereof having a deletion of up to 73 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52. 53, 54, 55, 56, 57, 58, 59, 60, 61, 62, 63, 64, 65, 66, 67, 68, 69, 70, 71, 72, or 73) N-terminal amino acid residues of SEQ ID NO: 1.

In some implementations, a bakuchiol-producing enzyme variant as described herein may have at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the wild-type BAK36 enzyme (SEQ ID NO: 2), or to an N-terminal deletion variant thereof having a deletion of up to 120 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52. 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) N-terminal amino acid residues of SEQ ID NO: 2.

In some implementations, a bakuchiol-producing enzyme variant as described herein may comprise, or consist of, SEQ ID NO: 3. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 3. In some implementations, a bakuchiol-producing enzyme variant can comprise an amino acid sequence comprising at least one (e.g., 1, 2, 3, 4, or 5 or more) substitution mutation(s) relative to SEQ ID NO: 3 at one or more amino acid positions selected from 54, 71, 108, 162, 185, 199, 205, 206, 209, 226, 234, 257, 269, 274, 279, 287, 310, 312, 313, 317, 318, 319, 320, 325, 342, and 354.

In some implementations, a bakuchiol-producing enzyme variant as described herein may comprise, or consist of, SEQ ID NO: 4. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 4.

In some implementations, a bakuchiol-producing enzyme variant as described herein may comprise, or consist of, SEQ ID NO: 5. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 5.

In some implementations, a bakuchiol-producing enzyme variant as described herein may comprise, or consist of, SEQ ID NO: 6. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 6.

In some implementations, a bakuchiol-producing enzyme variant as described herein may comprise, or consist of, SEQ ID NO: 7. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 7.

In some implementations, a bakuchiol-producing enzyme variant as described herein may comprise, or consist of, SEQ ID NO: 8. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 8.

In some implementations, a bakuchiol-producing enzyme variant as described herein may comprise, or consist of, SEQ ID NO: 9. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 9.

In some implementations, a bakuchiol-producing enzyme variant as described herein may comprise, or consist of, SEQ ID NO: 10. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 10.

In some implementations, a bakuchiol-producing enzyme variant as described herein may comprise, or consist of, SEQ ID NO: 11. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 11.

In some implementations, a bakuchiol-producing enzyme variant as described herein may comprise, or consist of, SEQ ID NO: 12. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 12.

In some implementations, a bakuchiol-producing enzyme variant as described herein may comprise, or consist of, SEQ ID NO: 13. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 13.

In some implementations, a bakuchiol-producing enzyme variant as described herein may comprise, or consist of, SEQ ID NO: 14. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 14.

In some implementations, a bakuchiol-producing enzyme variant as described herein may comprise, or consist of, SEQ ID NO: 15. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 15.

In some implementations, a bakuchiol-producing enzyme variant as described herein may comprise, or consist of, SEQ ID NO: 16. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 16.

In some implementations, a bakuchiol-producing enzyme variant as described herein may comprise, or consist of, SEQ ID NO: 17. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 17.

In some implementations, a bakuchiol-producing enzyme variant as described herein may comprise, or consist of, SEQ ID NO: 18. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about In some implementations, a bakuchiol-producing enzyme variant as described herein may comprise, or consist, of SEQ ID NO: 19. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 19.

In some implementations, a bakuchiol-producing enzyme variant as described herein may comprise, or consist, of SEQ ID NO: 20. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 20.

In some implementations, a bakuchiol-producing enzyme variant as described herein may comprise, or consist, of SEQ ID NO: 21. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 21.

In some implementations, a bakuchiol-producing enzyme variant as described herein may comprise, or consist, of SEQ ID NO: 22. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 22.

In some implementations, a bakuchiol-producing enzyme variant as described herein may comprise, or consist, of SEQ ID NO: 23. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 23.

In some implementations, a bakuchiol-producing enzyme variant as described herein may comprise, or consist, of SEQ ID NO: 24. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 24.

In some implementations, a bakuchiol-producing enzyme variant as described herein may comprise, or consist, of SEQ ID NO: 25. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 25.

In some implementations, a bakuchiol-producing enzyme variant as described herein may comprise, or consist, of SEQ ID NO: 26. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 26.

In some implementations, a bakuchiol-producing enzyme variant as described herein may comprise, or consist, of SEQ ID NO: 27. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 27.

In some implementations, a bakuchiol-producing enzyme variant as described herein may comprise, or consist, of SEQ ID NO: 28. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 28.

In some implementations, a bakuchiol-producing enzyme variant as described herein may comprise, or consist, of SEQ ID NO: 29. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 29.

In some implementations, a bakuchiol-producing enzyme variant as described herein may comprise, or consist, of SEQ ID NO: 30. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 30.

In some implementations, a bakuchiol-producing enzyme variant as described herein may comprise, or consist, of SEQ ID NO: 31. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 31.

In some implementations, a bakuchiol-producing enzyme variant as described herein may comprise, or consist, of SEQ ID NO: 32. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 32.

In some implementations, a bakuchiol-producing enzyme variant as described herein may comprise, or consist, of SEQ ID NO: 33. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 33.

In some implementations, a bakuchiol-producing enzyme variant as described herein may comprise, or consist, of SEQ ID NO: 34. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 34.

In some implementations, a bakuchiol-producing enzyme variant as described herein may comprise, or consist, of SEQ ID NO: 35. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 35.

In some implementations, a bakuchiol-producing enzyme variant as described herein may comprise, or consist, of SEQ ID NO: 36. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 36.

In some implementations, a bakuchiol-producing enzyme variant as described herein may comprise, or consist, of SEQ ID NO: 37. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 37.

In some implementations, a bakuchiol-producing enzyme variant as described herein may comprise, or consist, of SEQ ID NO: 38. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 38.

In some implementations, a bakuchiol-producing enzyme variant as described herein may comprise, or consist, of SEQ ID NO: 39. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 39.

In some implementations, a bakuchiol-producing enzyme variant as described herein may comprise, or consist, of SEQ ID NO: 40. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 40.

In some implementations, a bakuchiol-producing enzyme variant as described herein may comprise, or consist, of SEQ ID NO: 41. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 41.

In some implementations, a bakuchiol-producing enzyme variant as described herein may comprise, or consist, of SEQ ID NO: 42. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 42.

In some implementations, a bakuchiol-producing enzyme variant as described herein may comprise, or consist, of SEQ ID NO: 43. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 43.

In some implementations, a bakuchiol-producing enzyme variant as described herein may comprise, or consist, of SEQ ID NO: 44. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 44.

In some implementations, a bakuchiol-producing enzyme variant as described herein may comprise, or consist, of SEQ ID NO: 45. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 45.

In some implementations, a bakuchiol-producing enzyme variant as described herein may comprise, or consist, of SEQ ID NO: 46. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 46.

In some implementations, a bakuchiol-producing enzyme variant as described herein may comprise, or consist, of SEQ ID NO: 47. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 47.

In some implementations, a bakuchiol-producing enzyme variant as described herein may comprise, or consist, of SEQ ID NO: 48. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 48.

In some implementations, a bakuchiol-producing enzyme variant as described herein may comprise, or consist, of SEQ ID NO: 49. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 49.

In some implementations, a bakuchiol-producing enzyme variant as described herein may comprise, or consist, of SEQ ID NO: 50. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 50.

In some implementations, a bakuchiol-producing enzyme variant as described herein may comprise, or consist, of SEQ ID NO: 51. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 51.

In some implementations, a bakuchiol-producing enzyme variant as described herein may comprise, or consist, of SEQ ID NO: 56. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 56.

In some implementations, a bakuchiol-producing enzyme variant as described herein may comprise, or consist, of SEQ ID NO: 57. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 57.

In some implementations, a bakuchiol-producing enzyme variant as described herein may comprise, or consist, of SEQ ID NO: 58. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 58.

In some implementations, a bakuchiol-producing enzyme variant as described herein may comprise, or consist, of SEQ ID NO: 59. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 59.

In some implementations, a bakuchiol-producing enzyme variant as described herein may comprise, or consist, of SEQ ID NO: 60. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 60.

In some implementations, a bakuchiol-producing enzyme variant as described herein may comprise, or consist, of SEQ ID NO: 61. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 61.

In some implementations, a bakuchiol-producing enzyme variant as described herein may comprise, or consist, of SEQ ID NO: 62. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 62.

In some implementations, a bakuchiol-producing enzyme variant as described herein may comprise, or consist, of SEQ ID NO: 63. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 63.

In some implementations, a bakuchiol-producing enzyme variant as described herein may comprise, or consist, of SEQ ID NO: 64. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 64.

In some implementations, a bakuchiol-producing enzyme variant as described herein may comprise, or consist, of SEQ ID NO: 65. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 65.

In some implementations, a bakuchiol-producing enzyme variant as described herein may comprise, or consist, of SEQ ID NO: 66. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 66.

In some implementations, a bakuchiol-producing enzyme variant as described herein may comprise, or consist, of SEQ ID NO: 67. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 667.

In some implementations, a bakuchiol-producing enzyme variant as described herein may comprise, or consist, of SEQ ID NO: 68. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 68.

In some implementations, a bakuchiol-producing enzyme variant as described herein may comprise, or consist, of SEQ ID NO: 69. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 69.

In some implementations, a bakuchiol-producing enzyme variant as described herein may comprise, or consist, of SEQ ID NO: 70. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 70.

In some implementations, a bakuchiol-producing enzyme variant as described herein may comprise, or consist, of SEQ ID NO: 71. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 71.

In some implementations, a bakuchiol-producing enzyme variant as described herein may comprise, or consist, of SEQ ID NO: 72. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 72.

In some implementations, a bakuchiol-producing enzyme variant as described herein may comprise, or consist, of SEQ ID NO: 73. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 73.

In some implementations, a bakuchiol-producing enzyme variant as described herein may comprise, or consist, of SEQ ID NO: 74. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 74.

In some implementations, a bakuchiol-producing enzyme variant as described herein may comprise, or consist, of SEQ ID NO: 75. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 75.

In some implementations, a bakuchiol-producing enzyme variant as described herein may comprise, or consist, of SEQ ID NO: 76. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 76.

In some implementations, a bakuchiol-producing enzyme variant as described herein may comprise, or consist, of SEQ ID NO: 77. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 77.

In some implementations, a bakuchiol-producing enzyme variant as described herein may comprise, or consist, of SEQ ID NO: 78. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 78.

In some implementations, a bakuchiol-producing enzyme variant as described herein may comprise, or consist, of SEQ ID NO: 79. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 79.

In some implementations, a bakuchiol-producing enzyme variant as described herein may comprise, or consist, of SEQ ID NO: 80. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 80.

In some implementations, a bakuchiol-producing enzyme variant as described herein may comprise, or consist, of SEQ ID NO: 81. In some implementations, a bakuchiol-producing enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO: 81.

The present disclosure provides an engineered bakuchiol-producing enzyme comprising at least one amino acid substitution at position 54, 71, 108, 162, 185, 199, 205, 206, 209, 226, 234, 257, 269, 274, 279, 287, 310, 312, 313, 317, 318, 319, 320, 325, 342 or 354 of SEQ ID NO: 3. In some implementations, the engineered bakuchiol-producing enzyme may comprise 2, 3, 4, or 5 or more amino acid substitutions at residues selected from 54, 71, 108, 162, 185, 199, 205, 206, 209, 226, 234, 257, 269, 274, 279, 287, 310, 312, 313, 317, 318, 319, 320, 325, 342, and 354 of SEQ ID NO: 3. In some implementations, the enzyme may comprise at least one amino acid substitution (e.g., 1, 2, 3, 4, 5 or more) selected from the group consisting of E54F, G71D, S108L, T162H, P185V, V199G, P205L, P205V, L206Y, W209S, W209C, W209V, W209T, W209Y, W209R, W209M, W209Q, W209A, W209N, W209D, W209E, W209G, W209H, W209I, W209L, W209K, W209F, W209P, L226M, L234Q, F257E, K269R, I274L, D279C, D279K, D279R, D279M, D279L, M287V, M287F, M287Y, I310V, V312W, V312A, V312F, V312G, V312Y, V312C, V312L, G313I, S317P, S317I, F318R, F318G, L319P, W320D, T325G, S342G, and L354F, relative to SEQ ID NO: 3.

Similarly, the present disclosure provides an engineered enzyme comprising an amino acid sequence that is a variant of SEQ ID NO: 1, wherein the amino acid sequence comprises at least one substitution mutation relative to SEQ ID NO: 1 at one or more amino acid positions selected from 42, 59, 96, 150, 173, 187, 193, 194 197, 214, 222, 245, 257, 262, 267, 275, 298, 300, 301, 305, 306, 307, 308, 313, 330, and 342. In some implementations, the engineered bakuchiol-producing enzyme may comprise 2, 3, 4, or 5 or more amino acid substitutions at residues selected from 42, 59, 96, 150, 173, 187, 193, 194, 197, 214, 222, 245, 257, 262, 267, 275, 298, 300, 301, 305, 306, 307, 308, 313, 330, and 342. The present disclosure also provides an engineered enzyme comprising an amino acid sequence that is a variant of SEQ ID NO: 2, wherein the amino acid sequence comprises at least one substitution mutation relative to SEQ ID NO: 2 at one or more amino acid positions selected from 90, 107, 144, 198, 221, 235, 241, 242, 245, 262, 270, 293, 305, 310, 315, 323, 346, 348, 349, 353, 354, 355, 356, 361, 378, and 390. In some implementations, the engineered bakuchiol-producing enzyme may comprise 2, 3, 4, or 5 or more amino acid substitutions at residues selected from 90, 107, 144, 198, 221, 235, 241, 242, 245, 262, 270, 293, 305, 310, 315, 323, 346, 348, 349, 353, 354, 355, 356, 361, 378, and 390.

The present disclosure and data provided herein indicate that amino acid positions corresponding to residues 42, 59, 96, 150, 173, 187, 193, 194, 197, 214, 222, 245, 257, 262, 267, 275, 298, 300, 301, 305, 306, 307, 308, 313, 330, and 342 of SEQ ID NO: 1 and residues 90, 107, 144, 198, 221, 235, 241, 242, 245, 262, 270, 293, 305, 310, 315, 323, 346, 348, 349, 353, 354, 355, 356, 361, 378, and 390 of SEQ ID NO: 2 are involved in enzymatic function and that substitutions at these residues tend to increase bakuchiol production. Accordingly, the same increase in activity is expected to be observed in other bakuchiol-producing enzymes with shared homology. Accordingly, the present disclosure provides an engineered enzyme that catalyzes production of bakuchiol, exhibits prenyltransferase activity, or both, wherein the engineered enzyme comprises at least one substitution mutation selected from:

(a) substitution of a glutamate (E) corresponding to the E at position 42 of SEQ ID NO: 1 or position 90 of SEQ ID NO: 2

(b) substitution of a glycine (G) corresponding to the G at position 59 of SEQ ID NO: 1 or position 107 of SEQ ID NO: 2;

(c) substitution of a serine (S) corresponding to the S at position 96 of SEQ ID NO: 1 or position 144 of SEQ ID NO: 2;

(d) substitution of threonine (T) corresponding to the T at position 150 of SEQ ID NO: 1 or position 198 of SEQ ID NO: 2;

(e) substitution of proline (P) corresponding to the P at position 173 of SEQ ID NO: 1 or position 221 of SEQ ID NO: 2;
(f) substitution of valine (V) corresponding to the V at position 187 of SEQ ID NO: 1 or position 235 of SEQ ID NO: 2;
(g) substitution of proline (P) corresponding to the P at position 193 of SEQ ID NO: 1 or position 241 of SEQ ID NO: 2;
(h) substitution of leucine (L) corresponding to the L at position 194 of SEQ ID NO: 1 or position 242 of SEQ ID NO: 2;
(i) substitution of tryptophan (W) corresponding to the W at position 197 of SEQ ID NO: 1 or position 245 of SEQ ID NO: 2;
(j) substitution of leucine (L) corresponding to the L at position 214 of SEQ ID NO: 1 or position 262 of SEQ ID NO: 2;
(k) substitution of leucine (L) corresponding to the L at position 222 of SEQ ID NO: 1 or position 270 of SEQ ID NO: 2;
(l) substitution of phenylalanine (F) corresponding to the F at position 245 of SEQ ID NO: 1 or position 293 of SEQ ID NO: 2;
(m) substitution of lysine (K) corresponding to the K at position 257 of SEQ ID NO: 1 or position 305 of SEQ ID NO: 2;
(n) substitution of isoleucine (I) corresponding to the I at position 262 of SEQ ID NO: 1 or position 310 of SEQ ID NO: 2;
(o) substitution of aspartic acid (D) corresponding to the D at position 267 of SEQ ID NO: 1 or position 315 of SEQ ID NO: 2;
(p) substitution of methionine (M) corresponding to the M at position 275 of SEQ ID NO: 1 or position 323 of SEQ ID NO: 2;
(q) substitution of isoleucine (I) corresponding to the I at position 298 of SEQ ID NO: 1 or position 346 of SEQ ID NO: 2;
(r) substitution of valine (V) corresponding to the V at position 300 of SEQ ID NO: 1 or position 348 of SEQ ID NO: 2;
(s) substitution of glycine (G) corresponding to the G at position 301 of SEQ ID NO: 1 or position 349 of SEQ ID NO: 2;
(t) substitution of serine (S) corresponding to the S at position 305 of SEQ ID NO: 1 or position 353 of SEQ ID NO: 2;
(u) substitution of phenylalanine (F) corresponding to the F at position 306 of SEQ ID NO: 1 or position 354 of SEQ ID NO: 2;
(v) substitution of leucine (L) corresponding to the L at position 307 of SEQ ID NO: 1 or position 355 of SEQ ID NO: 2;
(w) substitution of tryptophan (W) corresponding to the W at position 308 of SEQ ID NO: 1 or position 356 of SEQ ID NO: 2;
(x) substitution of threonine (T) corresponding to the T at position 313 of SEQ ID NO: 1 or position 361 of SEQ ID NO: 2;
(y) substitution of serine (S) corresponding to the S at position 330 of SEQ ID NO: 1 or position 378 of SEQ ID NO: 2; and
(z) substitution of leucine (L) corresponding to the L at position 342 of SEQ ID NO: 1 or position 390 of SEQ ID NO: 2. In some implementations, the engineered bakuchiol-producing enzyme may comprise 2, 3, 4, or 5 or more amino acid substitutions. In some implementations, the engineered bakuchiol-producing enzyme may additionally comprise an N-terminal deletion of 1-120 amino acids.

The present disclosure additionally provides an engineered enzyme that catalyzes production of bakuchiol, exhibits prenyltransferase activity, or both, wherein the engineered enzyme comprises at least one substitution mutation selected from:
(a) substitution of phenylalanine (F) at position 42 of SEQ ID NO: 1 or position 90 of SEQ ID NO: 2;
(b) substitution of aspartate (D) at position 59 of SEQ ID NO: 1 or position 107 of SEQ ID NO: 2;
(c) substitution of leucine (L) at position 96 of SEQ ID NO: 1 or position 144 of SEQ ID NO: 2;
(d) substitution of histidine (H) at position 150 of SEQ ID NO: 1 or position 198 of SEQ ID NO: 2;
(e) substitution of valine (V) at position 173 of SEQ ID NO: 1 or position 221 of SEQ ID NO: 2;
(f) substitution of glycine (G) at position 187 of SEQ ID NO: 1 or position 235 of SEQ ID NO: 2;
(g) substitution of leucine (L) or valine (V) at position 193 of SEQ ID NO: 1 or position 241 of SEQ ID NO: 2;
(h) substitution of tyrosine (Y) at position 194 of SEQ ID NO: 1 or position 242 of SEQ ID NO: 2;
(i) substitution of serine (S), cysteine (C), valine (V), threonine (T), tyrosine (Y), arginine (R), methionine (M), or glutamine (Q) at position 197 of SEQ ID NO: 1 or position 245 of SEQ ID NO: 2;
(j) substitution of methionine (M) at position 214 of SEQ ID NO: 1 or position 262 of SEQ ID NO: 2;
(k) substitution of glutamine (Q) at position 222 of SEQ ID NO: 1 or position 270 of SEQ ID NO: 2;
(l) substitution of glutamate (E) at position 245 of SEQ ID NO: 1 or position 293 of SEQ ID NO: 2;
(m) substitution of arginine (R) at position 257 of SEQ ID NO: 1 or position 305 of SEQ ID NO: 2;
(n) substitution of leucine (L) at position 262 of SEQ ID NO: 1 or position 310 of SEQ ID NO: 2;
(o) substitution of cysteine (C), lysine (K), arginine (R), methionine (M), or leucine (L) at position 267 of SEQ ID NO: 1 or position 315 of SEQ ID NO: 2;
(p) substitution of valine (V), phenylalanine (F), or tyrosine (Y) at position 275 of SEQ ID NO: 1 or position 323 of SEQ ID NO: 2;
(q) substitution of valine (V) at position 298 of SEQ ID NO: 1 or position 346 of SEQ ID NO: 2;
(r) substitution of tryptophan (W), alanine (A), phenylalanine (F), glycine (G), tyrosine (Y), cysteine (C), or leucine (L) at position 300 of SEQ ID NO: 1 or position 348 of SEQ ID NO: 2;
(s) substitution of isoleucine (I) at position 301 of SEQ ID NO: 1 or position 349 of SEQ ID NO: 2;
(t) substitution of proline (P) or isoleucine (I) at position 305 of SEQ ID NO: 1 or position 353 of SEQ ID NO: 2;
(u) substitution of arginine (R) or glycine (G) at position 306 of SEQ ID NO: 1 or position 354 of SEQ ID NO: 2;
(v) substitution of proline (P) at position 307 of SEQ ID NO: 1 or position 355 of SEQ ID NO: 2;
(w) substitution of aspartate (D) at position 308 of SEQ ID NO: 1 or position 356 of SEQ ID NO: 2;
(x) substitution of glycine (G) at position 313 of SEQ ID NO: 1 or position 361 of SEQ ID NO: 2;
(y) substitution of glycine (G) at position 330 of SEQ ID NO: 1 or position 378 of SEQ ID NO: 2; and (z) substitution of phenylalanine (F) at position 342 of SEQ ID NO: 1 or position 390 of SEQ ID NO: 2. In some implementations, the engineered bakuchiol-producing enzyme may comprise 2, 3, 4, or 5 or more amino acid substitutions. In some implementations, the engineered bakuchiol-producing enzyme may additionally comprise an N-terminal deletion of 1-120 amino acids.

For the purposes of the present disclosure, it is generally expected that the disclosed engineered bakuchiol-producing enzyme comprise a substitution mutation, an N-terminal deletion, or both that increases catalyzation of production of bakuchiol, prenyltransferase activity, or both, relative to a non-engineered enzyme comprising the same amino acid sequence but without the substitution mutation, N-terminal deletion, or both. For example, an engineered bakuchiol-producing enzyme, as described herein, catalyzes production of bakuchiol, exhibits prenyltransferase activity, or both, and the enzyme comprises nine transmembrane domains and loops connecting the transmembrane domains. However, the engineered enzyme comprises at least one substitution mutation on an internal loop or an external loop of the enzyme. Such an enzyme may further comprise an N-terminus and a C-terminus, and, in some implementations no amino acids are substituted in the first 1-75, 1-50, or 1-25 amino acids of the N-terminus or the last 1-75, 1-50, or 1-25 amino acids of the C-terminus. In some implementations, no amino acids are substituted in the first 50 amino acids of the N-terminus or the last 50 amino acids of the C-terminus. In some implementations, the engineered enzyme may further comprise an N-terminal deletion as described herein.

In some implementations, a variant as described herein exhibits increased bakuchiol-producing activity relative to the wild-type BAK28 (SEQ ID NO: 1) or BAK36 (SEQ ID NO: 2) enzymes, such that its activity is at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about $1^{200}$%, about $1^{300}$%, about $1^{400}$%, about 1500%, about $1^{600}$%, about $1^{700}$%, about $1^{800}$%, about $1^{900}$%, about 2000%, about 2250%, about 2500%, about 2750%, about 3000%, about 3250%, about 3500%, about 3750%, about 4000%, about 4250%, about 4500%, about 4750%, about 5000%, about 10000%, about 100000%, about 1000000%, about 10000000%, or about 20000000% or more than that of the wild-type BAK28 or BAK36 enzymes, as determined by a measure of bakuchiol production or titer.

In some implementations, a variant as described herein exhibits increased bakuchiol-producing activity relative to the wild-type BAK28 (SEQ ID NO: 1) or BAK36 (SEQ ID NO: 2) enzymes, such that its activity is at least about 2-fold—e.g., at least about 4-fold, about 5-fold, about 10-fold, about 18-fold, about 20-fold, about 50-fold, about 100-fold, about 200-fold, about 1000-fold, about 5000-fold, about 10000-fold, about 20000-fold, about 50000-fold, about 100000-fold, about 200000-fold, about 500000-fold, or about 1000000-fold, or more, than that of the wild-type BAK28 or BAK36 enzymes, as determined by a measure of bakuchiol production or titer.

For the purposes of the present disclosure, any of the foregoing enzyme variants can be expressed in a host cell or transgenic cell and any of the foregoing nucleic acids may incorporated into a host cell or transgenic cell in order to produce bakuchiol according to the disclosed methods. Additionally, for the purposes of this disclosure, all of the foregoing enzyme variants can be isolated, in a form in which the protein or enzyme is essentially free of other proteins, contaminants, or macromolecules (e.g., nucleic acids, lipids, etc.).

V. Host Cells and Transgenic Cells

Bioproduction of bakuchiol can rely on a host cell that expresses a bakuchiol-producing protein as disclosed herein or a transgenic cell that expresses a bakuchiol-producing protein as disclosed herein. A host cell may or may not natively express the bakuchiol-producing protein. A transgenic cell may be a cell that comprises a transgene encoding a bakuchiol-producing protein. In some implementations, a transgene encoding a bakuchiol-producing protein may enable the transgenic cell to express a bakuchiol-producing protein, such as a bakuchiol-producing enzyme or enzyme variant disclosed herein.

The present disclosure provides an engineered host cell or a transgenic cell that expresses any of the disclosed bakuchiol-producing proteins. In one aspect, the present disclosure provides a transgenic cell that comprises a transgene encoding any of the disclosed bakuchiol-producing proteins. In some implementations, the engineered host cell or transgenic cell may comprise a bakuchiol-producing protein that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, the engineered host cell or transgenic cell may comprise a bakuchiol-producing protein that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, the bakuchiol-producing protein expressed by the engineered host cell or transgenic cell may share at least 90% identity with SEQ ID NO: 1 or SEQ ID NO: 2. In some implementations, the bakuchiol-producing protein expressed by the engineered host cell or transgenic cell may share at least 95% identity with SEQ ID NO: 1 or SEQ ID NO: 2. In some implementations, the bakuchiol-producing protein expressed by the engineered host cell or transgenic cell may share at least 99% identity with SEQ ID NO: 1 or SEQ ID NO: 2. Thus, this disclosure encompasses expression of proteins with varying degrees of sequence identity compared to SEQ ID NO: 1 and SEQ ID NO: 2, so long as the protein exhibits prenyltransferase activity, catalyzes the production of bakuchiol, or both.

In some implementations, the engineered host cell or transgenic cell may comprise a bakuchiol-producing protein that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations, the bakuchiol-producing protein expressed by the engineered host cell or transgenic cell may share at least 90% identity with SEQ ID NO: 3. In some implementations, the bakuchiol-producing protein expressed by the engineered host cell or transgenic cell may share at least 95% identity with SEQ ID NO: 3. In some implementations, the bakuchiol-producing protein expressed by the engineered host cell or transgenic cell may share at least 99% identity with SEQ ID NO: 3. Thus, this disclosure encompasses expression of proteins with varying degrees of sequence identity compared to SEQ ID NO: 3, so long as the protein exhibits prenyltransferase activity, catalyzes the production of bakuchiol, or both.

In some implementations, an engineered host cell or transgenic cell of the present disclosure can express a bakuchiol-producing protein comprising SEQ ID NO: 1 (i.e., it is 361 amino acids or longer). In some implementations, an engineered host cell or transgenic cell of the present disclosure can express a bakuchiol-producing protein comprising 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, an engineered host cell or transgenic cell of the present disclosure can express a bakuchiol-producing protein consisting of SEQ ID NO: 1. In some implementations, an engineered host cell or transgenic cell of the present disclosure can express a bakuchiol-producing protein consisting of 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, an engineered host cell or transgenic cell of the present disclosure can express a bakuchiol-producing protein comprising about 365, about 370, about 375, about 380, about 385, about 390, about 395, about 400, about 405, about 410, about 415, about 420, about 425, about 430, about 435, about 440, or about 450 amino acids, wherein at least about 361 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein comprising SEQ ID NO: 2 (i.e., it is 409 amino acids or longer). In some implementations, an engineered host cell or transgenic cell of the present disclosure can express a bakuchiol-producing protein comprising 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, an engineered host cell or transgenic cell of the present disclosure can express a bakuchiol-producing protein consisting of SEQ ID NO: 2. In some implementations, an engineered host cell or transgenic cell of the present disclosure can express a bakuchiol-producing protein consisting of 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, an engineered host cell or transgenic cell of the present disclosure can express a bakuchiol-producing protein comprising about 410, about 415, about 420, about 425, about 430, about 435, about 440, or about 450 amino acids, wherein at least about 409 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein that is shorter than SEQ ID NO: 1 or SEQ ID NO: 2. For example, the expressed bakuchiol-producing protein may be less than 409 or less than 361 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein comprising SEQ ID NO: 3 (i.e., it is 373 amino acids or longer). In some implementations, an engineered host cell or transgenic cell of the present disclosure can express a bakuchiol-producing protein comprising 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations, an engineered host cell or transgenic cell of the present disclosure can express a bakuchiol-producing protein consisting of SEQ ID NO: 3. In some implementations, an engineered host cell or transgenic cell of the present disclosure can express a bakuchiol-producing protein consisting of 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations, an engineered host cell or transgenic cell of the present disclosure can express a bakuchiol-producing protein comprising about 370, about 375, about 380, about 385, about 390, about 395, about 400, about 405, about 410, about 415, about 420, about 425, about 430, about 435, about 440, or about 450 amino acids, wherein at least about 373 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein that is shorter than SEQ ID NO: 3. For example, the expressed bakuchiol-producing protein may be less than 373 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein comprising any one of SEQ ID NO: 4-51 and 56-81 (i.e., it is 373 amino acids or longer). In some implementations, an engineered host cell or transgenic cell of the present disclosure can express a bakuchiol-producing protein comprising 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations, an engineered host cell or transgenic cell of the present disclosure can express a bakuchiol-producing protein consisting of any one of SEQ ID NO: 4-51 and 56-81. In some implementations, an engineered host cell or transgenic cell of the present disclosure can express a bakuchiol-producing protein consisting of 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations, an engineered host cell or transgenic cell of the present disclosure can express a bakuchiol-producing protein comprising about 370, about 375, about 380, about 385, about 390, about 395, about 400, about 405, about 410, about 415, about 420, about 425, about 430, about 435, about 440, or about 450 amino acids, wherein at least about 373 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. Varying degrees of sequence identity and coverage are acceptable and are included as part of the implementations herein, so long as the protein exhibits prenyltransferase activity, catalyzes the production of bakuchiol, or both.

In some implementations, an engineered host cell or transgenic cell of the present disclosure can express a bakuchiol-producing protein that is shorter than any one of SEQ ID NO: 4-51 and 56-81. For example, the expressed bakuchiol-producing protein may be less than 373 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. Varying degrees of sequence identity and coverage are acceptable and are included as part of the implementations herein, so long as the protein exhibits prenyltransferase activity, catalyzes the production of bakuchiol, or both.

Various prokaryotic and eukaryotic expression systems are commonly used for bioproduction, though factors including the growth conditions, type of fermenter utilized, toxicity (if any) of the product, and other metabolic considerations of the microbe producing the product of interest may be employed to select a suitable system. Thus, in some implementations, a host cell or a transgenic cell suitable for expressing the disclosed bakuchiol-producing proteins may be a prokaryote. In in some implementations, a host cell or a transgenic cell suitable for expressing the disclosed bakuchiol-producing proteins may be a eukaryote.

In some implementations, the engineered host cell or transgenic cell is a prokaryote. Model prokaryotic systems that may be utilized as a transgenic cell include but are not limited to *Escherichia coli* (*E. coli*), an *Acinetobacter* species, a *Pseudomonas* species, a *Streptomyces* species, and a *Mycobacterium* species. Additional suitable prokaryotic expression systems include, but are not limited to, *Klebsiella, Lactococcus, Mannheimia, Corynebacterium, Vibrio*, and *Bacillis*.

In some implementations, the engineered host cell or transgenic cell is a eukaryote. Model eukaryotic systems that may be utilized as a transgenic cell include but are not limited to *Saccharomyces cerevisiae* (*S. cerevisiae*) or other yeast species; a filamentous fungi, optionally selected from an *Aspergillus* species and a *Trichoderma* species; an algae, optionally selected from *Botryococcus braunii, Chlorella* sp., *Crypthecodinium cohnii, Cylindrotheca* sp., *Nitzschia* sp., *Phaeodactylum tricornutum, Schizochytrium* sp., and *Tetraselmis suecia*; and an amoeba, which is optionally *Dictyostelium discoideum*. Additional suitable eukaryotic expression systems include, but are not limited to, *Pichia pastoris, Yarrowia lipolytica, Kluyveromyces marxianus, Rhodosporidium toruloides. Aspergillus* (*oryzae, nidulans, niger*), *Trichoderma reesei*, and *Penicillium chrysogenum*.

In some implementations, for the engineered host cells and transgenic cells of the present disclosure bakuchiol is produced when the cell is cultured in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii) thereof. The amount of bakuchiol produced may vary. For example, an engineered host cell or a transgenic cell of the present disclosure may produce at least about 0.1 µg/L—e.g., at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least about 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more, of bakuchiol within about 48 hours of culture. Longer or shorter periods of culture time are also possible. For the purposes of the disclosed compositions and methods, it is understood that in some implementations p-coumaric acid, GPP, DMAPP, IPP, or all or a combination thereof may be produced endogenously by the host cell or transgenic cell, and do not require exogenous addition into, for example, the cell culture medium. In some implementations, exogenous p-coumaric acid, GPP, DMAPP, IPP, or all or a combination thereof may be added to the culture medium.

As noted above, in implementations involving a transgenic cell (e.g., *S. cerevisiae* or *E. coli*), the transgenic cell will comprise a transgene encoding the bakuchiol-producing protein, and the transgene can be integrated into the transgenic cell's genome. The transgene may be integrated within an expression cassette that appropriately drives expression of the bakuchiol-producing protein. For those implementations in which genome integration of the transgene is preferred or desired, known methods of integration can be used, including but not limited to Cas-based systems (e.g., Cas9, Cas12, etc.), homologous recombination, gene gun, conjugation protocols, lambda red, etc. Alternatively, in some implementations, the transgene may not be integrated into the genome, and instead may express the bakuchiol-producing protein from, for example, a plasmid or similar vector.

An expression cassette or vector for expressing the transgene may comprise a promoter and a terminator. Suitable promoters that can be used may include but are not limited to GAL1, TEF2, TEF1, TDH3, ENO2, CCW12, EF-1a promoter, CMV immediate early, HSV thymidine kinase, early and late SV40, LTRs from retrovirus, and mouse metallothionein-I. In some implementations, the promoter is GAL1. In some implementations, an inducible or repressible promoter, such as GAL1, GAL2, GAL7, GAL10, CUP1, MET3, MET17, or MET25, may be used. Inducible promoters operably link the expression of a target gene (e.g., the nucleic acid sequence encoding a bakuchiol-producing protein) to a specific signal or a particular biotic or abiotic factor. Types of inducible promoters that may be utilized in the disclosed include, but are not limited to, chemically-inducible promoters (i.e., antibiotics, steroids, metals, etc.), light-inducible promoters, heat-inducible promoters, and hypoxia-inducible promoters. Transcription terminators that may be used are also known in the art (see Bittner et al., Methods in Enzymol. 153: 516-544 (1987)), and include but are not limited to GAT2, Rho-dependent terminators, Rho-independent terminators, poly-A sequences, and the like. In some implementations, the terminator is GAT2.

VI. Methods of Bioproduction and Batches Produced Therefrom

The identification, isolation, and characterization of previously unknown bakuchiol-producing prenyltransferase enzymes allows methods of bioproduction of bakuchiol. Thus, the present disclosure provides methods of producing bakuchiol, comprising culturing an engineered host cell or a transgenic cell disclosed herein in a culture medium and in the presence of p-coumaric acid and geranyl pyrophosphate (GPP), dimethylallyl pyrophosphate (DMAPP), isopentenyl pyrophosphate (IPP), or any combination of GPP, DMAPP, and IPP. For the purposes of the disclosed methods, it is understood that in some implementations p-coumaric acid, GPP, DMAPP, IPP, or all or a combination thereof may be produced endogenously by the host cell or transgenic cell, and do not require exogenous addition into, for example, the cell culture medium. In some implementations, exogenous p-coumaric acid, GPP, DMAPP, IPP, or all or a combination thereof may be added to the culture medium.

In some implementations, the methods comprise culturing a transgenic cell (e.g., S. cerevisiae or E. coli) comprising a transgene that encodes a bakuchiol-producing protein that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1; or at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2; or at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3; or at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations, the bakuchiol-producing protein expressed by the transgenic cell may share at least 90% identity with SEQ ID NO: 1, SEQ ID NO: 2, SEQ ID NO: 3, or any one of SEQ ID NO: 4-51 and 56-81. In some implementations, the bakuchiol-producing protein expressed by the transgenic cell may share at least 95% identity with SEQ ID NO: 1, SEQ ID NO: 2, SEQ ID NO: 3, or any one of SEQ ID NO: 4-51 and 56-81. In some implementations, the bakuchiol-producing protein expressed by the transgenic cell may share at least 99% identity with SEQ ID NO: 1, SEQ ID NO: 2, SEQ ID NO: 3, or any one of SEQ ID NO: 4-51 and 56-81. Thus, the protein may possess varying degrees of sequence identity compared to SEQ ID NOs: 1-41, so long as the protein exhibits prenyltransferase activity, catalyzes the production of bakuchiol, or both.

In some implementations, the methods comprise culturing a transgenic cell comprising a transgene encoding a bakuchiol-producing protein comprising SEQ ID NO: 1 (i.e., it is 361 amino acids or longer). In some implementations, the methods comprise culturing a transgenic cell comprising a transgene encoding a bakuchiol-producing protein comprising 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, the methods comprise culturing a transgenic cell comprising a transgene encoding a bakuchiol-producing protein consisting of SEQ ID NO: 1. In some implementations, the methods comprise culturing a transgenic cell comprising a transgene encoding a bakuchiol-producing protein consisting of 361 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. In some implementations, the methods comprise culturing a transgenic cell comprising a transgene encoding a bakuchiol-producing protein comprising about 365, about 370, about 375, about 380, about 385, about 390, about 395, about 400, about 405, about 410, about 415, about 420, about 425, about 430, about 435, about 440, or about 450 amino acids, wherein at least about 361 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein comprising SEQ ID NO: 2 (i.e., it is 409 amino acids or longer). In some implementations, the methods comprise culturing a transgenic cell comprising a transgene encoding a bakuchiol-producing protein comprising 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, the methods comprise culturing a transgenic cell comprising a transgene encoding a bakuchiol-producing protein consisting of SEQ ID NO: 2. In some implementations, the methods comprise culturing a transgenic cell comprising a transgene encoding a bakuchiol-producing protein consisting of 409 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. In some implementations, the methods comprise culturing a transgenic cell comprising a transgene encoding a bakuchiol-producing protein comprising about 410, about 415, about 420, about 425, about 430, about 435, about 440, or about 450 amino acids, wherein at least about 409 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 2. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein comprising SEQ ID NO: 3 (i.e., it is 373 amino acids or longer). In some implementations, the methods comprise culturing a transgenic cell comprising a transgene encoding a bakuchiol-producing protein comprising 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations, the methods comprise culturing a transgenic cell comprising a transgene encoding a bakuchiol-producing protein consisting of SEQ ID NO: 3. In some implementations, the methods comprise culturing a transgenic cell comprising a transgene encoding a bakuchiol-producing protein consisting of 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations, the methods comprise culturing a transgenic cell comprising a transgene encoding a bakuchiol-producing protein comprising about 375, about 380, about 385, about 390, about 395, about 400, about 405, about 410, about 415, about 420, about 425, about 430, about 435, about 440, or about 450 amino acids, wherein at least about 373 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein comprising any one of SEQ ID NO: 4-51 and 56-81 (i.e., it is 373 amino acids or longer). In some implementations, the methods comprise culturing a transgenic cell comprising a transgene encoding a bakuchiol-producing protein comprising 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations, the methods comprise culturing a transgenic cell comprising a transgene encoding a bakuchiol-producing protein consisting of any one of SEQ ID NO: 4-51 and 56-81. In some implementations, the methods comprise culturing a transgenic cell comprising a transgene encoding a bakuchiol-producing protein consisting of 373 amino acids that have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations, the methods comprise culturing a transgenic cell comprising a transgene encoding a bakuchiol-producing protein comprising about 375, about 380, about 385, about 390, about 395, about 400, about 405, about 410, about 415, about 420, about 425, about 430, about 435, about 440, or about 450 amino acids, wherein at least about 373 amino acids of the protein have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein that is shorter than SEQ ID NO: 1 or SEQ ID NO: 2. For example, the expressed bakuchiol-producing protein may be less than 409 or less than 361 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 1 or SEQ ID NO: 2. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein that is shorter than SEQ ID NO: 3. For example, the expressed bakuchiol-producing protein may be less than 373 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with SEQ ID NO: 3. Varying degrees of sequence identity and coverage may be employed, so long as the protein exhibits prenyltransferase activity, catalyzes the production of bakuchiol, or both.

In some implementations, the methods comprise culturing a transgenic cell comprising a transgene encoding a bakuchiol-producing protein that is shorter than any one of SEQ ID NO: 4-51 and 56-81. For example, the expressed bakuchiol-producing protein may be less than 373 amino acids in length, so long as the protein has a catalytic domain that has at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. In some implementations at least about 50, at least about 75, at least about 100, at least about 125, at least about 150, at least about 175, at least about 200, at least about 225, at least about 250, at least about 275, at least about 300, at least about 325, or at least about 350 amino acids of the protein can have at least about 65%—e.g., at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100%, or any values in between any of the two aforementioned values, identity with any one of SEQ ID NO: 4-51 and 56-81. Varying degrees of sequence identity and coverage may be employed, so long as the protein exhibits prenyltransferase activity, catalyzes the production of bakuchiol, or both.

Various prokaryotic and eukaryotic expression systems can be utilized for the disclosed methods. In some implementations, the microbial cell used in the methods may be a prokaryote, including but are not limited to *Escherichia coli* (*E. coli*), an *Acinetobacter* species, a *Pseudomonas* species, a *Streptomyces* species, and a *Mycobacterium* species. Additionally suitable prokaryotic expression systems include, but are not limited to, *Klebsiella, Lactococcus, Mannheimia, Corynebacterium, Vibrio*, and *Bacillis*. In in some implementations, the transgenic cell used in the methods may be a eukaryote, including but are not limited to *Saccharomyces cerevisiae* (*S. cerevisiae*) or other yeast species; a filamentous fungi, optionally selected from an *Aspergillus* species and a *Trichoderma* species; an algae, optionally selected from *Botryococcus braunii, Chlorella* sp., *Crypthecodinium cohnii, Cylindrotheca* sp., *Nitzschia* sp., *Phaeodactylum tricornutum, Schizochytrium* sp., and *Tetraselmis suecia*; and an amoeba, which is optionally *Dictyostelium discoideum*. Additional suitable eukaryotic expression systems include, but are not limited to, *Pichia pastoris, Yarrowia lipolytica, Kluyveromyces marxianus, Rhodosporidium toruloides. Aspergillus* (*oryzae, nidulans, niger*), *Trichoderma reesei*, and *Penicillium chrysogenum*.

The disclosed methods can be carried out in a bioproduction reactor, fermentation tank, culture flask, or other suitable containers for bioproduction. Various different culture mediums can be selected based on the particular transgenic species used and the growth conditions, among other things. In some implementations, minimal culture medium may be supplemented as needed to optimize growth and production of a given transgenic cell type. For example, in some implementations, such as those utilizing transgenic *S. cerevisiae*, the culture medium may comprise about 3% w/v maltodextrin, about 0.2% w/v glucose, alpha-amylase, or any combination thereof.

As discussed above, and without being bound by any particular theory, it is believed that bioproduction of bakuchiol is catalyzed through a mechanism involved p-coumaric acid and geranyl pyrophosphate (GPP), dimethylallyl pyrophosphate (DMAPP), isopentenyl pyrophosphate (IPP), or any combination of GPP, DMAPP, and IPP. Thus, in some implementations the culture medium used for the disclosed methods may optionally include some p-coumaric acid to supplement that which is endogenously produced by a given transgenic cell or host cell. Indeed, In some implementations p-coumaric acid may be produced endogenously by the host cell or transgenic cell and the culture medium is not supplemented. In some implementations, the culture medium may comprise at least about 1.50 mM p-coumaric acid—e.g., at least about 1.75 mM p-coumaric acid, at least about 2.00 p-coumaric acid, at least about 2.25 mM p-coumaric acid, at least about 2.50 mM p-coumaric acid, at least about 2.75 mM p-coumaric acid, at least about 3.00 p-coumaric acid, at least about 3.25 mM p-coumaric acid, at least about 3.50 mM p-coumaric acid, at least about 3.75 mM p-coumaric acid, at least about 4.00 p-coumaric acid, or more.

The disclosed methods are the first to achieve production of bakuchiol in by a transgenic organism. These methods of bioproduction may be further optimized and developed to increase yield. For example, in some implementations, the disclosed methods may produce at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 3.5 µg/L, at least about 4.0 µg/L, at least about 4.5 µg/L, at least about 5.0 µg/L, at least about 5.5 µg/L, at least about 6.0 µg/L, at least about 6.5 µg/L, at least about 7.0 µg/L, at least about 7.5 µg/L, at least about 8.0 µg/L, at least about 8.5 µg/L, at least about 9.0 µg/L, at least about 9.5 µg/L, at least about 10.0 µg/L, at least about 20 µg/L, at least about 30 µg/L, at least about 40 µg/L, at least about 50 µg/L, at least about 75 µg/L, at least about 100 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 6 hours, at least about 12 hours, at least about 18 hours, at least about 24 hours, at least about 36 hours, or at least about 48 hours of culture. In some implementations, the disclosed methods may produce at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 3.5 µg/L, at least about 4.0 µg/L, at least about 4.5 µg/L, at least about 5.0 µg/L, at least about 5.5 µg/L, at least about 6.0 µg/L, at least about 6.5 µg/L, at least about 7.0 µg/L, at least about 7.5 µg/L, at least about 8.0 µg/L, at least about 8.5 µg/L, at least about 9.0 µg/L, at least about 9.5 µg/L, at least about 10.0 µg/L, at least about 20 µg/L, at least about 30 µg/L, at least about 40 µg/L, at least about 50 µg/L, at least about 75 µg/L, at least about 100 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within about 6 hours of culture or less, about 12 hours of culture or less, about 18 hours of culture or less, about 24 hours of culture or less, about 36 hours of culture or less, or about 48 hours of culture or less.

The disclosed methods are the first to provide a process of bioproducing bakuchiol in batches that can be used for commercial consumption. This, the present disclosure provides batches of bakuchiol produced by the methods disclosed herein. A bioproduction batch of bakuchiol may have a chemical purity of at least 90%, at least 91%, at least 92%, at least 93%, at least 94%, at least 95%, at least 96%, at least 97%, at least 98%, at least 99%, or 100%, or any values in between any of the two aforementioned values, and no single impurity of greater than 1%, no greater than about 0.5%, or greater than about 0.1%. The level of impurities in a given batch of bakuchiol can be determined by high-performance liquid chromatography (HPLC) and other suitable techniques.

The physical state of the bakuchiol batch can vary as need and depending on the stage of the production process, and the disclosed batches may be solid or liquid. Liquid batches of bakuchiol may be in the form of a non-aqueous solution, such as an oil, an organic solvent, or an aqueous solution. The concentration of bakuchiol in a liquid batch (e.g., in an oil or aqueous solution) may be at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 3.5 µg/L, at least about 4.0 µg/L, at least about 4.5 µg/L, at least about 5.0 µg/L, at least about 5.5 µg/L, at least about 6.0 µg/L, at least about 6.5 µg/L, at least about 7.0 µg/L, at least about 7.5 µg/L, at least about 8.0 µg/L, at least about 8.5 µg/L, at least about 9.0 µg/L, at least about 9.5 µg/L, at least about 10.0 µg/L, at least about 20.0 µg/L, at least about 30.0 µg/L, at least about 40.0 µg/L, at least about 50.0 µg/L, at least about 75.0 µg/L, at least about 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more.

VII. Detection and Quantitation of Bakuchiol

The present disclosure provides methods of detecting bakuchiol and methods of quantifying bakuchiol using analytic techniques, including mass spectrometry. These methods may be useful for quality control of bakuchiol production by the disclosed bioproduction methods and any other known techniques of bakuchiol synthesis, extraction, or isolation.

In one implementation, bakuchiol can be detected by liquid chromatography mass spectrometry (LCMS) using, for example, an Agilent 1290 UHPLC and a 6460 triple-quadrupole mass spectrometer. Quantitation and compound identity can be determined by using an external standard curve of an authentic sample of bakuchiol.

Aqueous samples of bakuchiol can be diluted with isopropyl alcohol. In one implementation, the additional of isopropyl alcohol is not a purification process, per se, and the sample remains a 1-phase solution. However, the isopropyl alcohol may be extracting bakuchiol from hydrophobic surfaces such as lab ware and cellular membranes. The isopropyl alcohol may also help to clean the sample by precipitating proteins and other interfering material.

Beyond the addition of isopropyl alcohol, additional optional preparation processes include, but are not limited to extracting bakuchiol from the sample and centrifuging the sample to obtain a bakuchiol-containing supernatant.

Samples can be separated on a Waters BEH 50 mm×2.1 mM column, heated to 70° C., using water and acetonitrile mobile phases with a flow rate of 0.5 mL/min. The gradient may comprise of the following: 0 minutes 0% B, 1 minutes 99% B, 2 minutes 99% B, and 2.1 minutes 0% B. The gradient can utilize a linear ramp for transitions, and the process can be about 3 minutes long—e.g., about 2 minutes, about 2.5 minutes about 3 minutes, about 3.5 minutes, or about 4 minutes. A specific MRM can be used to detect bakuchiol in the mass spectrometry with an ESI source in the negative ion mode: Parent 255.2 m/z (unit), Product 172.1 m/z, Fragmenter 120V, Collision Energy 20 V, Cell Accelerator Voltage 5V with a 300 ms dwell time. Optical detection can also conducted at 260 nm with a 0.5 s response time.

Beyond this implementation, the present disclosure provides methods for determining an amount of bakuchiol in a sample by mass spectrometry, the method comprising:
(i) ionizing bakuchiol from the sample to generate one or more ions detectable by mass spectrometry;
(ii) determining an amount of bakuchiol ions by multiple reaction or high resolution accurate mass mass spectrometry; and
(iii) relating the amount of bakuchiol ions to the amount of bakuchiol in the sample, wherein a limit of detection of the method for bakuchiol is between about 0.001 μg/L and 0.0001 μg/L.

Various methods of ionization are known and can be utilized. For example, ionizing can comprise atmospheric pressure chemical ionization (APCI), electrospray ionization (ESI), or, if paired with gas chromatography, electron impact (EI) ionization Both APCI and ESI can be performed in negative ionization mode or positive ionization mode.

In some implementations, when using ESI in negative ion mode, the one or more ions (e.g., daughter ions after collision activation) may comprise an ion with a mass to charge ratio (m/z) of 172.1±0.5.

Prior to ionization, various methods of chromatography can be performs to isolate the bakuchiol and increase the sensitivity and selectivity of the mass spectroscopy. The chromatography may be liquid chromatography (LC) or gas chromatography (GC). prior to ionizing, the sample is subjected to liquid chromatography. Exemplary forms of LC that can be utilized include, but are not limited to, high performance liquid chromatography (HPLC), ultra performance liquid chromatography (UPLC), ultra high performance liquid chromatography (UHPLC), and supercritical fluid chromatography (SFC).

As discussed above, optional preparation processes that may be performed prior to ionizing, include diluting the sample with an alcohol (e.g., isopropyl alcohol), extracting the bakuchiol from the sample, centrifuging the sample to obtain the supernatant, or a combination thereof.

VIII. Examples of Implementations of the Present Disclosure

Implementation 1. A transgenic cell, comprising a transgene encoding a transgenic protein comprising an amino acid sequence with at least about 65% identity to: SEQ ID NO: 1 or 2; wherein the transgenic protein catalyzes the production of bakuchiol, exhibits prenyltransferase activity, or both.

Implementation 2. The transgenic cell of Implementation 1, wherein the transgenic protein comprises an amino acid sequence with at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1 or SEQ ID NO: 2.

Implementation 3. The transgenic cell of Implementation 1 or 2, wherein the transgenic cell is prokaryotic.

Implementation 4. The transgenic cell of any one of Implementations 1-3, wherein the transgenic cell is selected from *Escherichia coli* (*E. coli*), an *Acinetobacter* species, a *Pseudomonas* species, a *Streptomyces* species, and a *Mycobacterium* species.

Implementation 5. The transgenic cell of Implementation 1 or 2, wherein the transgenic cell is eukaryotic.

Implementation 6. The transgenic cell of any one of Implementations 1, 2, or 5, wherein the transgenic cell is selected from *Saccharomyces cerevisiae* (*S. cerevisiae*) or other yeast species, a filamentous fungi, an algae, and an amoeba.

Implementation 7. The transgenic cell of Implementation 6, wherein the filamentous fungi is selected from an *Aspergillus* species and a *Trichoderma* species.

Implementation 8. The transgenic cell of Implementation 6, wherein the amoeba is *Dictyostelium discoideum*.

Implementation 9. The transgenic cell of Implementation 6, wherein the algae is selected from *Botryococcus braunii*, *Chlorella* sp., *Crypthecodinium cohnii*, *Cylindrotheca* sp., *Nitzschia* sp., *Phaeodactylum tricornutum*, *Schizochytrium* sp., and *Tetraselmis suecia*.

Implementation 10. The transgenic cell of any one of Implementations 1-9, wherein bakuchiol is produced when the transgenic cell is cultured in presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 11. The transgenic cell of any one of Implementations 1-10, wherein the transgenic cell produces at least about 0.1 μg/L, at least about 0.2 μg/L, at least about 0.3 μg/L, at least about 0.4 μg/L, at least about 0.5 μg/L, at least about 0.6 μg/L, at least about 0.7 μg/L, at least about 0.8 μg/L, at least about 0.9 μg/L, at least about 1.0 μg/L, at least about 1.1 μg/L, at least about 1.2 μg/L, at least about 1.3 μg/L, at least about 1.4 μg/L, at least about 1.5 μg/L, at least about 1.6 μg/L, at least about 1.7 μg/L, at least about 1.8 μg/L, at least about 1.9 μg/L, at least about 2.0 μg/L, at least about 2.1 μg/L, at least about 2.2 μg/L, at least about 2.3 μg/L, at least about 2.4 μg/L, at least about 2.5 μg/L, at least about 3.0 μg/L, at least about 4.0 μg/L, at least about 5.0 μg/L, at least about 10.0 μg/L, at least about 15.0 μg/L, at least about 20.0 μg/L, at least about 25.0 μg/L, at least about 30.0 μg/L, at least about 35.0 μg/L, at least about 40.0 μg/L, at least about 45.0 μg/L, at least about 50.0 μg/L, at least 100.0 μg/L, at least about 150.0 μg/L, at least about 200.0 μg/L, at least about 250.0 μg/L, at least about 300.0 μg/L, at least about 350.0 μg/L, at least about 400.0 μg/L, at least about 450.0 μg/L, at least about 500.0 μg/L, at least about 600.0 μg/L, at least about 700.0 μg/L, at least about 800.0 μg/L, at least about 900.0 μg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours when cultured in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 12. The transgenic cell of any one of Implementations 1-11, wherein the transgene is integrated into the transgenic cell's genome.

Implementation 13. The transgenic cell of any one of Implementations 1-11, wherein the transgene is not integrated into the transgenic cell's genome.

Implementation 14. The transgenic cell of any one of Implementations 1-13, wherein expression of the transgene is driven by a GAL 1 promoter.

Implementation 15. The transgenic cell of any one of Implementations 1-13, wherein expression of the transgene is driven by an inducible promoter.

Implementation 16. The transgenic cell of any one of Implementations 1-15, the transgenic protein has at least about 90% identity to SEQ ID NO: 1 or SEQ ID NO: 2.

Implementation 17. The transgenic cell of any one of Implementations 1-16, wherein the transgenic protein comprises SEQ ID NO: 1 or SEQ ID NO: 2.

Implementation 18. The transgenic cell of any one of Implementations 1-16, wherein the transgenic protein consists of SEQ ID NO: 1 or SEQ ID NO: 2.

Implementation 19. A method of producing bakuchiol, comprising culturing the transgenic cell according to one of Implementations 1-18 in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 20. The method of Implementation 19, wherein the culture medium further comprises about 3% w/v maltodextrin, about 0.2% w/v glucose, alpha-amylase, or any combination thereof.

Implementation 21. The method of Implementation 19 or 20, wherein the culture medium comprises at least about 1.50 mM p-coumaric acid, at least about 1.75 mM p-coumaric acid, at least about 2.00 p-coumaric acid, at least about 2.25 mM p-coumaric acid, at least about 2.50 mM p-coumaric acid, at least about 2.75 mM p-coumaric acid, at least about 3.00 p-coumaric acid, at least about 3.25 mM p-coumaric acid, at least about 3.50 mM p-coumaric acid, at least about 3.75 mM p-coumaric acid, at least about 4.00 p-coumaric acid or more.

Implementation 22. The method of any one of Implementations 19-20, wherein the culture medium does not comprise exogenous p-coumaric acid, GPP, DMAPP, IPP, or any combination thereof.

Implementation 23. The method of any one of Implementations 19-22, wherein at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours of culture.

Implementation 24. A bioproduction batch of bakuchiol, wherein the bakuchiol has a chemical purity of at least about 90%, at least about 91%, at least about 92%, at least about 93%, at least about 94%, at least about 95%, at least about 96%, at least about 97%, at least about 98%, at least about 99%, or 100%, and no single impurity of greater than about 1%.

Implementation 25. The bioproduction batch of bakuchiol of Implementation 24, wherein the bakuchiol is in an oil.

Implementation 26. The bioproduction batch of bakuchiol of Implementation 24, wherein the bakuchiol is in an aqueous solution.

Implementation 27. The bioproduction batch of bakuchiol of Implementation 25 or 26, wherein the concentration of bakuchiol is at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least about 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more.

Implementation 28. The bioproduction batch of bakuchiol of any one of Implementations 24-27, wherein the bakuchiol is produced by the method according to any one of Implementations 19-23.

Implementation 29. An isolated protein comprising an amino acid sequence with at least about 65% identity to: SEQ ID NO: 1 or 2.

Implementation 30. The isolated protein of Implementation 29, wherein the amino acid sequence comprises at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity with SEQ ID NO: 1 or SEQ ID NO: 2.

Implementation 31. The isolated protein of Implementation 29 or 30, wherein the amino acid sequence has at least 90% identity to SEQ ID NO: 1 or SEQ ID NO: 2.

Implementation 32. The isolated protein of Implementation 29, wherein the amino acid sequence comprises or consists of SEQ ID NO: 1 or SEQ ID NO: 2.

Implementation 33. The isolated protein of Implementation 29, wherein the amino acid sequence consists of SEQ ID NO: 1 or SEQ ID NO: 2.

Implementation 34. The isolated protein of any one of Implementations 29-33, wherein the isolated protein exhibits prenyltransferase activity.

Implementation 35. The isolated protein of any one of Implementations 29-34, wherein the isolated protein catalyzes the production of bakuchiol.

Implementation 36. A nucleic acid comprising a nucleic acid sequence encoding the isolated protein of any one of Implementations 29-35.

Implementation 37. An isolated host cell that produces the isolated protein of any one of Implementations 29-35 or that comprises the nucleic acid of Implementation 36.

Implementation 38. A bakuchiol-producing enzyme as disclosed herein.

Implementation 39. A transgenic cell capable of producing bakuchiol as disclosed herein.

Implementation 40. A method of producing bakuchiol as disclosed herein.

Implementation 41. A method for determining an amount of bakuchiol in a sample by mass spectrometry, the method comprising:
(i) ionizing bakuchiol from the sample to generate one or more ions detectable by mass spectrometry;
(ii) determining an amount of bakuchiol ions by multiple reaction or high resolution accurate mass spectrometry; and
(iii) relating the amount of bakuchiol ions to the amount of bakuchiol in the sample, wherein a limit of detection of the method for bakuchiol is between about 0.001 μg/L and 0.0001 μg/L.

Implementation 42. The method of Implementation 41, wherein ionizing comprises atmospheric pressure chemical ionization (APCI).

Implementation 43. The method of Implementation 42, wherein the APCI is in negative ionization mode or positive ionization mode.

Implementation 44. The method of Implementation 41, wherein ionizing comprises electrospray ionization (ESI).

Implementation 45. The method of Implementation 44, wherein the ESI is in negative ionization mode or positive ionization mode.

Implementation 46. The method of Implementation 44 or 45, wherein the one or more ions comprise an ion with a mass to charge ratio (m/z) of 172.1±0.5 or a parent ion with a mass to charge ratio (m/z) of about 255 in negative mode or about 257 in positive mode.

Implementation 47. The method of any one of Implementations 41-46, wherein prior to ionizing, the sample is subjected to liquid chromatography.

Implementation 48. The method of Implementation 47, wherein the liquid chromatography is selected from high performance liquid chromatography (HPLC), ultra performance liquid chromatography (UPLC), ultra high performance liquid chromatography (UHPLC), and supercritical fluid chromatography (SFC).

Implementation 49. The method of Implementation 41, where ionizing comprises electron impact (EI) ionization.

Implementation 50. The method of any one of Implementations 41-43 or 49, wherein prior to ionizing, the sample is subjected to gas chromatography (GC).

Implementation 51. The method of any one of Implementations 41-50, wherein prior to ionizing, the sample is diluted with an alcohol, extracted, centrifuged, or any combination thereof.

Implementation 52. The method of any one of Implementations 41-51, wherein the sample is obtained from a bioproduction batch of bakuchiol.

Implementation 53. The method of Implementation 52, wherein the bakuchiol has a chemical purity of at least about 90%, at least about 91%, at least about 92%, at least about 93%, at least about 94%, at least about 95%, at least about 96%, at least about 97%, at least about 98%, at least about 99%, or 100%, and no single impurity of greater than about 1%.

Implementation 54. The method of Implementation 52 or 53, wherein the bakuchiol is in an oil.

Implementation 55. The method of Implementation 52 or 53, wherein the bakuchiol is in an aqueous solution.

Implementation 56. The method of Implementation 54 or 55, wherein the concentration of bakuchiol is at least about 0.1 μg/L, at least about 0.2 μg/L, at least about 0.3 μg/L, at least about 0.4 μg/L, at least about 0.5 μg/L, at least about 0.6 μg/L, at least about 0.7 μg/L, at least about 0.8 μg/L, at least about 0.9 μg/L, at least about 1.0 μg/L, at least about 1.1 μg/L, at least about 1.2 μg/L, at least about 1.3 μg/L, at least about 1.4 μg/L, at least about 1.5 μg/L, at least about 1.6 μg/L, at least about 1.7 μg/L, at least about 1.8 μg/L, at least about 1.9 μg/L, at least about 2.0 μg/L, at least about 2.1 μg/L, at least about 2.2 μg/L, at least about 2.3 μg/L, at least about 2.4 μg/L, at least about 2.5 μg/L, at least about 3.0 μg/L, at least about 4.0 μg/L, at least about 5.0 μg/L, at least about 10.0 μg/L, at least about 15.0 μg/L, at least about 20.0 μg/L, at least about 25.0 μg/L, at least about 30.0 μg/L, at least about 35.0 μg/L, at least about 40.0 μg/L, at least about 45.0 μg/L, at least about 50.0 μg/L, at least 100.0 μg/L, at least about 150.0 μg/L, at least about 200.0 μg/L, at least about 250.0 μg/L, at least about 300.0 μg/L, at least about 350.0 μg/L, at least about 400.0 μg/L, at least about 450.0 μg/L, at least about 500.0 μg/L, at least about 600.0 μg/L, at least about 700.0 μg/L, at least about 800.0 μg/L, at least about 900.0 μg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more.

Implementation 57. The method of any one of Implementations 52-56, wherein the bakuchiol is produced by culturing a transgenic cell expressing a bakuchiol-producing enzyme in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 58. The method of Implementation 57, wherein the culture medium further comprises about 3% w/v maltodextrin, about 0.2% w/v glucose, alpha-amylase, or any combination thereof.

Implementation 59. The method of Implementation 57 or 58, wherein the culture medium comprises at least about 1.50 mM p-coumaric acid, at least about 1.75 mM p-coumaric acid, at least about 2.00 p-coumaric acid, at least about 2.25 mM p-coumaric acid, at least about 2.50 mM p-coumaric acid, at least about 2.75 mM p-coumaric acid, at least about 3.00 p-coumaric acid, at least about 3.25 mM p-coumaric acid, at least about 3.50 mM p-coumaric acid, at least about 3.75 mM p-coumaric acid, at least about 4.00 p-coumaric acid or more.

Implementation 60. The method of any one of Implementations 57-58, wherein the culture medium does not comprise exogenous p-coumaric acid, GPP, DMAPP, IPP, or a combination thereof.

Implementation 61. The method of any one of Implementations 57-60, wherein at least about 0.1 µg/L, at least about 0.2 µg/L, at least about 0.3 µg/L, at least about 0.4 µg/L, at least about 0.5 µg/L, at least about 0.6 µg/L, at least about 0.7 µg/L, at least about 0.8 µg/L, at least about 0.9 µg/L, at least about 1.0 µg/L, at least about 1.1 µg/L, at least about 1.2 µg/L, at least about 1.3 µg/L, at least about 1.4 µg/L, at least about 1.5 µg/L, at least about 1.6 µg/L, at least about 1.7 µg/L, at least about 1.8 µg/L, at least about 1.9 µg/L, at least about 2.0 µg/L, at least about 2.1 µg/L, at least about 2.2 µg/L, at least about 2.3 µg/L, at least about 2.4 µg/L, at least about 2.5 µg/L, at least about 3.0 µg/L, at least about 4.0 µg/L, at least about 5.0 µg/L, at least about 10.0 µg/L, at least about 15.0 µg/L, at least about 20.0 µg/L, at least about 25.0 µg/L, at least about 30.0 µg/L, at least about 35.0 µg/L, at least about 40.0 µg/L, at least about 45.0 µg/L, at least about 50.0 µg/L, at least 100.0 µg/L, at least about 150.0 µg/L, at least about 200.0 µg/L, at least about 250.0 µg/L, at least about 300.0 µg/L, at least about 350.0 µg/L, at least about 400.0 µg/L, at least about 450.0 µg/L, at least about 500.0 µg/L, at least about 600.0 µg/L, at least about 700.0 µg/L, at least about 800.0 µg/L, at least about 900.0 µg/L, at least about 1.00 mg/L, at least about 1.25 mg/L, at least about 1.50 mg/L, at least about 1.75 mg/L, at least about 2.00 mg/L, at least about 2.25 mg/L, at least about 2.50 mg/L, at least about 2.75 mg/L, at least about 3.00 mg/L, at least about 3.25 mg/L, at least about 3.50 mg/L, at least about 3.75 mg/L, at least about 4.00 mg/L, at least about 4.00 mg/L, at least about 4.25 mg/L, at least about 4.50 mg/L, at least about 4.75 mg/L, at least about 5.00 mg/L or more of bakuchiol within at least about 48 hours of culture.

Implementation 62. A method of producing bakuchiol, comprising:
(a) culturing a transgenic cell comprising a transgene encoding a transgenic bakuchiol-producing enzyme in a culture medium comprising p-coumaric acid and optionally comprising (i) geranyl pyrophosphate (GPP), (ii) dimethylallyl pyrophosphate (DMAPP), (iii) isopentenyl pyrophosphate (IPP), or any combination of (i)-(iii);
(b) isolating bakuchiol from the culture medium; and
(c) determining an amount of bakuchiol isolated from the culture medium by mass spectrometry, wherein determining comprises:
(i) ionizing bakuchiol from the sample to generate one or more ions detectable by mass spectrometry;
(ii) determining an amount of bakuchiol ions by multiple reaction or high resolution accurate mass spectrometry; and
(iii) relating the amount of bakuchiol ions to the amount of bakuchiol in the sample, wherein a limit of detection of the method for bakuchiol is between about 0.001 µg/L and 0.0001 µg/L.

Implementation 63. The method of Implementation 62, wherein the transgenic cell is prokaryotic.

Implementation 64. The method of Implementation 63, wherein the transgenic cell is selected from *Escherichia coli* (*E. coli*), an *Acinetobacter* species, a *Pseudomonas* species, a *Streptomyces* species, and a *Mycobacterium* species.

Implementation 65. The method of Implementation 62, wherein the transgenic cell is eukaryotic.

Implementation 66. The method of Implementation 65, wherein the transgenic cell is selected from *Saccharomyces cerevisiae* (*S. cerevisiae*) or other yeast species, a filamentous fungi, an algae, and an amoeba.

Implementation 67. The method of Implementation 66, wherein the filamentous fungi is selected from an *Aspergillus* species and a *Trichoderma* species.

Implementation 68. The method of Implementation 66, wherein the amoeba is *Dictyostelium discoideum*.

Implementation 69. The method of Implementation 66, wherein the algae is selected from *Botryococcus braunii*, *Chlorella* sp., *Crypthecodinium cohnii*, *Cylindrotheca* sp., *Nitzschia* sp., *Phaeodactylum tricornutum*, *Schizochytrium* sp., and *Tetraselmis suecia*.

Implementation 70. The method of any one of Implementations 62-69, wherein the transgene is integrated into the transgenic cell's genome.

Implementation 71. The method of any one of Implementations 62-69, wherein the transgene is not integrated into the transgenic cell's genome.

Implementation 72. The method of any one of Implementations 62-71, wherein ionizing comprises atmospheric pressure chemical ionization (APCI).

Implementation 73. The method of Implementation 72, wherein the APCI is in negative ionization mode.

Implementation 74. The method of any one of Implementations 62-71, wherein ionizing comprises electrospray ionization (ESI).

Implementation 75. The method of Implementation 74, wherein the ESI is in negative ionization mode.

Implementation 76. The method of Implementation 74 or 75, wherein the one or more ions comprise an ion with a mass to charge ratio (m/z) of 172.1±0.5.

Implementation 77. The method of any one of Implementations 62-76, wherein prior to ionizing, the sample is subjected to liquid chromatography.

Implementation 78. The method of Implementation 77, wherein the liquid chromatography is selected from high performance liquid chromatography (HPLC), ultra performance liquid chromatography (UPLC), ultra high performance liquid chromatography (UHPLC), and supercritical fluid chromatography (SFC).

Implementation 79. The method of any one of Implementations 62-71, where ionizing comprises electron impact (EI) ionization.

Implementation 80. The method of any one of Implementations 62-73 or 79, wherein prior to ionizing, the sample is subjected to gas chromatography (GC).

Implementation 81. The method of any one of Implementations 62-80, wherein prior to ionizing, the sample is diluted with an alcohol, extracted, centrifuged, or any combination thereof.

Implementation 82. A method for determining an amount of bakuchiol in a sample by mass spectrometry as disclosed herein.

Implementation 83. An isolated protein comprising an amino acid sequence with at least about 65% identity to: SEQ ID NO: 1 or SEQ ID NO: 2.

Implementation 84. The isolated protein of Implementation 83, wherein the amino acid sequence comprises at least about 70%, at least about 75% at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity with SEQ ID NO: 1 or SEQ ID NO: 2.

Implementation 85. The isolated protein of Implementation 83 or 84, wherein the protein comprises an N-terminal deletion of 1 to about 73 amino acids or 1 to about 120 amino acids.

Implementation 86. The isolated protein of any one of Implementations 83-85, wherein the protein catalyzes the production of bakuchiol, exhibits prenyltransferase activity, or both.

Implementation 87. A transgenic cell, comprising a transgene encoding the protein of any one of Implementations 83-86.

Implementation 88. The transgenic cell of Implementation 87, wherein the transgenic cell is prokaryotic.

Implementation 89. The transgenic cell of Implementation 87 or 88, wherein the transgenic cell is selected from *Escherichia coli* (*E. coli*), an *Acinetobacter* species, a *Pseudomonas* species, a *Streptomyces* species, and a *Mycobacterium* species.

Implementation 90. The transgenic cell of Implementation 87, wherein the transgenic cell is eukaryotic.

Implementation 91. The transgenic cell of Implementation 87 or 90, wherein the transgenic cell is selected from *Saccharomyces cerevisiae* (*S. cerevisiae*) or other yeast species, a filamentous fungi, an algae, and an amoeba.

Implementation 92. A method of producing bakuchiol, comprising culturing the transgenic cell according to one of Implementations 87-91 in a culture medium comprising p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 93. An engineered enzyme comprising an amino acid sequence comprising an N-terminal deletion of:
  1 to about 73 amino acids from the N-terminus of SEQ ID NO: 1, or 1 to about 120 amino acids from the N-terminus of SEQ ID NO: 2.

Implementation 94. The engineered enzyme of Implementation 93, wherein the enzyme comprises an N-terminal deletion of 29, 57, or 73 amino acids from the N-terminus of SEQ ID NO: 1.

Implementation 95. The engineered enzyme of Implementation 93, wherein the enzyme comprises an N-terminal deletion of 38, 88, 105, or 120 amino acids from the N-terminus of SEQ ID NO: 2.

Implementation 96. The engineered enzyme of Implementation 93, wherein the enzyme comprises an amino acid sequence having at least about 80%, at least about 85%, at least about 90%, at least about 95%, or 100% identity to the amino acid sequence set forth in SEQ ID NO: 3.

Implementation 97. The engineered enzyme of Implementation 96, wherein the engineered enzyme comprises at least one amino acid substitution at position 54, 71, 108, 162, 185, 199, 205, 206, 209, 226, 234, 257, 269, 274, 279, 287, 310, 312, 313, 317, 318, 319, 320, 325, 342, and 354 of SEQ ID NO: 3.

Implementation 98. The engineered enzyme of Implementation 97, wherein the enzyme comprises at least one amino acid substitution, relative to SEQ ID NO: 3, selected from the group consisting of E54F, G71D, S108L, T162H, P185V, V199G, P205L, P205V, L206Y, W209S, W209C, W209V, W209T, W209Y, W209R, W209M, W209Q, W209A, W209N, W209D, W209E, W209G, W209H, W209I, W209L, W209K, W209F, W209P, L226M, L234Q, F257E, K269R, I274L, D279C, D279K, D279R, D279M, D279L, M287V, M287F, M287Y, I310V, V312W, V312A, V312F, V312G, V312Y, V312C, V312L, G313I, S317P, S317I, F318R, F318G, L319P, W320D, T325G, S342G, and L354F.

Implementation 99. The engineered enzyme of any one of Implementations 93-98, wherein the enzyme comprises an amino acid sequence having at least 80%, at least 85%, at least 95%, or 100% identity to an amino acid sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 78, SEQ ID NO: 79, SEQ ID NO: 80, and SEQ ID NO: 81.

Implementation 100. An engineered bakuchiol-producing enzyme, comprising an N-terminal deletion of 1 to about 120 amino acids from the N-terminus of the enzyme, wherein the enzyme catalyzes production of bakuchiol, exhibits prenyltransferase activity, or both.

Implementation 101. The engineered bakuchiol-producing enzyme of Implementation 100, wherein the enzyme comprises an amino acid sequence with at least about 65% identity to SEQ ID NO: 1 or SEQ ID NO: 2.

Implementation 102. The engineered bakuchiol-producing enzyme of Implementation 100, wherein the N-terminal deletion increases catalyzation of production of bakuchiol, prenyltransferase activity, or both, relative to a non-engineered enzyme comprising a same amino acid sequence but without the N-terminal deletion.

Implementation 103. The engineered bakuchiol-producing enzyme of any one of Implementations 100-102, wherein the enzyme comprises an N-terminal deletion of 29, 57, or 73 amino acids from the N-terminus of SEQ ID NO: 1.

Implementation 104. The engineered bakuchiol-producing enzyme of any one of Implementations 100-102, wherein the enzyme comprises an N-terminal deletion of 39, 88, 105, or 120 amino acids from the N-terminus of SEQ ID NO: 2.

87

Implementation 105. The engineered bakuchiol-producing enzyme of any one of Implementations 100-102, wherein the enzyme comprises an amino acid sequence with at least about 65% identity to SEQ ID NO: 3.

Implementation 106. The engineered bakuchiol-producing enzyme of Implementation 105, wherein the engineered enzyme comprises at least one amino acid substitution, relative to SEQ ID NO: 3, at position 54, 71, 108, 162, 185, 199, 205, 206, 209, 226, 234, 257, 269, 274, 279, 287, 310, 312, 313, 317, 318, 319, 320, 325, 342, or 354.

Implementation 107. The engineered bakuchiol-producing enzyme of Implementation 106, wherein the enzyme comprises at least one amino acid substitution, relative to SEQ ID NO: 3, selected from the group consisting of E54F, G71D, S108L, T162H, P185V, V199G, P205L, P205V, L206Y, W209S, W209C, W209V, W209T, W209Y, W209R, W209M, W209Q, W209A, W209N, W209D, W209E, W209G, W209H, W209I, W209L, W209K, W209F, W209P, L226M, L234Q, F257E, K269R, I274L, D279C, D279K, D279R, D279M, D279L, M287V, M287F, M287Y, I310V, V312W, V312A, V312F, V312G, V312Y, V312C, V312L, G313I, S317P, S317I, F318R, F318G, L319P, W320D, T325G, S342G, and L354F Implementation 108. The engineered bakuchiol-producing enzyme of Implementation 105, wherein the enzyme comprises an amino acid sequence having at least 80%, at least 85%, at least 95%, or 100% identity to an amino acid sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 78, SEQ ID NO: 79, SEQ ID NO: 80, and SEQ ID NO: 81.

Implementation 109. An engineered enzyme comprising an amino acid sequence that is a variant of SEQ ID NO: 1, wherein the amino acid sequence comprises at least one substitution mutation relative to SEQ ID NO: 1 at one or more amino acid positions selected from 42, 59, 96, 150, 173, 187, 193, 194 197, 214, 222, 245, 257, 262, 267, 275, 298, 300, 301, 305, 306, 307, 308, 313, 330, and 342.

Implementation 110. An engineered enzyme comprising an amino acid sequence that is a variant of SEQ ID NO: 2, wherein the amino acid sequence comprises at least one substitution mutation relative to SEQ ID NO: 2 at one or more amino acid positions selected from 90, 107, 144, 198, 221, 235, 241, 242, 245, 262, 270, 293, 305, 310, 315, 323, 346, 348, 349, 353, 354, 355, 356, 361, 378, and 390.

Implementation 111. An engineered enzyme that catalyzes production of bakuchiol, exhibits prenyltransferase activity, or both, wherein the engineered enzyme comprises at least one substitution mutation selected from:

88

(a) substitution of a glutamate (E) corresponding to the E at position 42 of SEQ ID NO: 1 or position 90 of SEQ ID NO: 2
(b) substitution of a glycine (G) corresponding to the G at position 59 of SEQ ID NO: 1 or position 107 of SEQ ID NO: 2;
(c) substitution of a serine (S) corresponding to the S at position 96 of SEQ ID NO: 1 or position 144 of SEQ ID NO: 2;
(d) substitution of threonine (T) corresponding to the T at position 150 of SEQ ID NO: 1 or position 198 of SEQ ID NO: 2;
(e) substitution of proline (P) corresponding to the P at position 173 of SEQ ID NO: 1 or position 221 of SEQ ID NO: 2;
(f) substitution of valine (V) corresponding to the V at position 187 of SEQ ID NO: 1 or position 235 of SEQ ID NO: 2;
(g) substitution of proline (P) corresponding to the P at position 193 of SEQ ID NO: 1 or position 241 of SEQ ID NO: 2;
(h) substitution of leucine (L) corresponding to the L at position 194 of SEQ ID NO: 1 or position 242 of SEQ ID NO: 2;
(i) substitution of tryptophan (W) corresponding to the W at position 197 of SEQ ID NO: 1 or position 245 of SEQ ID NO: 2;
(j) substitution of leucine (L) corresponding to the L at position 214 of SEQ ID NO: 1 or position 262 of SEQ ID NO: 2;
(k) substitution of leucine (L) corresponding to the L at position 222 of SEQ ID NO: 1 or position 270 of SEQ ID NO: 2;
(l) substitution of phenylalanine (F) corresponding to the F at position 245 of SEQ ID NO: 1 or position 293 of SEQ ID NO: 2;
(m) substitution of lysine (K) corresponding to the K at position 257 of SEQ ID NO: 1 or position 305 of SEQ ID NO: 2;
(n) substitution of isoleucine (I) corresponding to the I at position 262 of SEQ ID NO: 1 or position 310 of SEQ ID NO: 2;
(o) substitution of aspartic acid (D) corresponding to the D at position 267 of SEQ ID NO: 1 or position 315 of SEQ ID NO: 2;
(p) substitution of methionine (M) corresponding to the M at position 275 of SEQ ID NO: 1 or position 323 of SEQ ID NO: 2;
(q) substitution of isoleucine (I) corresponding to the I at position 298 of SEQ ID NO: 1 or position 346 of SEQ ID NO: 2;
(r) substitution of valine (V) corresponding to the V at position 300 of SEQ ID NO: 1 or position 348 of SEQ ID NO: 2;
(s) substitution of glycine (G) corresponding to the G at position 301 of SEQ ID NO: 1 or position 349 of SEQ ID NO: 2;
(t) substitution of serine (S) corresponding to the S at position 305 of SEQ ID NO: 1 or position 353 of SEQ ID NO: 2;
(u) substitution of phenylalanine (F) corresponding to the F at position 306 of SEQ ID NO: 1 or position 354 of SEQ ID NO: 2;
(v) substitution of leucine (L) corresponding to the L at position 307 of SEQ ID NO: 1 or position 355 of SEQ ID NO: 2;

(w) substitution of tryptophan (W) corresponding to the W at position 308 of SEQ ID NO: 1 or position 356 of SEQ ID NO: 2;
(x) substitution of threonine (T) corresponding to the T at position 313 of SEQ ID NO: 1 or position 361 of SEQ ID NO: 2;
(y) substitution of serine (S) corresponding to the S at position 330 of SEQ ID NO: 1 or position 378 of SEQ ID NO: 2; and
(z) substitution of leucine (L) corresponding to the L at position 342 of SEQ ID NO: 1 or position 390 of SEQ ID NO: 2.

Implementation 112. An engineered enzyme that catalyzes production of bakuchiol, exhibits prenyltransferase activity, or both, wherein the engineered enzyme comprises at least one substitution mutation selected from:
(a) substitution of phenylalanine (F) at position 42 of SEQ ID NO: 1 or position 90 of SEQ ID NO: 2;
(b) substitution of aspartate (D) at position 59 of SEQ ID NO: 1 or position 107 of SEQ ID NO: 2;
(c) substitution of leucine (L) at position 96 of SEQ ID NO: 1 or position 144 of SEQ ID NO: 2;
(d) substitution of histidine (H) at position 150 of SEQ ID NO: 1 or position 198 of SEQ ID NO: 2;
(e) substitution of valine (V) at position 173 of SEQ ID NO: 1 or position 221 of SEQ ID NO: 2;
(f) substitution of glycine (G) at position 187 of SEQ ID NO: 1 or position 235 of SEQ ID NO: 2;
(g) substitution of leucine (L) or valine (V) at position 193 of SEQ ID NO: 1 or position 241 of SEQ ID NO: 2;
(h) substitution of tyrosine (Y) at position 194 of SEQ ID NO: 1 or position 242 of SEQ ID NO: 2;
(i) substitution of serine (S), cysteine (C), valine (V), threonine (T), tyrosine (Y), arginine (R), methionine (M), or glutamine (Q) at position 197 of SEQ ID NO: 1 or position 245 of SEQ ID NO: 2;
(j) substitution of methionine (M) at position 214 of SEQ ID NO: 1 or position 262 of SEQ ID NO: 2;
(k) substitution of glutamine (Q) at position 222 of SEQ ID NO: 1 or position 270 of SEQ ID NO: 2;
(l) substitution of glutamate (E) at position 245 of SEQ ID NO: 1 or position 293 of SEQ ID NO: 2;
(m) substitution of arginine (R) at position 257 of SEQ ID NO: 1 or position 305 of SEQ ID NO: 2;
(n) substitution of leucine (L) at position 262 of SEQ ID NO: 1 or position 310 of SEQ ID NO: 2;
(o) substitution of cysteine (C), lysine (K), arginine (R), methionine (M), or leucine (L) at position 267 of SEQ ID NO: 1 or position 315 of SEQ ID NO: 2;
(p) substitution of valine (V), phenylalanine (F), or tyrosine (Y) at position 275 of SEQ ID NO: 1 or position 323 of SEQ ID NO: 2;
(q) substitution of valine (V) at position 298 of SEQ ID NO: 1 or position 346 of SEQ ID NO: 2;
(r) substitution of tryptophan (W), alanine (A), phenylalanine (F), glycine (G), tyrosine (Y), cysteine (C), or leucine (L) at position 300 of SEQ ID NO: 1 or position 348 of SEQ ID NO: 2;
(s) substitution of isoleucine (I) at position 301 of SEQ ID NO: 1 or position 349 of SEQ ID NO: 2;
(t) substitution of proline (P) or isoleucine (I) at position 305 of SEQ ID NO: 1 or position 353 of SEQ ID NO: 2;
(u) substitution of arginine (R) or glycine (G) at position 306 of SEQ ID NO: 1 or position 354 of SEQ ID NO: 2;
(v) substitution of proline (P) at position 307 of SEQ ID NO: 1 or position 355 of SEQ ID NO: 2;
(w) substitution of aspartate (D) at position 308 of SEQ ID NO: 1 or position 356 of SEQ ID NO: 2;
(x) substitution of glycine (G) at position 313 of SEQ ID NO: 1 or position 361 of SEQ ID NO: 2;
(y) substitution of glycine (G) at position 330 of SEQ ID NO: 1 or position 378 of SEQ ID NO: 2; and
(z) substitution of phenylalanine (F) at position 342 of SEQ ID NO: 1 or position 390 of SEQ ID NO: 2.

Implementation 113. The engineered enzyme of any one of Implementations 109-112, wherein the substitution mutation increases catalyzation of production of bakuchiol, prenyltransferase activity, or both, relative to a non-engineered enzyme comprising the same amino acid sequence but without the substitution mutation.

Implementation 114. The engineered enzyme of any one of Implementations 109-113, further comprising an N-terminal deletion of 1-120 amino acids.

Implementation 115. An engineered enzyme, comprising an amino acid sequence that is a variant of SEQ ID NO: 3, wherein the amino acid sequence comprises at least one substitution mutation relative to SEQ ID NO: 3 at one or more amino acid positions selected from 54, 71, 108, 162, 185, 199, 205, 206, 209, 226, 234, 257, 269, 274, 279, 287, 310, 312, 313, 317, 318, 319, 320, 325, 342, and 354.

Implementation 116. An engineered bakuchiol-producing enzyme that catalyzes production of bakuchiol, exhibits prenyltransferase activity, or both, the enzyme comprising nine transmembrane domains and loops connecting the transmembrane domains, wherein the enzyme comprises at least one substitution mutation on an internal loop or an external loop of the enzyme.

Implementation 117. The engineered bakuchiol-producing enzyme of Implementation 116, wherein the enzyme comprises an N-terminus and a C-terminus, and no amino acids are substituted in the first 50 amino acids of the N-terminus or the terminal 50 amino acids of the C-terminus.

Implementation 118. The engineered enzyme of Implementation 116 or 117, wherein the substitution mutation increases catalyzation of production of bakuchiol, prenyltransferase activity, or both, relative to a non-engineered enzyme comprising the same amino acid sequence but without the substitution mutation.

Implementation 119. A transgenic cell, comprising a transgene encoding an engineered enzyme of any one of Implementations 93-118.

Implementation 120. The transgenic cell of Implementation 119, wherein the transgenic cell is prokaryotic.

Implementation 121. The transgenic cell of Implementation 120, wherein the transgenic cell is selected from *Escherichia coli* (*E. coli*), an *Acinetobacter* species, a *Pseudomonas* species, a *Streptomyces* species, a *Bacillus* species, and a *Mycobacterium* species.

Implementation 122. The transgenic cell of Implementation 119, wherein the transgenic cell is eukaryotic.

Implementation 123. The transgenic cell of Implementation 122, wherein the transgenic cell is selected from a yeast species, a filamentous fungus, an algae, and an amoeba.

Implementation 124. The transgenic cell of Implementation 123, wherein the filamentous fungus is selected from an *Aspergillus* species and a *Trichoderma* species.

Implementation 125. The transgenic cell of Implementation 123, wherein the amoeba is *Dictyostelium discoideum*.

Implementation 126. The transgenic cell of Implementation 123, wherein the algae is selected from *Botryococcus* braunii, *Chlorella* sp., *Crypthecodinium cohnii*, *Cylindrotheca* sp., *Nitzschia* sp., *Phaeodactylum tricornutum*, *Schizochytrium* sp., and *Tetraselmis suecia*.

Implementation 127. The transgenic cell of Implementation 123, wherein the yeast species is *Saccharomyces cerevisiae* (*S. cerevisiae*), *Pichia pastoris*, or *Kluyveromyces marxianus*.

Implementation 128. The transgenic cell of Implementation 123, wherein the yeast species is an oleaginous yeast.

Implementation 129. The transgenic cell of any one of Implementations 119-128, wherein the transgene is integrated into the transgenic cell's genome.

Implementation 130. The transgenic cell of any one of Implementations 119-128, wherein the transgene is not integrated into the transgenic cell's genome.

Implementation 131. The transgenic cell of any one of Implementations 119-130, wherein the engineered enzyme comprises an amino acid sequence selected from any one of SEQ ID NOs: 1-51 and 56-81.

Implementation 132. The transgenic cell of any one of Implementations 119-131, wherein the engineered enzyme has an amino acid sequence consisting of any one of SEQ ID NOs: 1-51 and 56-81.

Implementation 133. A method of producing bakuchiol, comprising culturing the transgenic cell according to one of Implementations 119-132 in a culture medium and in the presence of p-coumaric acid and (i) geranyl pyrophosphate (GPP), (ii) dimethylallyl pyrophosphate (DMAPP), (iii) isopentenyl pyrophosphate (IPP), or any combination of (i)-(iii).

Implementation 134. A bioproduction batch of bakuchiol produced by the method according to Implementation 133.

Implementation 135. A nucleic acid comprising a nucleic acid sequence encoding an engineered enzyme of any one of Implementations 94-118.

Implementation 136. An engineered host cell that produces the engineered enzyme of any one of Implementations 1-36 or that comprises the nucleic acid of Implementation 135.

Implementation 137. A bakuchiol-producing enzyme as disclosed herein.

Implementation 138. A transgenic cell capable of producing bakuchiol as disclosed herein.

Implementation 139. A method of producing bakuchiol as disclosed herein.

Some further exemplary embodiments are listed below.

Embodiment 1. A polypeptide comprising (a) an amino acid sequence having at least 65%, 70%, 75%, 80%, 85%, 90%, 95%, 97%, 98%, 99% sequence identity to SEQ ID NO: 1 or 3; and (b) a N-terminus truncation of at least one amino acid but not more than 3, 5, 10, 15, 20, 25, 30, 35, 40, 45, 50, 55, 60, 65, 70, 80, 90 or 100 amino acids relative to SEQ ID NO: 1 or 2.

Embodiment 2. The polypeptide of Embodiment 1, wherein the polypeptide is capable of catalyzing the production of bakuchiol, exhibits prenyltransferase activity, or both.

Embodiment 3. The polypeptide of Embodiment 1 or 2, wherein the polypeptide is at least 90% identical to SEQ ID NO: 3 and comprise a N-terminus truncation of between 10 and 60, between 20 and 60, between 30 and 60, between 40 and 60, between 20 and 50, between 30 and 40, between 30 and 50, or between 40 and 50 amino acids relative to SEQ ID NO: 2.

Embodiment 4. The polypeptide of any of Embodiments 1 to 3, wherein the polypeptide comprises an amino acid substitution relative to SEQ ID NO: 3 at a site corresponding to a residue position selected from the group of consisting of W209 and V312 of SEQ ID NO: 3.

Embodiment 5. The polypeptide of any of Embodiments 1 to 4, wherein the polypeptide comprises a mutation combination listed in Table 3 or 4.

Embodiment 6. The polypeptide of any of Embodiments 1 to 4, wherein the polypeptide comprises a W209C substitution, wherein the residue position is relative to SEQ ID NO: 3.

Embodiment 7. The polypeptide of any of Embodiments 1 to 4, wherein the polypeptide comprises V48S and W209C substitutions, wherein the residue position is relative to SEQ ID NO: 3.

Embodiment 8. The polypeptide of any of Embodiments 1 to 4, wherein the polypeptide comprises T65C and W209C substitutions, wherein the residue position is relative to SEQ ID NO: 3.

Embodiment 9. The isolated polypeptide of Embodiment 1 or 4, wherein the polypeptide comprises a substitution combination of E54F, W209C, D279K, M287V, V312L, F318R, and S342G, wherein the residue position is relative to SEQ ID NO: 3.

Embodiment 10. The isolated polypeptide of Embodiment 1 or 4, wherein the polypeptide comprises a substitution combination of P205L, L206Y, W209Y, M287V, V312L, and S342G, wherein the residue position is relative to SEQ ID NO: 3.

Embodiment 11. The isolated polypeptide of Embodiment 1 or 4, wherein the polypeptide comprises a substitution combination of T65C, L206Y, W209I, I274L, D279L, M287F, V312Y, E350G, and L354F, wherein the residue position is relative to SEQ ID NO: 3.

Embodiment 12. The isolated polypeptide of Embodiment 1 or 4, wherein the polypeptide comprises a substitution combination of P185V, W209V, L226M, D279K, V312L, S342G, and L354F, wherein the residue position is relative to SEQ ID NO: 3.

Embodiment 13. The isolated polypeptide of Embodiment 1 or 4, wherein the polypeptide comprises a substitution combination of I274L, D279R, V312W, and L354F, wherein the residue position is relative to SEQ ID NO: 3.

Embodiment 14. The isolated polypeptide of Embodiment 1 or 4, wherein the polypeptide comprises a substitution combination of T162H, P185V, V199G, P205L, L206Y, W209V, L226M, I274L, M287F, G313I, F318R, T325G, and L354F wherein the residue position is relative to SEQ ID NO: 3.

Embodiment 15. The isolated polypeptide of Embodiment 1 or 4, wherein the polypeptide comprises a substitution combination of E54F, S108L, V199G, L206Y, W209S, K269R, I274L, D279M, M287V, V312F, S317I, and S342G wherein the residue position is relative to SEQ ID NO: 3.

Embodiment 16. The isolated polypeptide of Embodiment 1 or 4, wherein the polypeptide comprises a substitution combination of V199G, P205L, L226M, M287V, S317I, F318R, and S342G, wherein the residue position is relative to SEQ ID NO: 3.

Embodiment 17. The isolated polypeptide of Embodiment 1 or 4, wherein the polypeptide comprises a substitution combination of S108L, T162H, P185V, V199G, P205L, L206Y, W209S, L234Q, D279R, and V312F, wherein the residue position is relative to SEQ ID NO: 3.

Embodiment 18. The isolated polypeptide of Embodiment 1 or 4, wherein the polypeptide comprises a substitution combination of S108L, T162H, P185V, V199G, P205L, L206Y, W209S, L234Q, D279R, and V312F, wherein the residue position is relative to SEQ ID NO: 3.

Embodiment 19. The isolated polypeptide of Embodiment 1 or 4, wherein the polypeptide comprises a substitution combination of V48S, P185V, P205L, W209T, I274L, D279M, M287F, V312C, G313I, and F318R, wherein the residue position is relative to SEQ ID NO: 3.

Embodiment 20. The isolated polypeptide of Embodiment 1 or 4, wherein the polypeptide comprises a substitution combination of E54F, T162H, P185V, L206Y, L234Q, K269R, I274L, D279M, M287V, V312Y, S342G, and L354F, wherein the residue position is relative to SEQ ID NO: 3.

Embodiment 21. The isolated polypeptide of Embodiment 1 or 4, wherein the polypeptide comprises a substitution combination of G71D, S108L, T162H, P185V, V199G, P205L, L206Y, W209S, L226M, L234Q, I274L, M287V, V312W, and F318R, wherein the residue position is relative to SEQ ID NO: 3.

Embodiment 22. The isolated polypeptide of Embodiment 1 or 4, wherein the polypeptide comprise a sequence selected from the group consisting of SEQ ID Nos: 67 to 81.

Embodiment 23. A nucleic acid molecule encoding the polypeptide of any of Embodiments 1 to 22.

Embodiment 24. A cell expressing the polypeptide of any of Embodiments 1 to 24.

Embodiment 25. A microbial cell expressing the polypeptide of any of Embodiments 1 to 25.

Embodiment 26. A microbial cell expressing a bakuchiol synthase and capable of producing bakuchiol.

Embodiment 27. The microbial cell of Embodiment 25 or 26, wherein the microbial cell is *E. coli* or yeast.

Embodiment 28. The microbial cell of Embodiment 25 or 26, wherein the microbial cell is *E. coli* or *Saccharomyces cerevisiae*.

Embodiment 29. The microbial cell of any of Embodiments 26 to 28, wherein the bakuchiol synthase is (i) BAK28 or a variant thereof, or (ii) BAK36 or a variant thereof.

NON-LIMITING WORKING EXAMPLES

The following examples are given to illustrate the present disclosure. It should be understood, however, that the disclosure is not to be limited to the specific conditions or details described in these examples.

I. Example 1—Identification of Bakuchiol-Producing Proteins and Bioproduction in Yeast To identify bakuchiol-producing enzymes, a transcriptome analysis was performed on RNA-SEQ datasets of known bakuchiol producers, *Psoralea corylifolia*, *Piper Longum* and *Ulmus davidiana*. The transcriptomes were assembled and searched for prentyltranferase enzymes using both a homology-based and PFAM HMM-based approaches. The homology-based search used four candidate enzymes with known GPP or DMAPP prenyltranferase activity. In addition, the three transcriptomes were searched for known terpene synthase containing motifs, DDxxD, NSE/DTE, and RRx(8)W.

To assemble the transcriptomes adaptors and low-quality bases were trimmed out at the ends from the fastq files using trim-galore (bioinformatics.babraham.ac.uk/projects/trim_galore). Reads were assembled as described in Grabherr et al., *Nature biotechnology*, 2011, 29(7), 644-652 (doi.org/10 .038/nbt.1883; i.e., "Trinity". Gene expression levels and assembly statistics were calculated as described in Haas et al., *Nature protocols*, 2013, 8(8), 1494-1512 (doi.org/10.1038/nprot.2013.084). The transcriptomes were assessed for quality, and open reading frames (ORFs) were identified and translated into protein sequences.

A homology sear was performed for candidate prenyltransferases using the following query candidates:
C1PT1_lemon A0A077K8G3|CGT1A_CITLI Coumarin 8-geranyltransferase 1, chloroplastic OS=*Citrus limon*;
FtmPT1 B0YAZ2|B0YAZ2_ASPFC Prenyltransferase FtmPT1 OS=*Neosartorya fumigata* (strain CEA10);
PGT1 Q8W405|PGT1_LITER 4-hydroxybenzoate geranyltransferase 1 OS=*Lithospermum erythrorhizon*; and
OGT *Morus alba* oxyresveratrol geranyltransferase (OGT).

Profile based searches for PFAM families were performed using the methods described in Wheeler et al., Bioinformatics, 2013, 29: 2487-2489. The PFAM families are listed below.
PF00432 (Prenyltransferase);
PF01239 (Protein prenyltransferase alpha subunit repeat);
PF01397 (Terpene synthase, N-terminal domain);
PF03936 (Terpene synthase family, metal binding domain);
PF06330 (Trichodiene synthase); and
PF19086 (Terpene synthase family 2, C-terminal metal binding).

Sequences matching "prenyl transferase" in their annotations in Uniprot database were also searched.

Blast searches were performed using e-value cutoff of 1E-30 and query coverage of 80%.

Hmm searches were performed using e-value cutoff of 1E-15.

All search hits were annotated using Blast against the public nr database.

Prenyltransferase hit results were trimmed to a total of 196 polypeptides, removing transcripts:
under 200 amino acids in length,
over 700 amino acids in length,
close isoforms,
3' truncation or sequences without start codon and stop codons, and
under 0.3 TPM (transcripts per million).

All putative prenyltranferase enzymes (referred to herein as "BAK genes") were integrated into *S. cerevisiae* via standard LiAc chemical transformation methodologies using a Cas12-based system for directed nuclease-guided genomic integration. The BAK genes were expressed from the GAL80 locus, driven by a GAL1 promoter and GAT2 terminator.

Resulting strains were grown and assayed at 30° C. in 96 mid-well plates with 3% w/v maltodextrin, 0.2% glucose defined medium (modified from Westfall 2012) with alpha-amylase for 24-48 hours, before transfer to the same medium with and 1.5-3 mM p-Coumaric Acid for 48 hours.

Bakuchiol was detected by LCMS using an Agilent 1290 UHPLC and a 6460 triple-quadrupole mass spectrometer. Quantitation and compound identity were determined by using an external standard curve of an authentic sample of bakuchiol. Briefly, microfermentation samples were diluted with isopropyl alcohol, extracted, centrifuged, and then the supernatant was transferred into an appropriate vial or plate. Samples were separated on a Waters BEH 50 mm×2.1 mM column, heated to 70° C., using water and acetonitrile mobile phases with a flow rate of 0.5 mL/min. The gradient consisted of the following steps: 0 minutes 0% B, 1 minutes 99% B, 2 minutes 99% B, and 2.1 minutes 0% B. The gradient used a linear ramp for all transitions, and the method was 3 minutes long. A specific MRM was used to detect bakuchiol in the mass spectrometry with an ESI source in the negative ion mode: Parent 255.2 m/z (unit), Product 172.1 m/z, Fragmenter 120V, Collision Energy 20 V, Cell Accelerator Voltage 5V with a 300 ms dwell time. Optical detection was also conducted at 260 nm with a 0.5 s response time.

Figure 2:
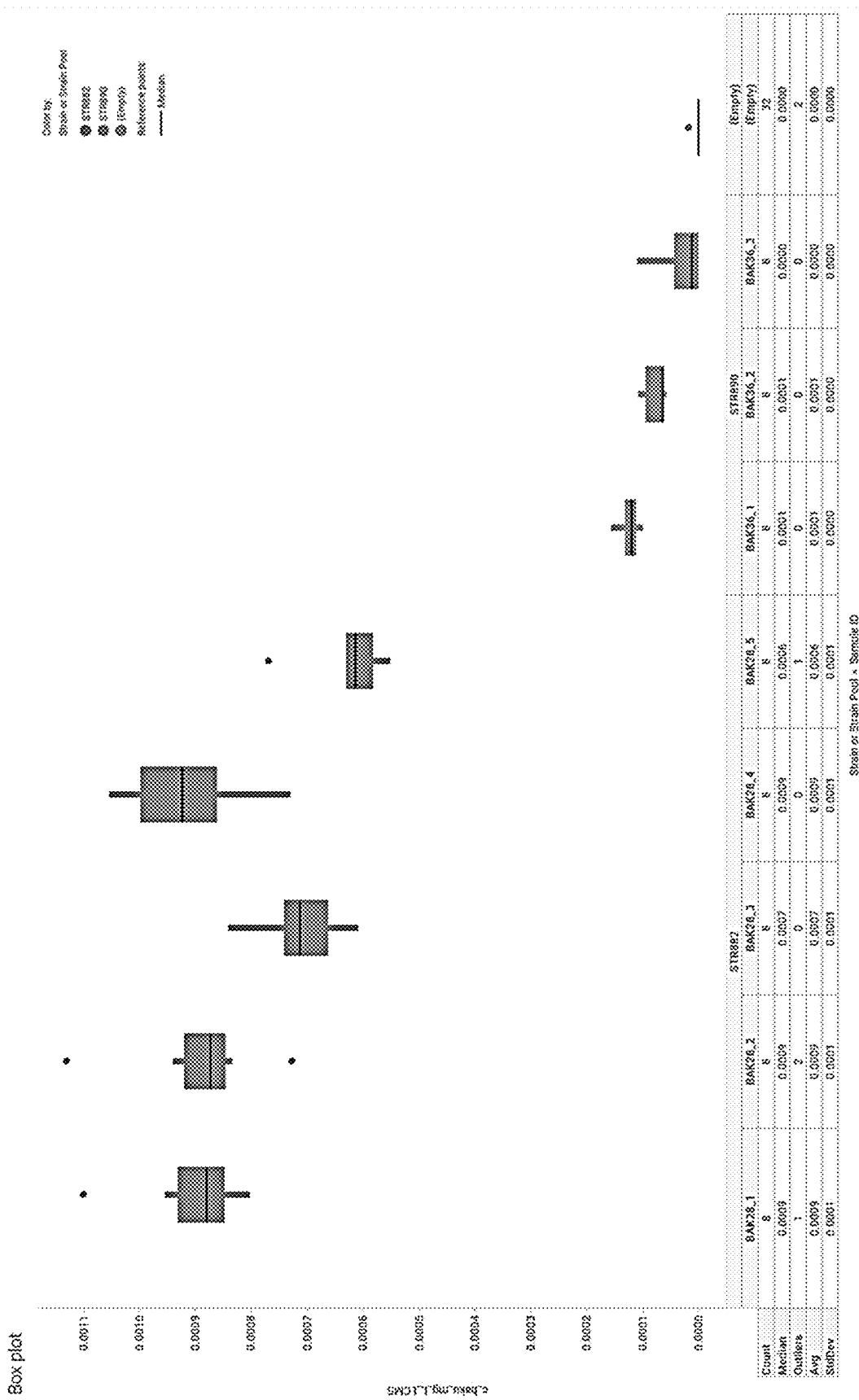
FIG. 2 (FIG. 2) shows, in one implementation, quantification of the bakuchiol produced by BAK28 and BAK36. The five BAK28 bio replicates have similar titer around 1.0 µg/L. The three BAK36 bio replicates have similar around 0.1 µg/L FIG. 3 (FIG. 3) shows, in one implementation, the p-coumaric acid involved for bakuchiol production, and increasing p-coumaric acid can augment production of bakuchiol. For example, in BAK28, production peaked at 2.0 µg/L at a p-coumaric acid concentration of 209 mg/L.
Figure 3:
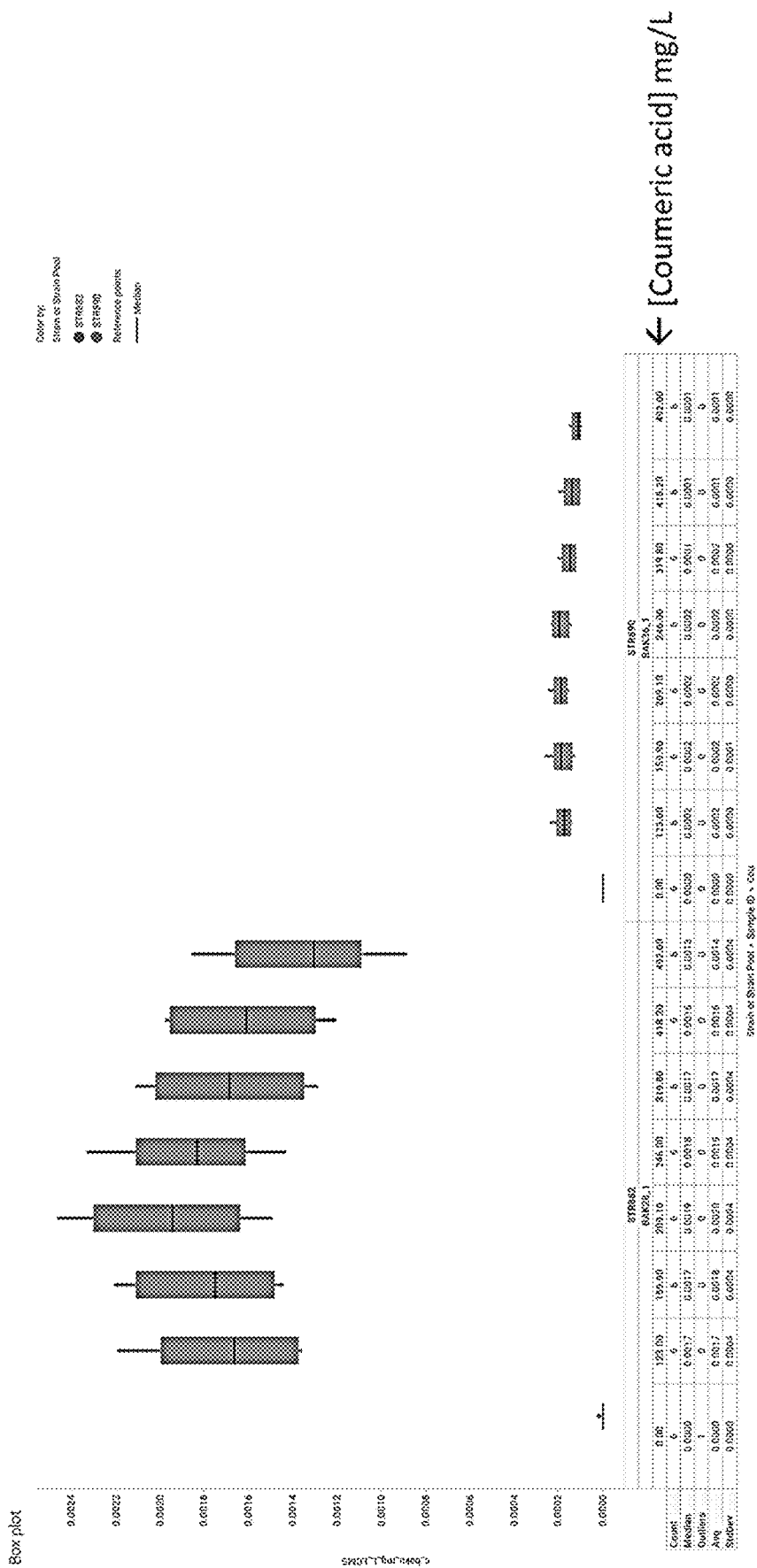

Two strains, expressing BAK28 (SEQ ID NO: 1) and BAK36 (SEQ ID NO: 2) showed specific production of Bakuchiol that was not detected in the other samples or in the negative control (FIG. 1—top 2 lines). The putative bakuchiol peak retained shape across standard addition with the expected area change (FIG. 1—third line) and showed the expected MS/MS spectra (FIG. 1—right panel), further confirming the identity of the peak. The amount of bakuchiol produced was measured to be ~1 ug/L for BAK28 and ~0.1 ug/L for BAK36 (FIG. 2). The addition of p-coumaric acid to the mediums was required for the formation of bakuchiol, further supporting the proposed mechanism (FIG. 3, zero p-coumaric acid). In addition, titration of p-coumaric acid showed that 3 mM or just over 200 mg/L doubled the production of bakuchiol under the current strain conditions (FIG. 3).

Figure 4:
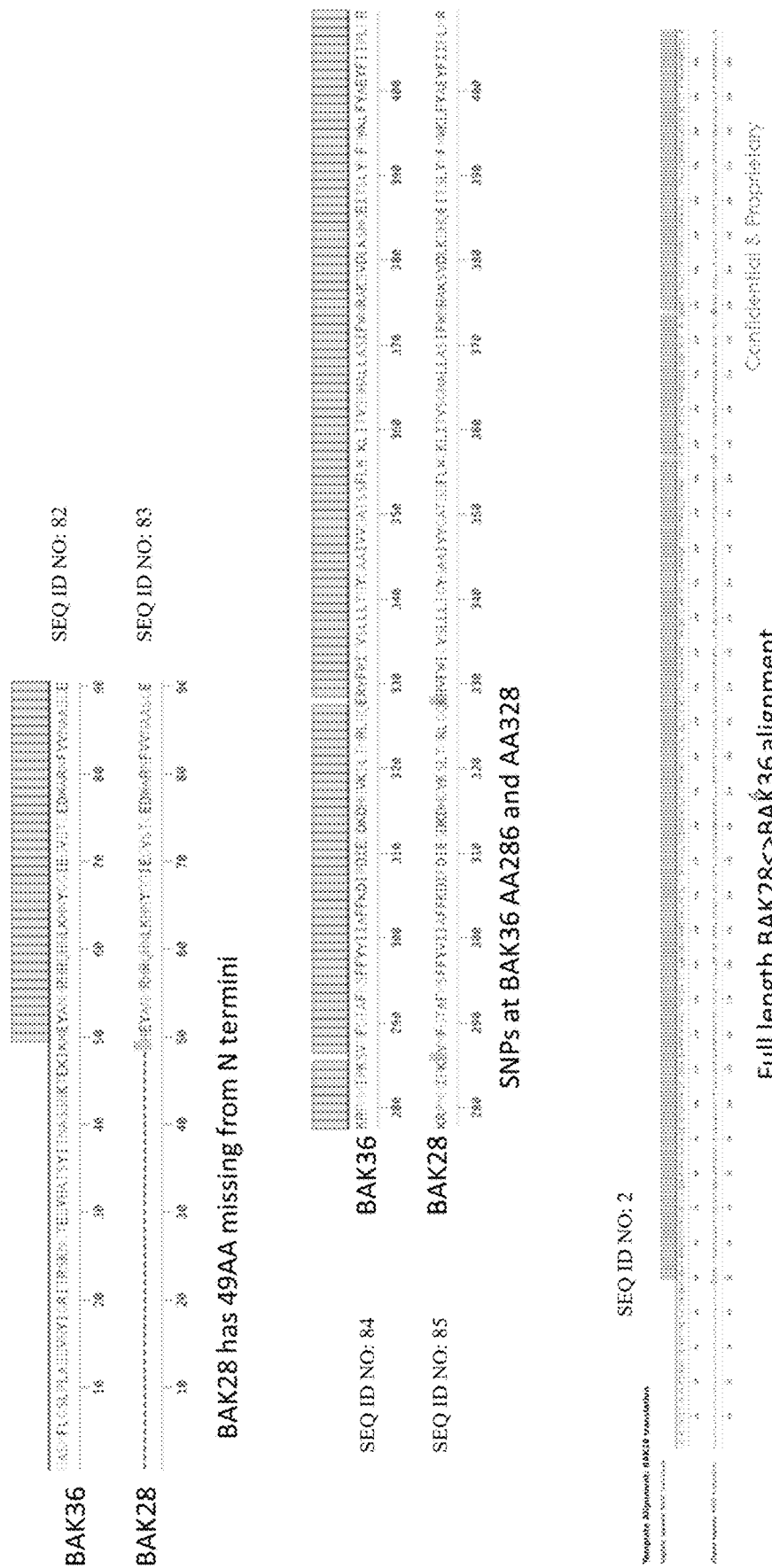
FIG. 4 (FIG. 4) shows, in one implementation, a sequence alignment of BAK28 and BAK36.

Sequence alignment and TOPCONS transmembrane analysis of the two polypeptides shows that BAK28 is a truncation of BAK36 with two additional amino acid changes and that both are predicted to have several transmembrane regions (FIG. 4, FIG. 5; BAK SEQS tab1; topcons.cbr.su.se/pred/).

To further optimize the polypeptide sequence present in the three plant transcriptomes, the sequence of BAK36 was used to search for similar polypeptides using e-value cut off of 1e-10. Unique hits from all transcriptomes were combined and annotated, using blast against the public nr database (but run locally). 178 hits were returned and all fifteen sequences with TPM levels above ten were ordered for further analysis (BAK SEQS tab2). Each of these fifteen sequences will be transduced into *S. cerevisiae* as described above and screened for bakuchiol production.

Figure 6:
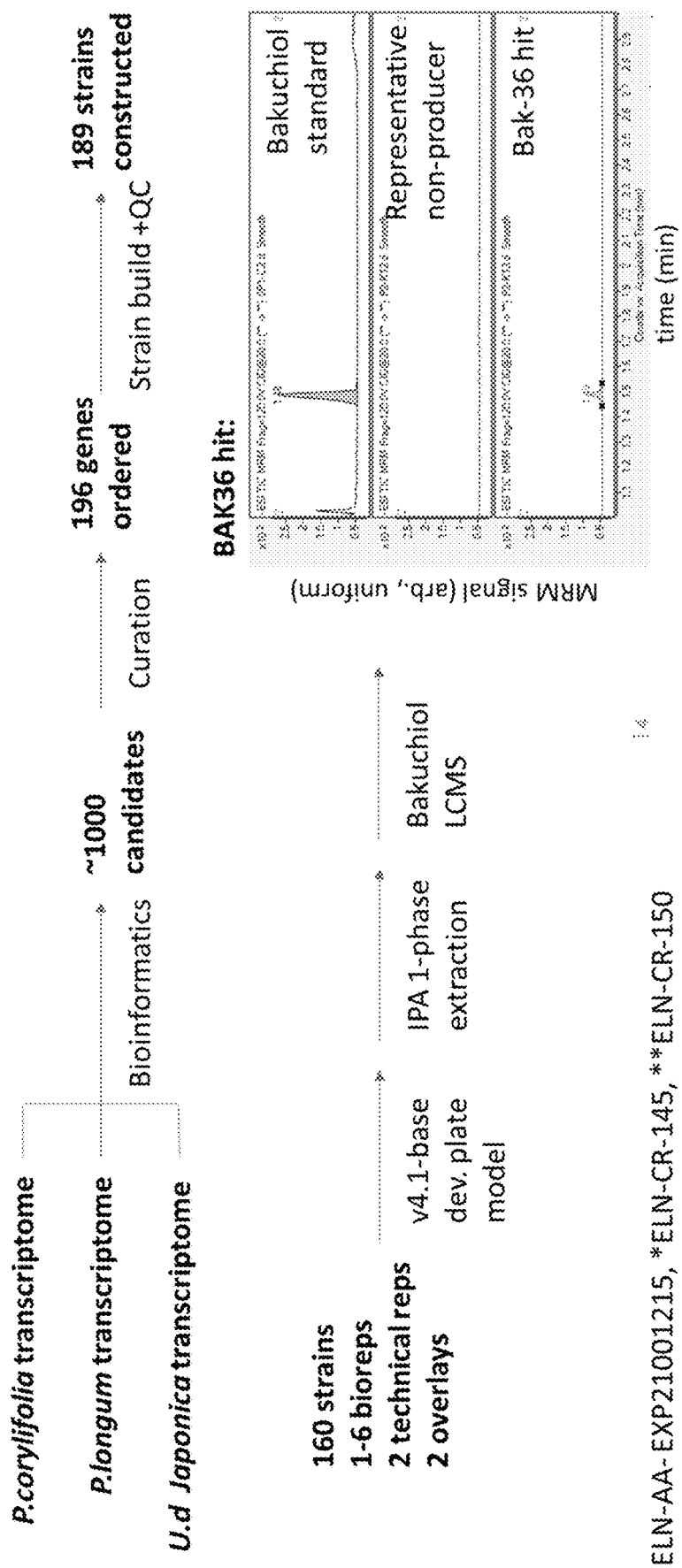
FIG. 6 (FIG. 6) shows, in one implementation, a flowchart of the process used to prepare engineered *S. cerevisiae* expressing putative bakuchiol-producing proteins.

A flow chart summarizing the foregoing strain engineering is provided in FIG. 6. As shown in FIG. 7, Blast analysis of SEQ ID NOs: 1 and 2 (i.e., BAK28 and BAK36, respectively) had no close homologs in the NCBI database, indicated that the disclosed proteins have not been previously discovered.

Figure 8:
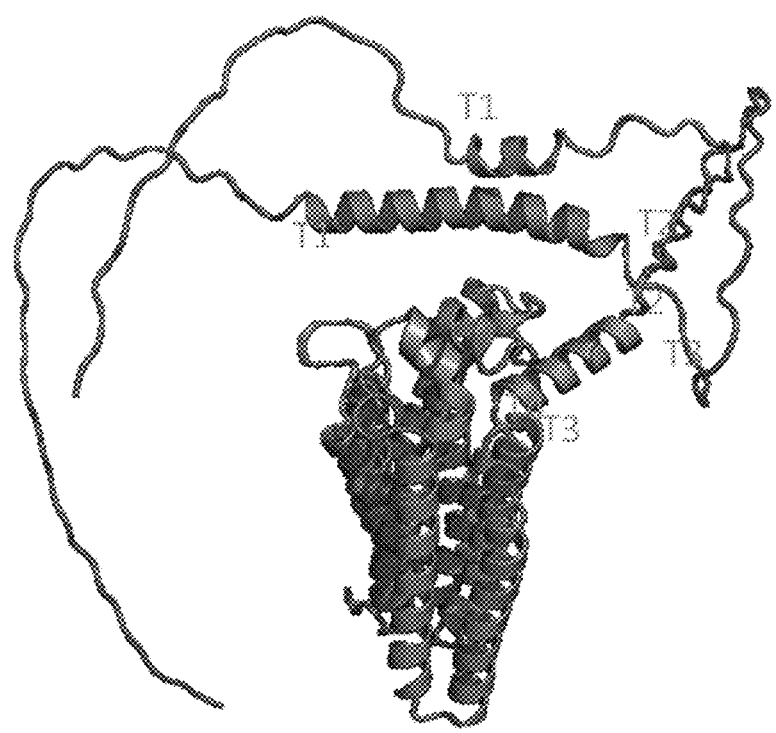
FIG. 8 (FIG. 8) shows, in one implementation, an illustration of the predicted protein structures of BAK28 and BAK36 generated using AlphaFold.

II. Example 2—Engineering of Bakuchiol-Producing Proteins and Bioproduction in Yeast N-terminal trafficking sequences are common in plant enzymes. Many times, these N-terminal domains can become problematic when plant enzymes are expressed in heterologous organisms. To ensure that bakuchiol-producing enzyme engineering began with an optimized version of BAK28 and BAK36 for yeast expression, a series of N-terminal truncations were performed. Shown in FIG. 8 are the structures of BAK28 and BAK36 predicted by AlphaFold. N-terminal truncations of each of BAK28 and BAK36 were generated, resulting in truncation variants that begin with the indicated amino acid relative to SEQ ID NO: 1 (for BAK28) or SEQ ID NO: 2 (for BAK36). For example, BAK28 (T1) comprises an amino acid sequence that lacks the first 28 N-terminal amino acids of SEQ ID NO: 1 (T1:AA29-).

All putative prenyltranferase enzymes (referred to herein as "BAK genes") were integrated into *S. cerevisiae* via standard LiAc chemical transformation methodologies using a Cas12-based system for directed nuclease-guided genomic integration. The BAK genes were expressed from the GAL80 locus, driven by a GAL1 promoter and GAT2 terminator unless otherwise noted in the genotype.

Resulting strains were grown and assayed at 30° C. in 96 mid-well plates with 3% w/v maltodextrin, 0.2% glucose defined medium (modified from Westfall 2012) with alpha-amylase for 24-48 hours, before transfer to the same medium with and 0-3 mM p-Coumaric Acid for 48 hours.

Primary bakuchiol screening was performed using Rapid Fire. Briefly, after incubation, samples were extracted by adding 500 uL of Isopropanol. Plates were shaken at 1,000 rpm for 15 minutes, then spun at 3,500× gravity for 5 minutes. 65 uL of sample was transferred. Bakuchiol primary screening was performed on the Agilent RapidFire with an Agilent 7010 Mass Spectrometer. Solid phase chromatography was performed using RapidFire C4 Type A columns. The injection cycle included a 1000 ms aspiration step, a 3000 ms load and wash step, 3500 ms elution step, and 750 ms recalibration step. Pump 1 used water, and Pumps 2 and 3 used 89% Acetonitrile, 10% IPA, 1% Water. 50 ng/mL 4-(4-chlorophenoxy) phenol was added as an internal standard.

The 255.2 - - - 172.1 transition was used for Bakuchiol; the 219.0 - - - 190.5 transition was used for 4-(4-chlorophenoxy) phenol.

Bakuchiol was quantified by LCMS using an Agilent 1290 UHPLC and a 6460 triple-quadrupole mass spectrometer. Quantitation and compound identity were determined by using an external standard curve of an authentic sample of bakuchiol. Briefly, microfermentation samples were diluted with isipropyl alcohol, extracted, centrifuged, and then the supernatant was transferred into an appropriate vial or plate. Samples were separated on a Waters BEH 50 mm×2.1 mM column, heated to 70° C., using water and acetonitrile mobile phases with a flow rate of 0.5 mL/min. The gradient consisted of the following steps: 0 minutes 0% B, 1 minutes 99% B, 2 minutes 99% B, and 2.1 minutes 0% B. The gradient used a linear ramp for all transitions, and the method was 3 minutes long. A specific MRM was used to detect bakuchiol in the mass spectrometry with an ESI source in the negative ion mode: Parent 255.2 m/z (unit), Product 172.1 m/z, Fragmenter 120V, Collision Energy 20 V, Cell Accelerator Voltage 5V with a 300 msec dwell time. Optical detection was also conducted at 260 nm with a 0.5 sec response time.

Figure 9:
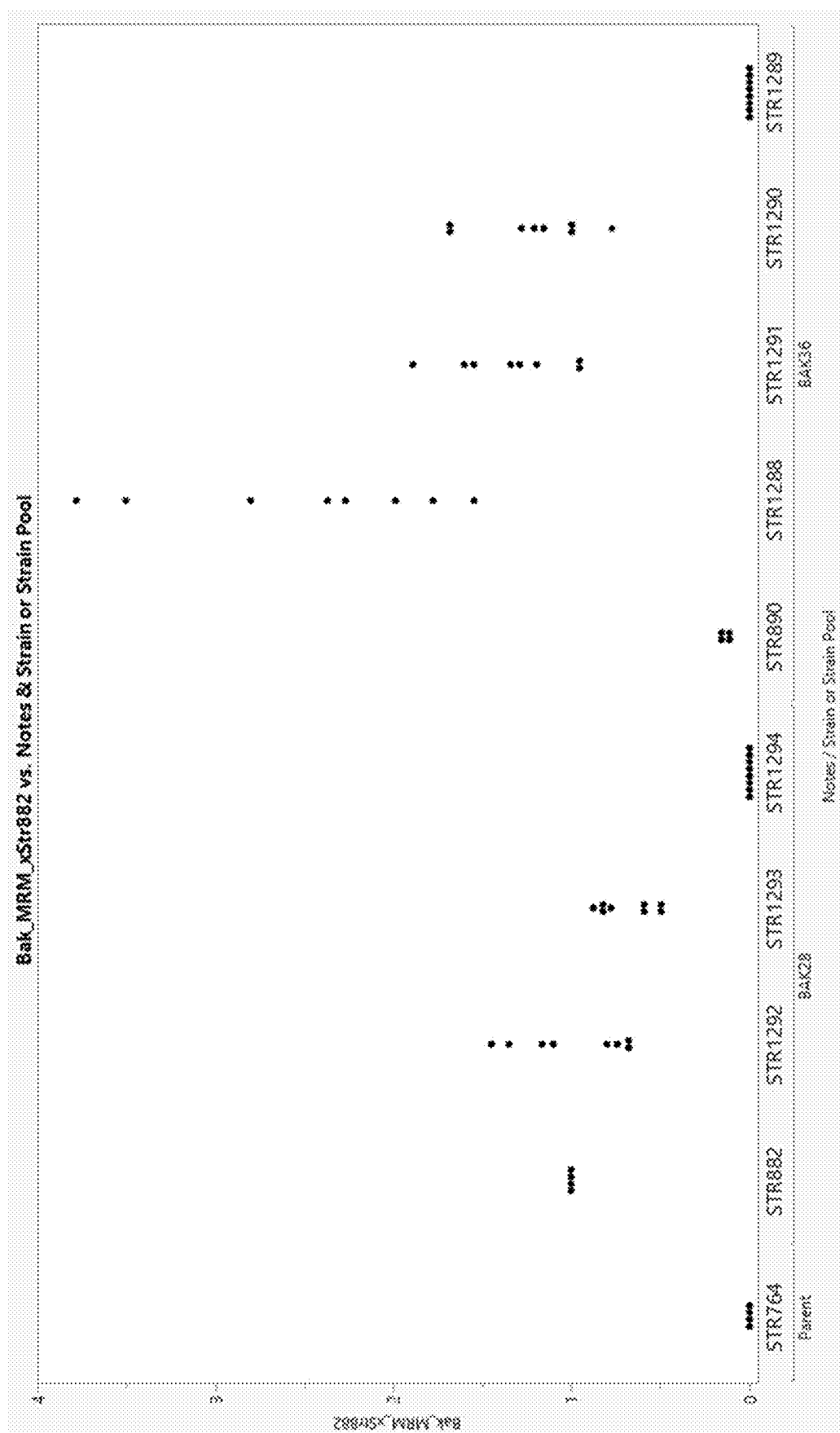
FIG. 9 (FIG. 9) shows, in one implementation, a graph of bakuchiol titers achieved by various BAK28 and BAK36 N-terminal truncation mutants relative to their respective full-length parent strains. STR764/Parent (ARS1206:: pCCW12>ERG20(F96W_N127W_K197G)-tPRM9); STR882 (GAL80^::pGAL1>BAK28-tGAT2); STR1292 (T1 deletion; GAL80^::pGAL1>BAK28(T1)-tGAT2); STR1293: (T2 deletion; GAL80^::pGAL1>BAK28(T2)-tGAT2); STR1294 (T3 deletion; GAL80^::pGAL1>BAK28(T3)-tGAT2); STR890/Parent (GAL80^::pGAL1>BAK36-tGAT2); STR1288 (T1 deletion; GAL80^::pGAL1>BAK36(T1)-tGAT2); STR1291 (T2 deletion; GAL80^:: pGAL1>BAK36(T2)-tGAT2); STR1290 (T3 deletion; GAL80^::pGAL1>BAK36(T3)-tGAT2); STR1289 (T4 deletion; GAL80^::pGAL1>BAK36(T4)-tGAT2).

Of the N-terminal truncation variants tested, BAK36(T1) increased bakuchiol titers 18-fold over parent (FIG. 9).

In order to further optimize bakuchiol production by BAK36(T1), complete saturation mutagenesis was performed on BAK36(T1) by designing an Inscripta Onyx library of about 7,100 members. Approximately 10,000 clonal samples were screened in singlicate using the plate assay previously described above. Significant hits above parent were singulated and four biological replicates were re-screened to validate each hit. A subset of samples that showed loss of titer (strikes), were also re-screened in duplicate. Validated hits and strikes were sequenced via next generation sequencing (NGS) and analyzed for both barcode and presence of edit. Sequencing analysis resulted in 48 unique hits at 26 amino acid positions (Table 2) and 149 unique strikes at 79 amino acids, with some residues having multiple amino acid substitutions resulting in phenotype. Table 2 summarizes the unique hits; the amino acid residue change shows the change relative to the corresponding amino acid position in SEQ ID NO: 3.

TABLE 2

BAK36 (T1) Unique Hits

| AA | HTS Plate Titer-fold over parent | HTS Plate Titer-CV % |
|---|---|---|
| E54F | 1.42 | 15.31% |
| G71D | 1.56 | 7.56% |
| G71D | 1.29 | 16.50% |
| S108L | 1.78 | 20.05% |
| T162H | 1.87 | 4.64% |
| P185V | 1.33 | 7.63% |
| P185V | 1.55 | 15.85% |
| V199G | 6.23 | 8.42% |
| P205L | 14.8 | 4.67% |
| P205V | 1.2 | 9.96% |
| L206Y | N/A | N/A |
| W209S | 13.32 | 2.40% |
| W209C | 24.18 | 7.73% |
| W209S | 11.85 | 7.84% |
| W209V | 14.8 | 4.67% |
| W209T | 10.92 | 8.51% |
| W209Y | 5.56 | 4.87% |
| W209Y | 5.96 | 2.70% |
| W209Y | 4.66 | 6.94% |
| W209R | 5.93 | 2.08% |
| W209M | 4.83 | 41.84% |
| W209Q | 1.33 | 9.69% |
| L226M | 1.33 | 3.36% |
| L234Q | 1.37 | 8.78% |
| F257E | 1.34 | 13.22% |
| K269R | 1.38 | 7.02% |
| I274L | 1.4 | 14.01% |
| I274L | 1.35 | 11.78% |
| I274L | 1.26 | 10.40% |
| D279C | 1.49 | 6.04% |
| D279K | 1.73 | 7.98% |
| D279R | 1.63 | 11.28% |
| D279R | 1.47 | 5.37% |
| D279M | 1.55 | 19.86% |
| D279L | 1.67 | 6.96% |
| D279L | 1.78 | 7.56% |
| D279L | 1.42 | 6.82% |
| M287V | 2.65 | 5.80% |
| M287F | 1.46 | 9.55% |
| M287F | 1.43 | 6.71% |
| M287Y | 1.4 | 9.25% |
| I310V | 1.5 | 6.24% |
| V312W | 1.55 | 3.35% |
| V312W | 1.38 | 4.33% |
| V312W | 1.42 | 9.69% |
| V312W | 1.3 | 7.23% |
| V312W | 1.3 | 14.92% |
| V312A | 1.33 | 8.29% |
| V312F | 1.19 | 3.24% |
| V312F | 1.48 | 7.77% |
| V312F | 1.42 | 17.54% |
| V312G | 1.37 | 19.67% |
| V312G | 1.49 | 7.30% |
| V312Y | 1.44 | 9.98% |
| V312Y | 1.79 | 18.41% |
| V312Y | 1.4 | 18.32% |
| V312Y | 1.69 | 5.73% |
| V312Y | 1.67 | 13.79% |
| V312Y | 1.57 | 11.21% |
| V312C | 1.32 | 8.75% |
| V312L | 1.51 | n/a |
| G313I | 1.38 | 7.02% |
| S317P | 1.37 | 19.27% |
| S317I | 1.49 | 7.22% |
| F318R | 1.65 | 15.18% |
| F318R | 1.53 | 6.19% |
| F318R | 1.46 | 8.56% |
| F318G | 1.22 | 5.27% |
| L319P | 1.34 | 22.30% |
| W320D | 1.26 | 6.27% |
| T325G | 1.37 | 7.18% |
| S342G | 1.84 | 2.48% |
| L354F | 1.68 | 4.41% |

Figure 10:
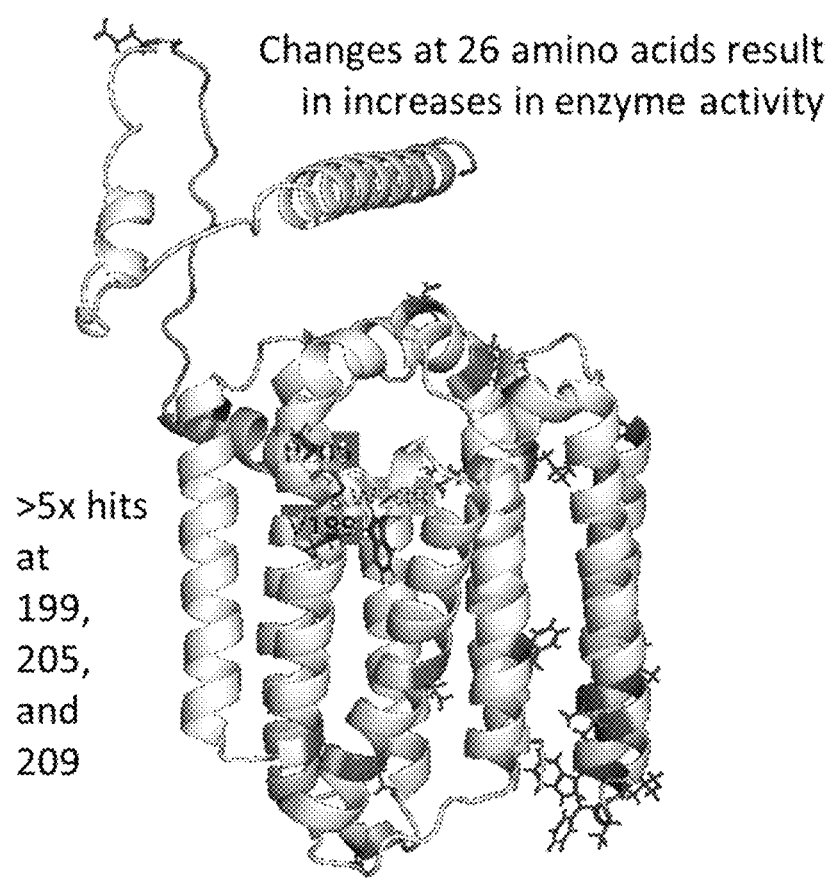
FIG. 10 (FIG. 10) shows, in one implementation, an illustration of the predicted protein structure of BAK36 generated using AlphaFold with residues V199, $P_2O_5$, and W209 highlighted. Changes in these residues increased activity.
Figure 11:
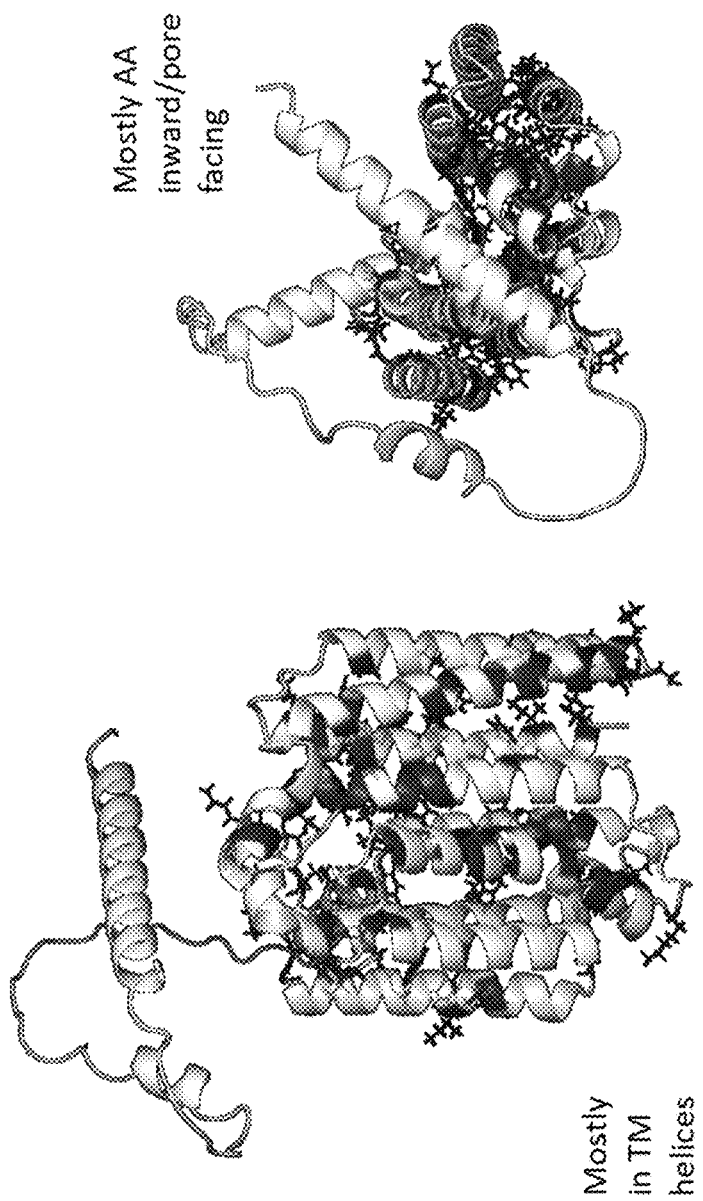
FIG. 11 (FIG. 11) shows, in one implementation, an illustration of the predicted protein structure of BAK36 generated using AlphaFold, with several residues highlighted. The residues identified in this figure either (a) decreased activity, or (b) increased activity with some substitutions but decreased activity with other substitutions. This figure discloses SEQ ID NOs: 52-55, respectively, in order of appearance.

A predicted structure of BAK36(T1) was generated using AlphaFold. The resulting structure showed 9 transmembrane (TM) regions as predicted by TOPCONS. Most of the substitutions that resulted in BAK36(T1) improvement were predicted to lie on internally or externally facing loops and not in the TM helices (FIG. 10). Substitutions at three amino acids (V199, $P_2O_5$ and W209), resulted in greater than 5-fold improvement (residues colored in pink; FIG. 10) with W209C and P205L resulting in 24-fold and 15-fold improvements, respectively. In contrast, many of the residues shown to decrease BAK36(T1) function were found to be in the TM helices or residues with side chains facing inward toward the enzyme pores (FIG. 11). The most common strikes were at residues D203, L234, K269 and G313. Several BAK36 (T1) residues had multiple amino acid substitutions that resulted in both improvement and decreases in bakuchiol production. For example, the mutations V312F, V312Y, and V312C resulted in increased bakuchiol titer, while the mutations V312M, V312A, and V312Q resulted in decreased bakuchiol titers relative to the parent strain.

Adding some of the largest single amino acid substitution hits (W209C and W209S) to our optimized strain lineages, resulted in increased production of bakuchiol in numerous genotypic contexts. This result confirmed that a bakuchiol-producing enzyme could be engineered to produce, when expressed in a microbial cell, much higher levels of bakuchiol than achieved previously. Such an engineered enzyme may be useful for large scale bioproduction of bakuchiol.

These results showed that one or more bakuchiol genetic pathway manipulations were introduced to a microbial cell expressing a bakuchiol-producing protein to enable increased production of bakuchiol by the microbial cell. These pathway manipulations, and microbial cells comprising the same, may be useful for the large scale bioproduction of bakuchiol.

III. Example 3—Full Site Saturation Mutagenesis of Tryptophan 209

Figure 12:
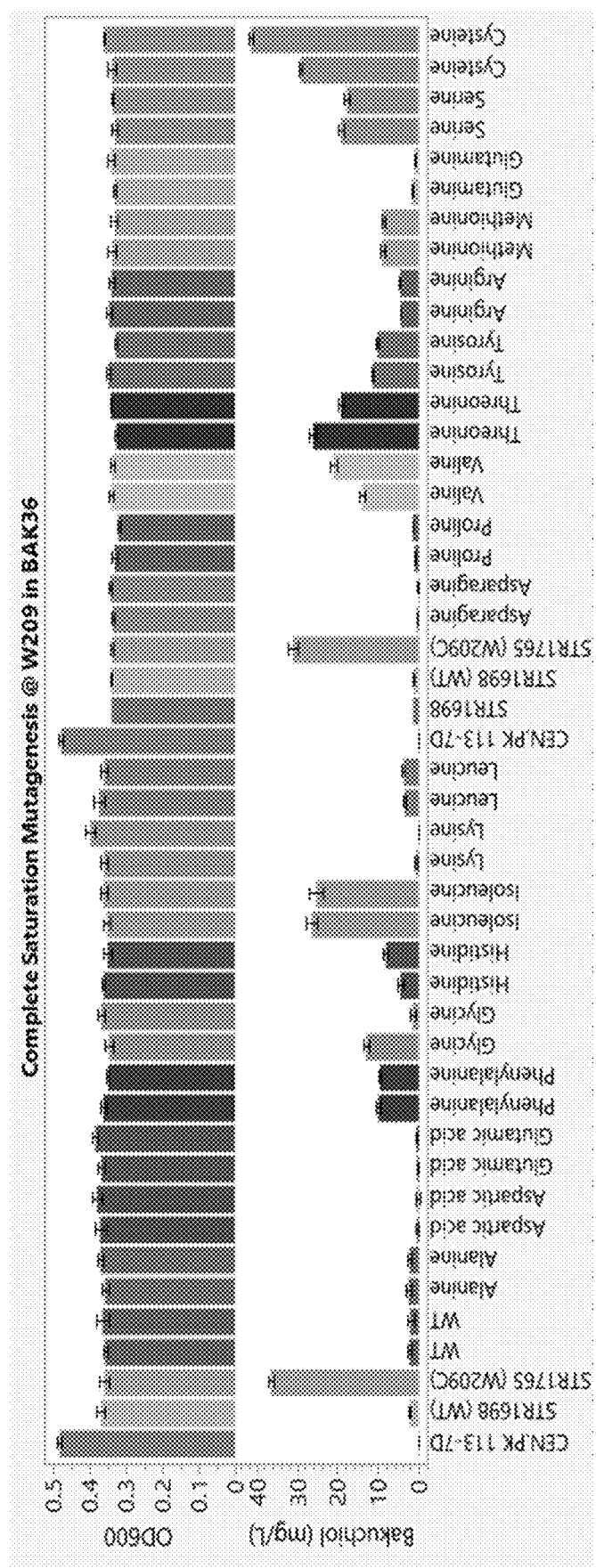
FIG. 12 (FIG. 12) shows the results of a full site mutagenesis screening in which W209 was substituted with 19 alternative amino acids.

Substitutions of the tryptophan (W) residue at amino acid position 209 of SEQ ID NO: 3 showed particular promise in yielding highly active enzyme variants. Accordingly, a full site saturation mutagenesis study was performed to substitute the W209 with every alternative amino acid. Yeast were transfected with W209 variants and screened according to the protocols in Example 2. As shown in FIG. 12, many substitutions resulted in a significant increase in bakuchiol production, including phenylalanine, glycine, histidine, isoleucine, valine, threonine, tyrosine, arginine, methionine, serine, and cysteine.

IV. Example 4—Saturation Mutagenesis in BAK36(T1, W209C)

Starting from the BAK36(T1, W209C) variant (SEQ ID 14, also referred to as the "W209C variant"), a complete saturation mutagenesis study was performed to identify additional mutation that further impact the enzymatic activity of the W209C variant. Table 3 summarizes the unique hits that exhibit highest phenotypic improvements relative to the parent strain (i.e., the W209C variant).

TABLE 3

Further engineering of BAK36 (T1, W209C). The amino acid residue change shows the change relative to the corresponding amino acid position in SEQ ID NO: 3. Two double substitutions (V48S, W209C; and T65C W209C; designated as SEQ ID NOs: 80 and 81, respectively) exhibit the biggest impact relative to the parent.

| Amino Acid Change | HTS Plate Titer-Fold Over Parent (i.e., BAK36(T1, W209C)) | HTS Plate Titer-CV % |
|---|---|---|
| V48S | 1.96 | 12.5 |
| V48S | 2.02 | 9.7 |
| V48S | 1.95 | 19.3 |
| V48S | 1.72 | 16.5 |
| V48S | 1.63 | 35.8 |
| V48S | 1.39 | 52.3 |
| T65C | 2.00 | 11.3 |
| T65C | 1.86 | 7.3 |
| T65C | 1.66 | 8.5 |
| T65C | 1.33 | 25.2 |

V. Example 5—Additional BAK36(T1) Variants

Additional BAK36(T1) variants were synthesized through a SOLD (spread out low diversity) library to combine various amino acid hits identified in Tables 2 and 3. These combinatorial variants were screened as in Example 2. Table 4 summarizes the combinational variants that exhibit phenotypic change and their fold improvement relative to the wild-type BAK36 with the T1 truncation (BAK36 (T1)). Most of the variants contain a W209 substitution and/or a V312 substitution, while three variants contain no W209 substitution, and one variant contains neither W209 nor V312 substitution.

TABLE 4

SOLD variants exhibiting improved BAK36 activity and their fold improvement relative to the wild-type BAK36 with the T1 truncation (BAK36(T1)). All amino acid residue changes shown here are relative to the corresponding amino acid position in SEQ ID NO: 3.

| SOLD Variant # | Mutant Combinations | Fold Improvement Over BAK36(T1) | SEQ ID |
|---|---|---|---|
| 1 | E54F, W209C, D279K, M287V, V312L, F318R, S342G | 138 | 67 |
| 2 | P205L; L206Y; W209Y; M287V; V312L; S342G | 63.82 | 68 |
| 3 | T65C; L206Y; W209I; I274L; D279L; M287F; V312Y; E350G; L354F | 61.15 | 69 |
| 4 | P185V; W209V; L226M; D279K; V312L; S342G; L354F | 43.40 | 70 |
| 5 | I274L; D279R; V312W; L354F | 37.90 | 71 |
| 6 | T162H; P185V; V199G; P205L; L206Y; W209V; L226M; I274L; M287F; G313I; F318R; T325G; L354F | 37.51 | 72 |
| 7 | E54F; S108L; V199G; L206Y; W209S; K269R; I274L; D279M; M287V; V312F; S317I; S342G | 32.48 | 73 |
| 8 | V199G; P205L; L226M; M287V; S317I; F318R; S342G | 30.98 | 74 |
| 9 | S108L; T162H; P185V; V199G; P205L; L206Y; W209S; L234Q; D279R; V312F | 30.82 | 75 |
| 10 | S108L; T162H; P185V; V199G; P205L; L206Y; W209S; L234Q; D279R; V312F | 30.19 | 76 |
| 11 | V48S; P185V; P205L; W209T; I274L; D279M; M287F; V312C; G313I; F318R | 30.19 | 77 |
| 12 | E54F; T162H; P185V; L206Y; L234Q; K269R; I274L; D279M; M287V; V312Y; S342G; L354F | 27.28 | 78 |
| 13 | G71D; S108L; T162H; P185V; V199G; P205L; L206Y; W209S; L226M; L234Q; I274L; M287V; V312W; F318R | 26.31 | 79 |
| | W209C | 25.98 | 14 |

It should be appreciated that all combinations of the disclosed concepts are provided as being part of the inventive subject matter disclosed herein and may be employed in any combination to achieve the benefits described herein.

The present technology is not to be limited in terms of the particular implementations described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular implementations only, and is not intended to be limiting.

What is claimed:

1. A polypeptide comprising (a) an amino acid sequence having at least 80% sequence identity to SEQ ID NO: 3; and (b) a N-terminus truncation of at least one amino acid but not more than 100 amino acids relative to SEQ ID NO: 2.

2. A nucleic acid molecule encoding the polypeptide of claim 1.

3. A cell expressing the polypeptide of claim 1.

4. The cell of claim 3, wherein the cell is a microbial cell.

5. A microbial cell expressing a bakuchiol synthase and capable of producing bakuchiol, wherein the bakuchiol synthase is (i) BAK28 or a variant thereof, or (ii) BAK36 or a variant thereof.

6. The microbial cell of claim 5, wherein the microbial cell is *E. coli* or yeast.

7. The microbial cell of claim 5, wherein the microbial cell is *E. coli* or *Saccharomyces cerevisiae*.

8. The nucleic acid molecule of claim 2, wherein the polypeptide comprises an amino acid sequence having at least 85% sequence identity to SEQ ID NO: 3.

9. The nucleic acid molecule of claim 2, wherein the polypeptide comprises an amino acid sequence having at least 90% sequence identity to SEQ ID NO: 3.

10. The nucleic acid molecule of claim 2, wherein the polypeptide comprises an amino acid sequence having at least 95% sequence identity to SEQ ID NO: 3.

11. The nucleic acid molecule of claim 2, wherein the polypeptide comprises an amino acid substitution relative to SEQ ID NO: 3 at a site corresponding to a residue position selected from W209 and V312 of SEQ ID NO: 3.

12. The nucleic acid molecule of claim 2, wherein the polypeptide comprises an amino acid sequence selected from SEQ ID NOs: 67 to 81.

13. The cell of claim 3, wherein the polypeptide comprises an amino acid sequence having at least 85% sequence identity to SEQ ID NO: 3.

14. The cell of claim 3, wherein the polypeptide comprises an amino acid sequence having at least 90% sequence identity to SEQ ID NO: 3.

15. The cell of claim 3, wherein the polypeptide comprises an amino acid sequence having at least 95% sequence identity to SEQ ID NO: 3.

16. The cell of claim 3, wherein the polypeptide comprises an amino acid substitution relative to SEQ ID NO: 3 at a site corresponding to a residue position selected from W209 and V312 of SEQ ID NO: 3.

17. The cell of claim 3, wherein the polypeptide comprises an amino acid sequence selected from SEQ ID NOs: 67 to 81.

18. The cell of claim 3, wherein the polypeptide comprises V48S and W209C substitutions, wherein the residue position is relative to SEQ ID NO: 3.

19. The cell of claim 3, wherein the polypeptide comprises T65C and W209C substitutions, wherein the residue position is relative to SEQ ID NO: 3.

20. The cell of claim 3, wherein the polypeptide comprises a substitution combination of E54F, W209C, D279K, M287V, V312L, F318R, and S342G, wherein the residue position is relative to SEQ ID NO: 3.

21. The cell of claim 3, wherein the polypeptide comprises a substitution combination of P205L, L206Y, W209Y, M287V, V312L, and S342G, wherein the residue position is relative to SEQ ID NO: 3.

* * * * *